(12) United States Patent
Cheng et al.

(10) Patent No.: US 11,542,260 B2
(45) Date of Patent: Jan. 3, 2023

(54) COMPOSITION OF MATTER FOR USE IN ORGANIC LIGHT-EMITTING DIODES

(71) Applicant: Kyulux, Inc., Fukuoka (JP)

(72) Inventors: Shuo-Hsien Cheng, Fukuoka (JP); Yu Seok Yang, Fukuoka (JP); Yoshitake Suzuki, Fukuoka (JP); Hayato Kakizoe, Fukuoka (JP); Ayataka Endo, Fukuoka (JP); Jorge Aguilera-Iparraguirre, Roslindale, MA (US); Timothy D. Hirzel, Quincy, MA (US)

(73) Assignee: KYULUX, INC., Fukuoka (JP)

(*) Notice: Subject to any disclaimer, the term of this patent is extended or adjusted under 35 U.S.C. 154(b) by 463 days.

(21) Appl. No.: 16/261,729

(22) Filed: Jan. 30, 2019

(65) Prior Publication Data

US 2019/0233412 A1 Aug. 1, 2019

Related U.S. Application Data

(60) Provisional application No. 62/624,671, filed on Jan. 31, 2018.

(51) Int. Cl.

| | | |
|---|---|---|
| *C07D 471/04* | (2006.01) | |
| *H01L 51/00* | (2006.01) | |
| *C07D 405/14* | (2006.01) | |
| *C07D 401/14* | (2006.01) | |
| *C07D 403/14* | (2006.01) | |
| *C07D 409/14* | (2006.01) | |
| *H01L 51/50* | (2006.01) | |

(52) U.S. Cl.
CPC ......... *C07D 471/04* (2013.01); *C07D 401/14* (2013.01); *C07D 403/14* (2013.01); *C07D 405/14* (2013.01); *C07D 409/14* (2013.01); *H01L 51/0058* (2013.01); *H01L 51/0067* (2013.01); *H01L 51/0072* (2013.01); *H01L 51/0073* (2013.01); *H01L 51/0074* (2013.01); *H01L 51/5012* (2013.01)

(58) Field of Classification Search
None
See application file for complete search history.

(56) References Cited

U.S. PATENT DOCUMENTS

| | | | |
|---|---|---|---|
| 9,385,348 B2 | 7/2016 | Forrest et al. | |
| 9,530,969 B2 | 12/2016 | Mizuki et al. | |
| | (Continued) | | |

FOREIGN PATENT DOCUMENTS

| | | |
|---|---|---|
| CN | 103435597 A | 12/2013 |
| CN | 102702132 B | 4/2015 |
| | (Continued) | |

OTHER PUBLICATIONS

Machine English translation of Yasukawa et al. (JP 2009-021336 A). Mar. 30, 2021.*

(Continued)

*Primary Examiner* — Jay Yang
*Assistant Examiner* — J. L. Yang
(74) *Attorney, Agent, or Firm* — Browdy and Neimark, PLLC

(57) ABSTRACT

The present disclosure relates to compounds capable of emitting delayed fluorescence and uses of these compounds in organic light-emitting diodes.

18 Claims, 1 Drawing Sheet

(56) References Cited

U.S. PATENT DOCUMENTS

| | | |
|---|---|---|
| 2010/0039026 A1 | 2/2010 | Yang et al. |
| 2011/0278555 A1 | 11/2011 | Inoue et al. |
| 2013/0234119 A1 | 9/2013 | Mizuki et al. |
| 2013/0306959 A1* | 11/2013 | Ikeda .................. H01L 51/0072 544/324 |
| 2013/0306963 A1* | 11/2013 | Yamamoto .......... H01L 51/5028 257/40 |
| 2016/0087227 A1 | 3/2016 | Kim et al. |
| 2016/0329501 A1 | 11/2016 | Kim et al. |
| 2017/0062730 A1 | 3/2017 | Ahn et al. |

FOREIGN PATENT DOCUMENTS

| | | |
|---|---|---|
| CN | 105111230 A | 12/2015 |
| CN | 105801569 A | 7/2016 |
| CN | 106316924 A | 1/2017 |
| CN | 106496198 A | 3/2017 |
| CN | 106537633 A | 3/2017 |
| CN | 108239072 A | 7/2018 |
| DE | 102009023155 A1 | 12/2010 |
| DE | 102009053382 A1 | 5/2011 |
| EP | 2851408 A1 | 3/2015 |
| EP | 2894157 A1 | 7/2015 |
| EP | 3112439 A1 | 1/2017 |
| EP | 3315581 A1 | 5/2018 |
| JP | 2009021336 A * | 1/2009 |
| JP | 2009170815 A | 7/2009 |
| JP | 2010215759 A | 9/2010 |
| JP | 4810805 B2 | 11/2011 |
| JP | 2016075739 A | 5/2016 |
| JP | 2017075121 A | 4/2017 |
| JP | 2017/197481 A | 11/2017 |
| JP | 2017197481 A * | 11/2017 |
| KR | 20120013173 A | 2/2012 |
| KR | 101212669 B1 | 12/2012 |
| KR | 20160027299 A | 3/2016 |
| KR | 20160077485 A | 7/2016 |
| KR | 20160121628 A | 10/2016 |
| KR | 20160130878 A | 11/2016 |
| KR | 101703174 B1 | 2/2017 |
| KR | 20170044821 A | 4/2017 |
| KR | 20170057796 A | 5/2017 |
| KR | 20180063708 A | 6/2018 |
| WO | WO-2010/151011 A1 | 12/2010 |
| WO | WO-2010136109 A1 | 12/2010 |
| WO | WO-2011/049325 A2 | 4/2011 |
| WO | WO-2011/057706 A2 | 5/2011 |
| WO | WO-2011071255 A1 | 6/2011 |
| WO | WO-2011081286 A2 | 7/2011 |
| WO | WO-2012/078005 A2 | 6/2012 |
| WO | WO-2012/086170 A1 * | 6/2012 |
| WO | WO-2012077902 A2 | 6/2012 |
| WO | WO-2013/085285 A1 | 6/2013 |
| WO | WO-2013/089424 A1 | 6/2013 |
| WO | WO-2013100538 A1 | 7/2013 |
| WO | WO-2013100539 A1 | 7/2013 |
| WO | WO-2013165192 A1 | 11/2013 |
| WO | WO-2014054912 A1 | 4/2014 |
| WO | WO-2014/129330 A1 | 8/2014 |
| WO | WO-2014128945 A1 | 8/2014 |
| WO | WO-2014/133062 A1 | 9/2014 |
| WO | WO-2014/146752 A1 | 9/2014 |
| WO | WO-2014/183080 A1 | 11/2014 |
| WO | WO-2015/099507 A1 | 7/2015 |
| WO | WO-2016/036171 A1 | 3/2016 |
| WO | WO-2016/072593 A1 | 5/2016 |
| WO | WO-2016/076629 A1 | 5/2016 |
| WO | WO-2016127754 A1 | 8/2016 |
| WO | WO-2016/138077 A1 | 9/2016 |
| WO | WO-2016/174377 A1 | 11/2016 |
| WO | WO-2016/181846 A1 | 11/2016 |
| WO | WO-2017/101675 A1 | 6/2017 |
| WO | WO-2017119203 A1 | 7/2017 |
| WO | WO-2018/155642 A1 | 8/2018 |
| WO | WO-2018/237385 A1 | 12/2018 |
| WO | WO-2018/237389 A1 | 12/2018 |
| WO | WO-2018/237393 A1 | 12/2018 |
| WO | WO-2019/017618 A1 | 1/2019 |

OTHER PUBLICATIONS

Machine English translation of Miyata et al. (JP-2017197481-A). Oct. 15, 2021.*

Cao et al., Simple Phenyl Bridge between Cyano and Pyridine Units to Weaken the Electron-withdrawing Property for Blue-Shifted Emission in Efficient Blue TADF OLEDs, Org Electronics, 57:247-254 (2018).

Chen et al., "Naphthyridine-based thermally activated delayed fluorescence emitters for multi-color organic llight-emitting diodes with low efficiency roll-off," J Mater Chem C, 2019, doi:10.1039/C9TC00503J.

Notice of Allowance and Fees Due for U.S. Appl. No. 16/017,274 dated Apr. 16, 2019.

Endo et al., "Efficient Up-Conversion of Triplet Excitons into a Singlet State and its Application for Organic Light Emitting Diodes," Applied Physics Letters, 98:083302 (2011).

Furukawa et al., "Dual Enhancement of electroluminescence Efficiency and Operational Stability by Rapid Upconversion of Triplet Excitons in OLEDs," Scientific Reports, 5(8429):1-8 (2015).

Gomez-Bombarelli et al., "Design of Efficient Molecular Organic Light-Emitting Diodes by a High-Throughput Virtual Screening and Experimental Approach," Nature Materials, 15:1120-1128 (2016).

Goushi et al., "Organic Light-Emitting Diodes Employing Efficient Reverse Intersystem Crossing for Triplet-to-Singlet State Conversion," Nature Phototonics, 6:253-258 (2012).

International Search Report and Written Opinion for International Application No. PCT/US2018/039295 dated Nov. 16, 2018.

International Search Report and Written Opinion for International Application No. PCT/US2018/039309 dated Nov. 16, 2018.

International Search Report and Written Opinion for International Application No. PCT/US2018/039337 dated Dec. 4, 2018.

International Search Report and Written Opinion for International Application No. PCT/US2018/049116 dated Nov. 20, 2018.

Kim et al., "A New Rigid Diindolocarbazole Donor Moiety For High Quantum Efficiency Thermally Activated Delayed Fluorescence Emitter," Journal of Materials Chemistry, 6:1343-1348 (2018).

Lee et al., "Lifetime extension in green thermally activated delayed fluorescent organic light-emitting diodes by increasing excited state bond dissociation energy," Journal of Industrial and Engineering Chemistry, 69:364-369 (2019).

Masui et al., "Analysis of Exciton Annihilation in High-Efficiency and Sky-Blue Organic Light-Emitting Diodes with Thermally Activated Delayed Flourescence," Organic Electronics, 14(2721-2726 (2013).

Nakanotani et al., "High-Efficiency Organic Light-Emitting Diodes with Fluorescent Emitters," Nature Communications, 5(4016):1-7 (2014).

Nakanotani et al., "Promising Operational Stability of High-Efficiency Organic Light-Emitting Diodes Based on Thermally Activated Delayed Flourescence," Scientific Reports, 3(2127):1-6 (2013).

Uoyama et al., "Highly Efficient Organic Light-Emitting Diodes from Delayed Fluorescence," Nature, 492:234-240 (2012).

* cited by examiner

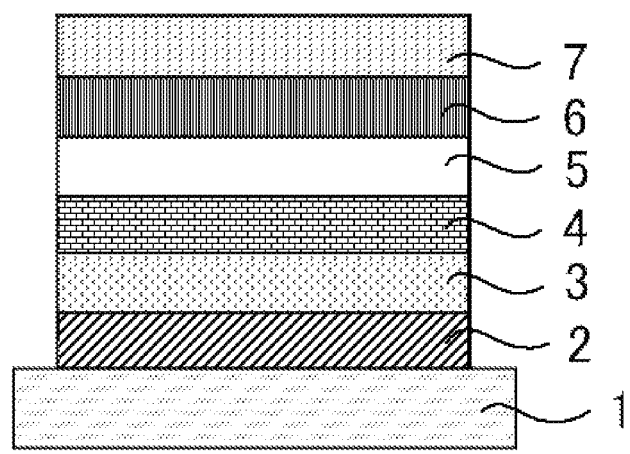

COMPOSITION OF MATTER FOR USE IN ORGANIC LIGHT-EMITTING DIODES

RELATED APPLICATION

This application claims the benefit of priority to U.S. Provisional Patent Application No. 62/624,671, filed Jan. 31, 2018.

BACKGROUND

An organic light-emitting diode (OLED) is a light-emitting diode (LED) in which a film of organic compounds is placed between two conductors, which film emits light in response to excitation, such as an electric current. OLEDs are useful in lightings and displays, such as television screens, computer monitors, mobile phones, and tablets. A problem inherent in OLED displays is the limited lifetime of the organic compounds. OLEDs which emit blue light, in particular, degrade at a significantly increased rate as compared to green or red OLEDs.

OLED materials rely on the radiative decay of molecular excited states (excitons) generated by recombination of electrons and holes in a host transport material. The nature of excitation results in interactions between electrons and holes that split the excited states into bright singlets (with a total spin of 0) and dark triplets (with a total spin of 1). Since the recombination of electrons and holes affords a statistical mixture of four spin states (one singlet and three triplet sublevels), conventional OLEDs have a maximum theoretical efficiency of 25%.

To date, OLED material design has focused on harvesting the remaining energy from the normally dark triplets. Recent work to create efficient phosphors, which emit light from the normally dark triplet state, have resulted in green and red OLEDs. Other colors, such as blue, however, require higher energy excited states which accelerate the degradation process of the OLED.

The fundamental limiting factor to the triplet-singlet transition rate is a value of the parameter $|H_{fi}/\Delta E_{ST}|^2$, where $H_{fi}$ is the coupling energy due to hyperfine or spin-orbit interactions, and $\Delta E_{ST}$ is the energetic splitting between singlet and triplet states. Traditional phosphorescent OLEDs rely on the mixing of singlet and triplet states due to spin-orbital (SO) interaction, increasing $H_{fi}$, and affording a lowest emissive state shared between a heavy metal atom and an organic ligand. This results in energy harvesting from all higher singlet and triplet states, followed by phosphorescence (relatively short-lived emission from the excited triplet). The shortened triplet lifetime reduces triplet exciton annihilation by charges and other excitons. Recent work by others suggests that the limit to the performance of phosphorescent materials has been reached.

SUMMARY

The present disclosure relates to novel materials for OLEDs. In some embodiments, these OLEDs can reach higher excitation states without rapid degradation. It has now been discovered that thermally activated delayed fluorescence (TADF), which relies on minimization of $\Delta E_{ST}$ as opposed to maximization of $H_{fi}$, can transfer population between singlet levels and triplet sublevels in a relevant timescale, such as, for example, 1 s-10 ms. The compounds described herein are capable of luminescing at higher energy excitation states than compounds previously described.

In some embodiments, the present disclosure provides compounds of Formula (I):

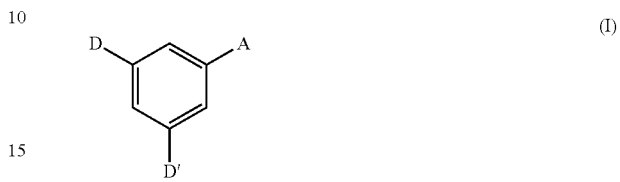

wherein
A is selected from

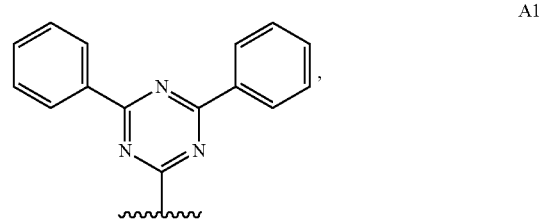

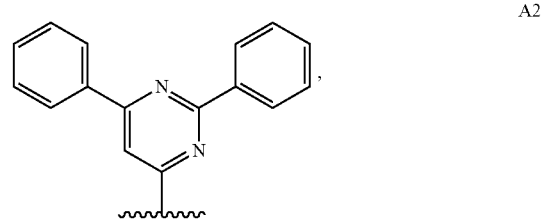

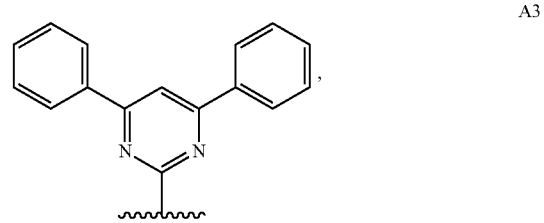

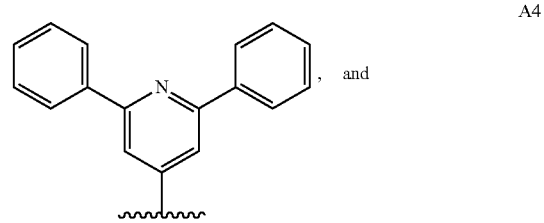

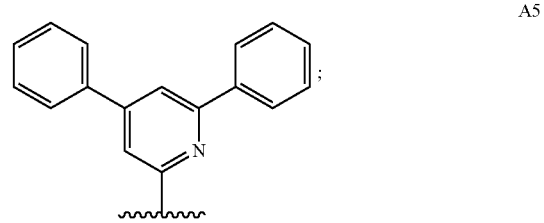

D and D' are independently selected from
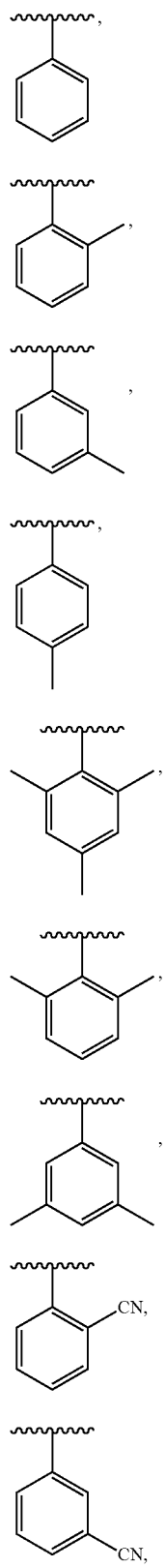
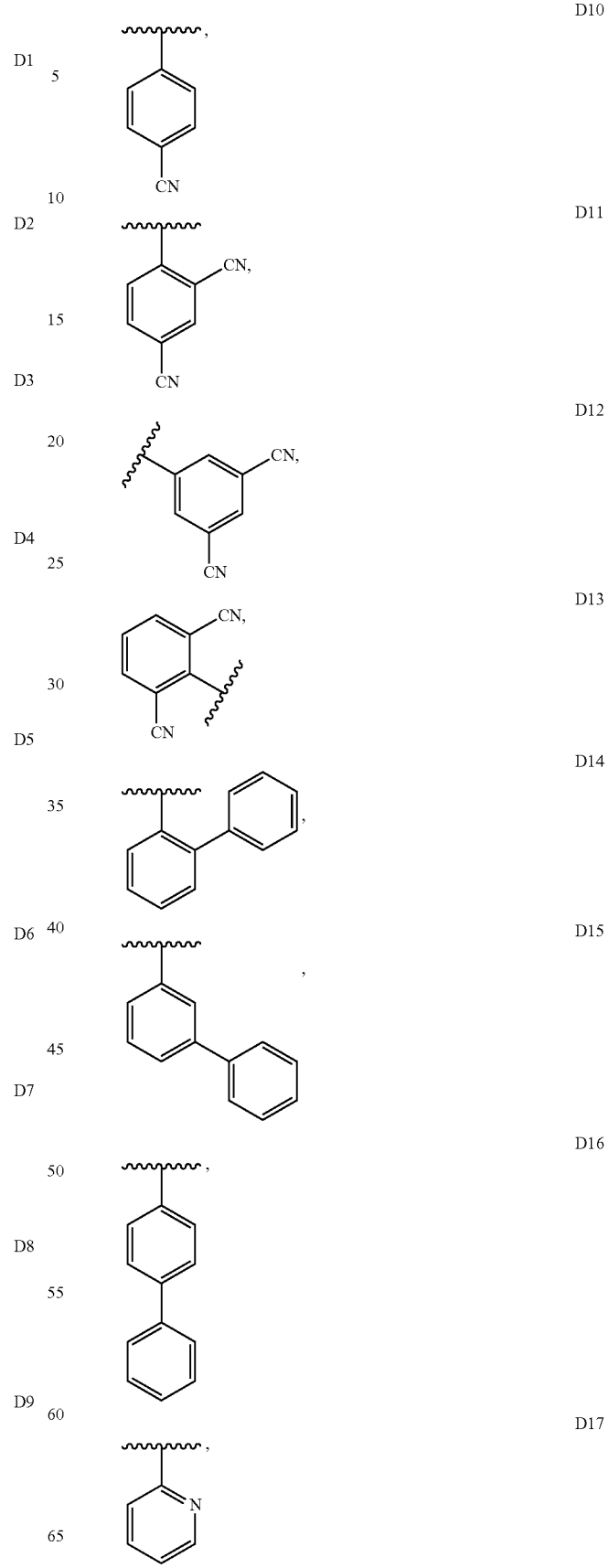

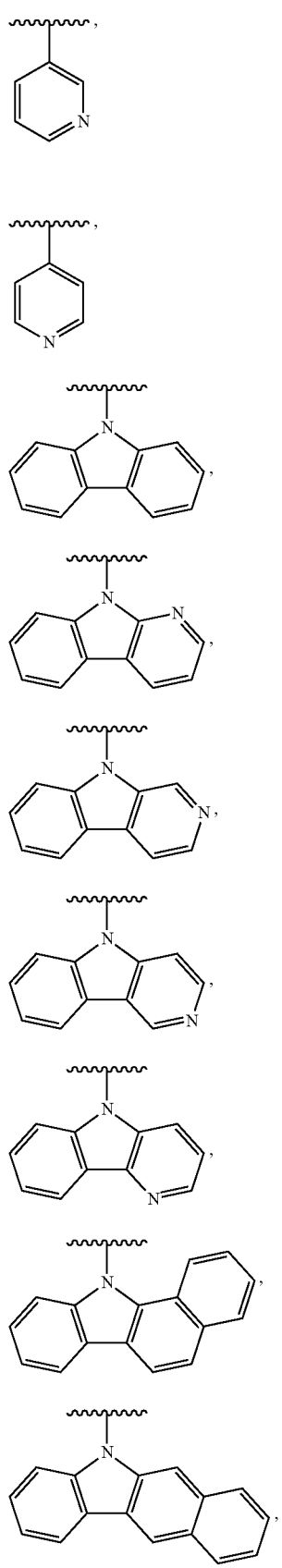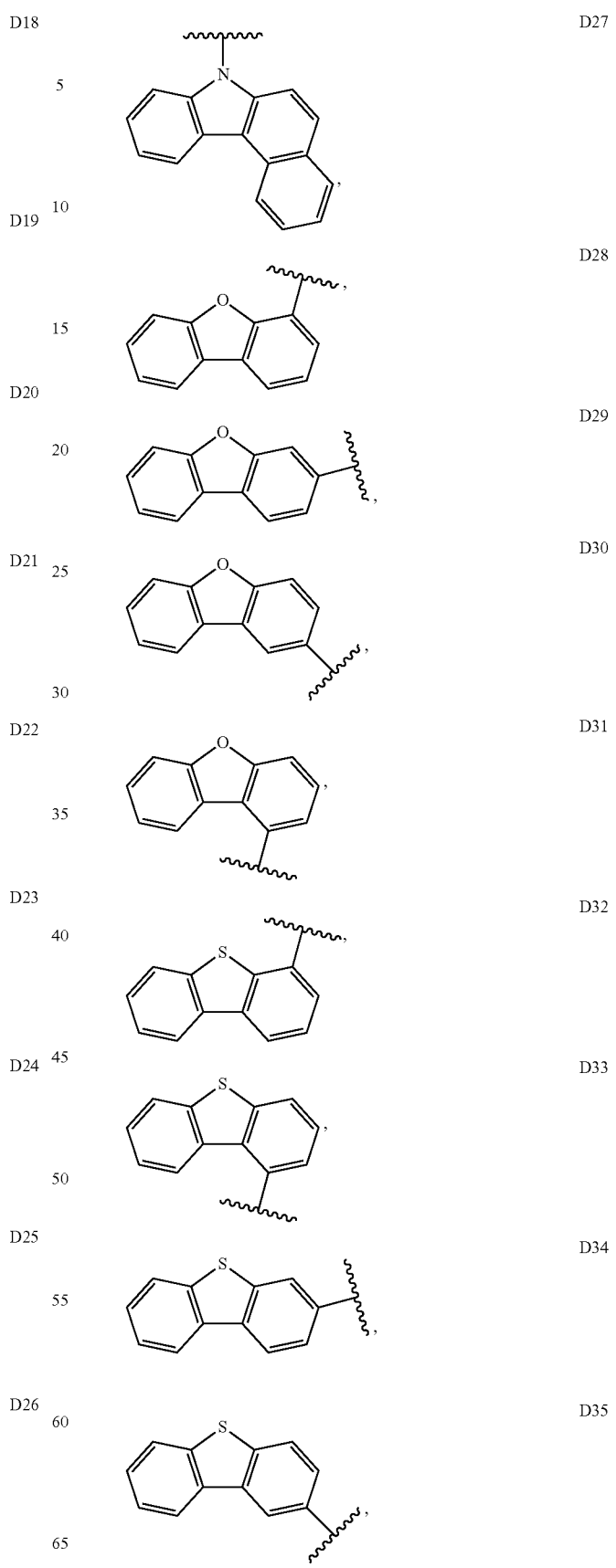

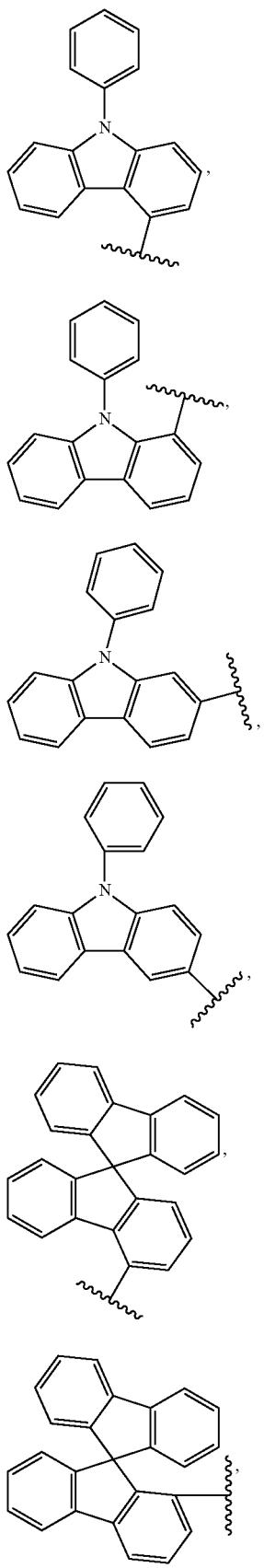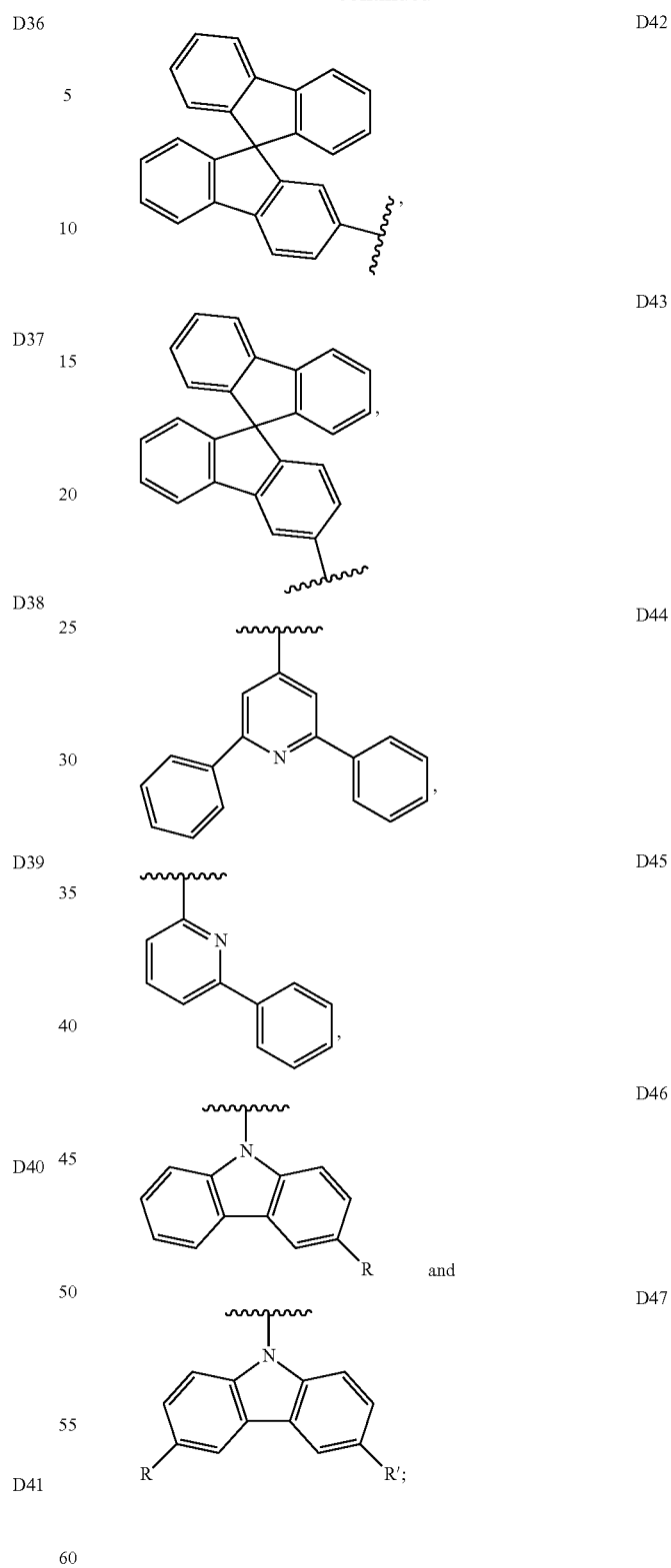
R and R' are independently selected from F, CN, CF$_3$, Me, and t-butyl.

In some embodiments, the present disclosure provides compounds of Formula (II):
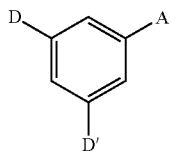
(II)
wherein
A is selected from
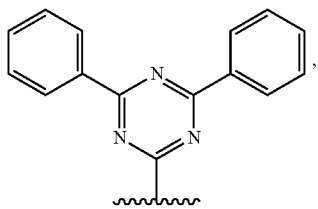
A1
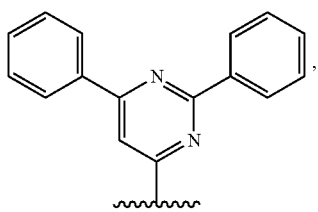
A2
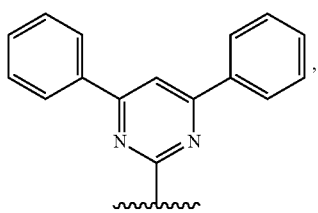
A3
, and
A4
;
A5
D and D' are independently
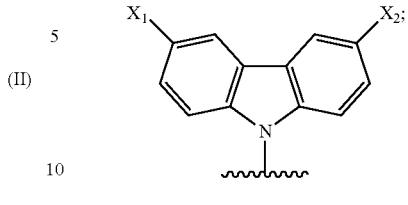
$X_1$ and $X_2$ are independently selected from Ar and R;
Ar is independently selected from
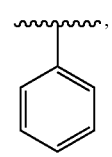
Ar1
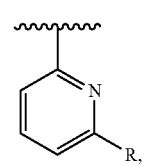
Ar2
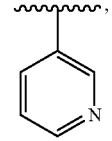
Ar3
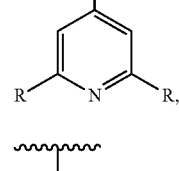
Ar4
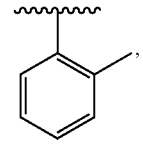
Ar5
Ar6
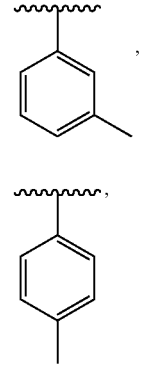
Ar7

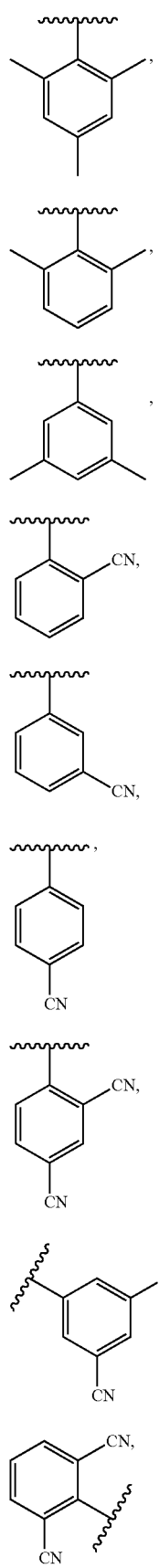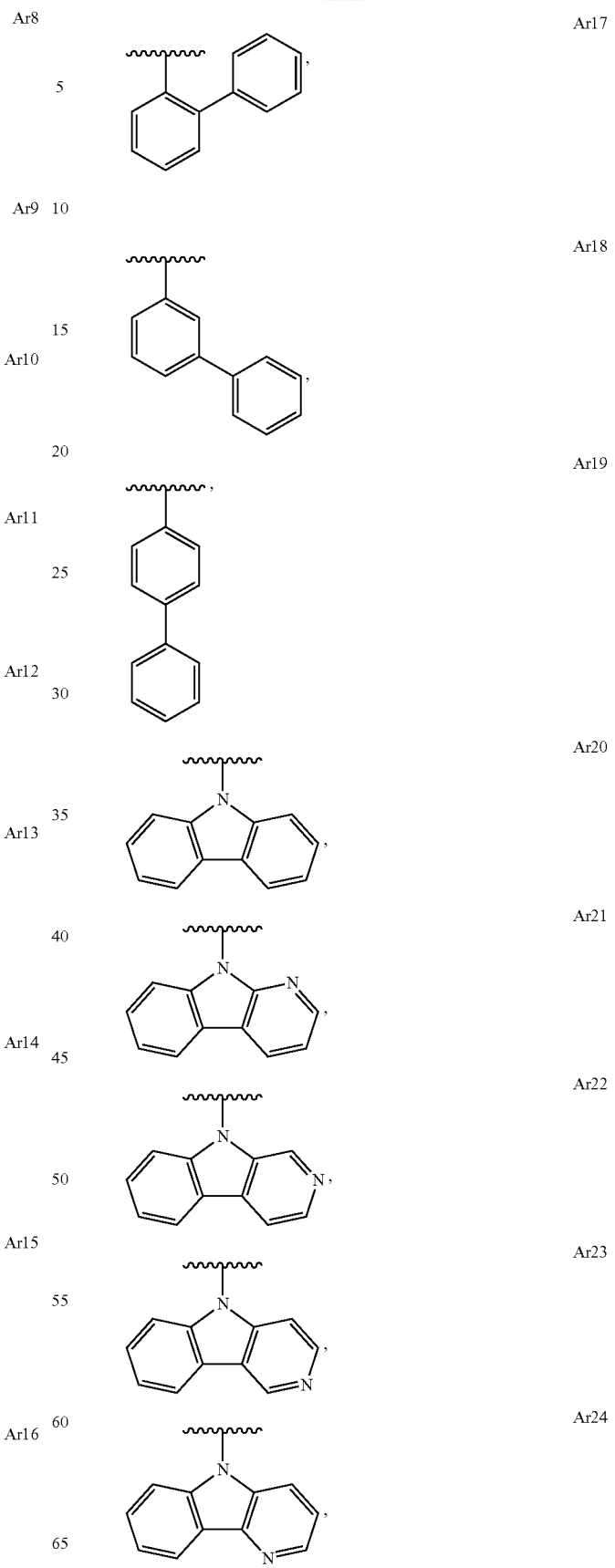

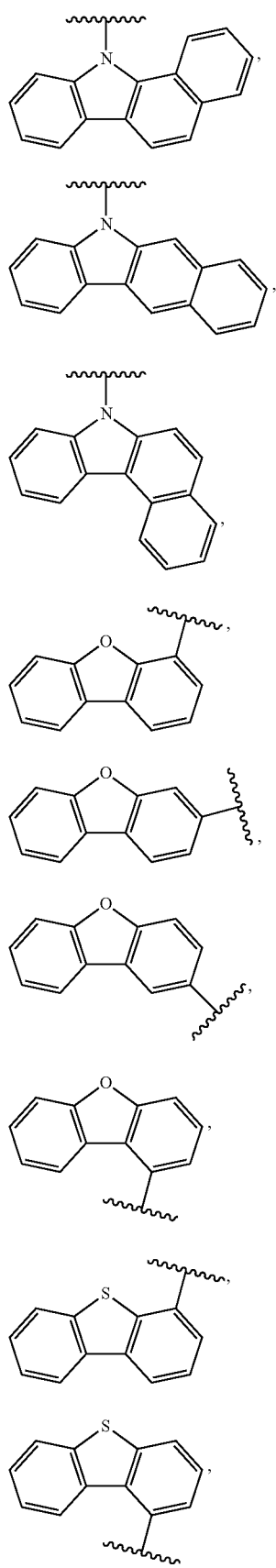
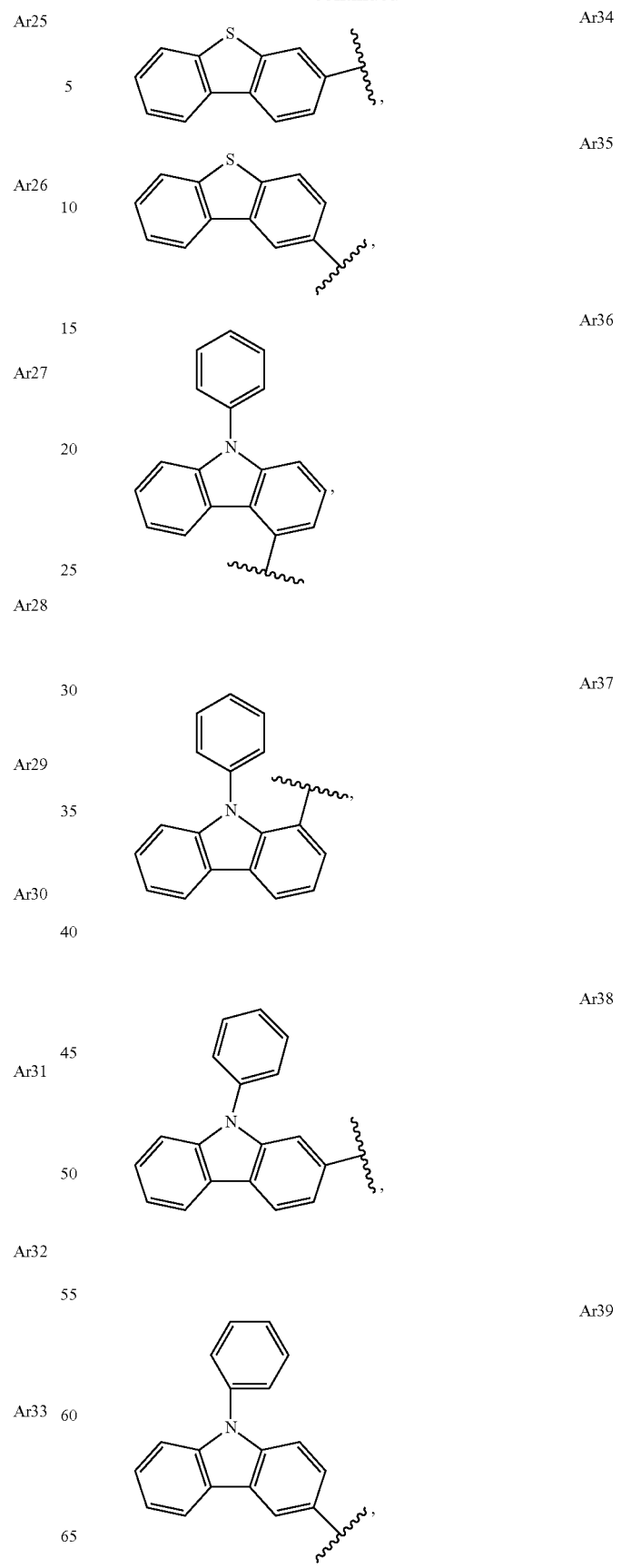

Ar40

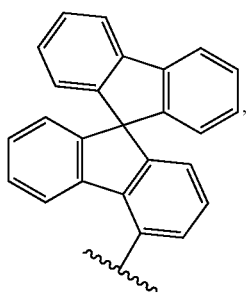

Ar41

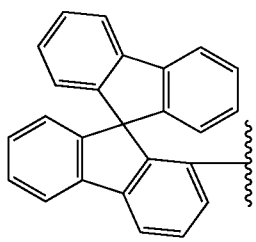

Ar42

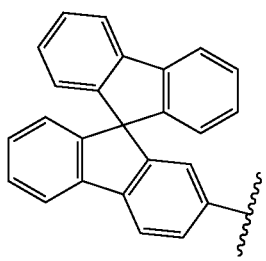 and

Ar43

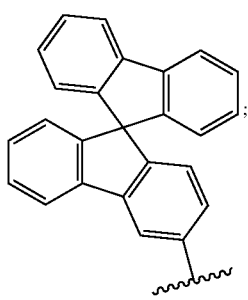 ;

R is independently selected from H, deuterium, F, CN, CF$_3$, Me, i-propyl, t-butyl, SiMe$_3$, and SiPh$_3$.

In some embodiments, the present disclosure provides light-emitting materials comprising compounds of Formula (I) or (II).

In some embodiments, the present disclosure provides delayed fluorescent emitters comprising the compound of Formula (I) or (II).

In some embodiments, the present disclosure provides organic light-emitting diodes (OLED) comprising compounds of Formula (I) or (II).

In some embodiments, provided herein is an organic light-emitting diode (OLED) comprising an anode, a cathode, and at least one organic layer comprising a light-emitting layer between the anode and the cathode, wherein the light-emitting layer comprises:

a host material; and a compound of Formula (I) or (II).

In some embodiments, provided herein is an organic light-emitting diode (OLED) comprising an anode, a cathode, and at least one organic layer comprising a light-emitting layer between the anode and the cathode, wherein the light-emitting layer comprises:

a host material; and a compound of Formula (I) or (II);

wherein the compound of Formula (I) or (II) is a light-emitting material.

In some embodiments, provided herein is an organic light-emitting diode (OLED) comprising an anode, a cathode, and at least one organic layer comprising a light-emitting layer between the anode and the cathode, wherein the light-emitting layer comprises:

a host material;

a compound of Formula (I) or (II); and a light-emitting material which is not a compound of Formula (I) or (II).

In some embodiments, provided herein is an organic light-emitting diode (OLED) comprising an anode, a cathode, and at least one organic layer comprising a light-emitting layer between the anode and the cathode, wherein the light-emitting layer comprises:

a compound of Formula (I) or (II); and a light-emitting material which is not a compound of Formula (I) or (II).

In some embodiments, the compounds of Formula (I) or (II) are used in a screen or a display.

In yet another aspect, the present disclosure relates to a method of manufacturing an OLED display, the method comprising:

forming a barrier layer on a base substrate of a mother panel;

forming a plurality of display units in units of cell panels on the barrier layer;

forming an encapsulation layer on each of the display units of the cell panels; and applying an organic film to an interface portion between the cell panels.

BRIEF DESCRIPTION OF THE DRAWINGS

The FIGURE is a schematic wherein 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

DETAILED DESCRIPTION

In one aspect, the present disclosure provides compounds of Formula (I):

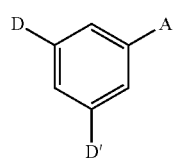

(I)

wherein
A is selected from
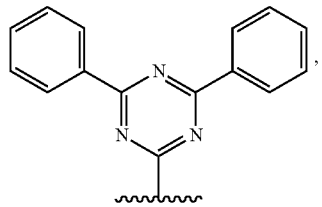 A1
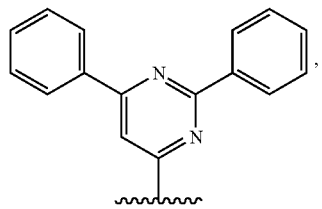 A2
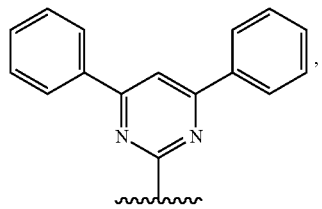 A3
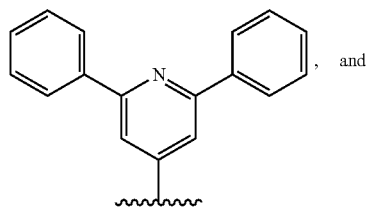 A4
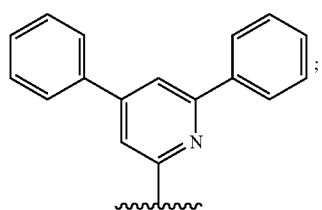 A5
D and D' are independently selected from
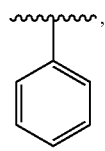 D1
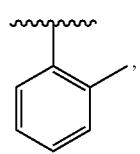 D2
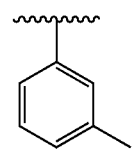 D3
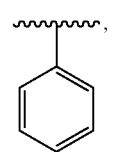 D4
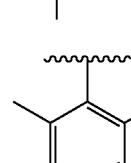 D5
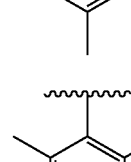 D6
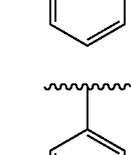 D7
D8
D9
D10
D11

-continued
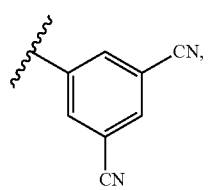
D12
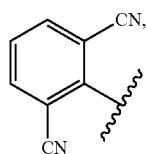
D13
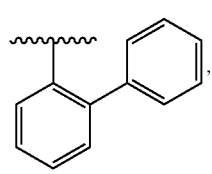
D14
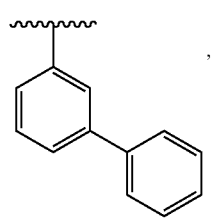
D15
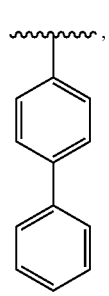
D16
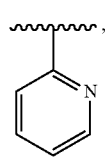
D17
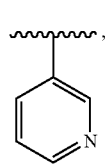
D18
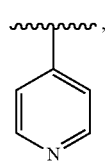
D19
-continued
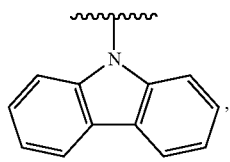
D20
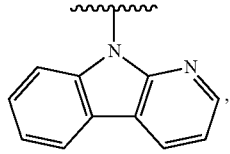
D21
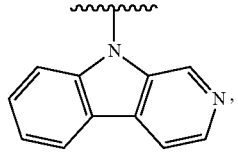
D22
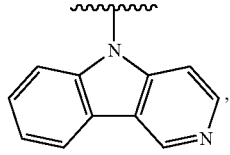
D23
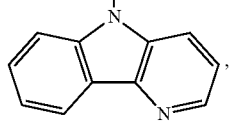
D24
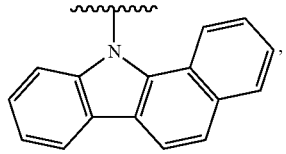
D25
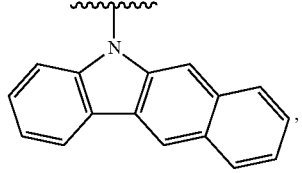
D26
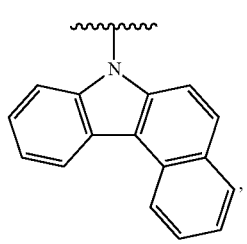
D27
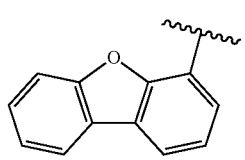
D28

-continued
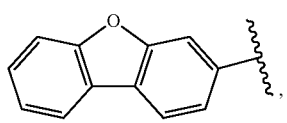 D29
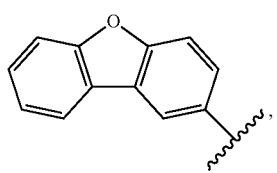 D30
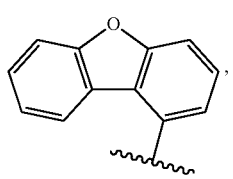 D31
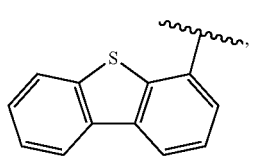 D32
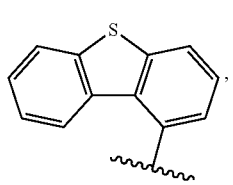 D33
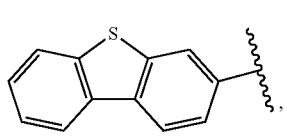 D34
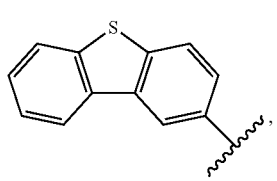 D35
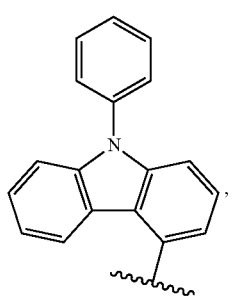 D36
-continued
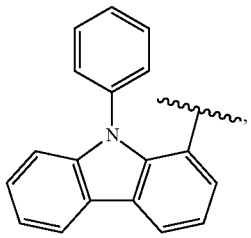 D37
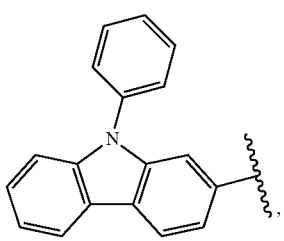 D38
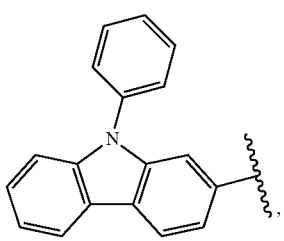 D39
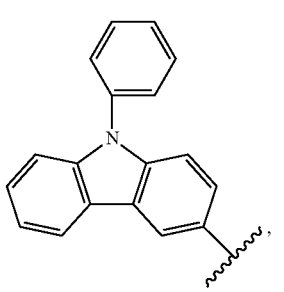 D40
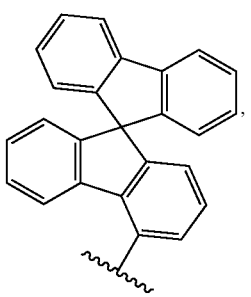 D41
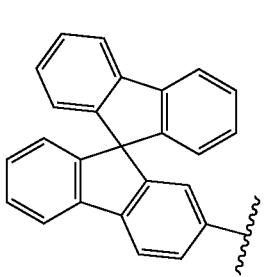 D42

-continued
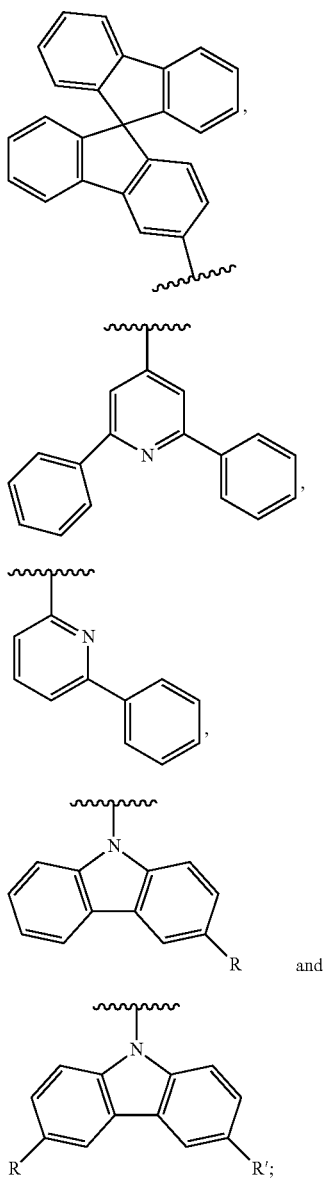
and
R and R' are independently selected from F, CN, CF$_3$, Me, and t-butyl.
In one aspect, the present disclosures provides compounds of Formula (II):
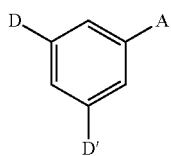
(II)
wherein
A is selected from
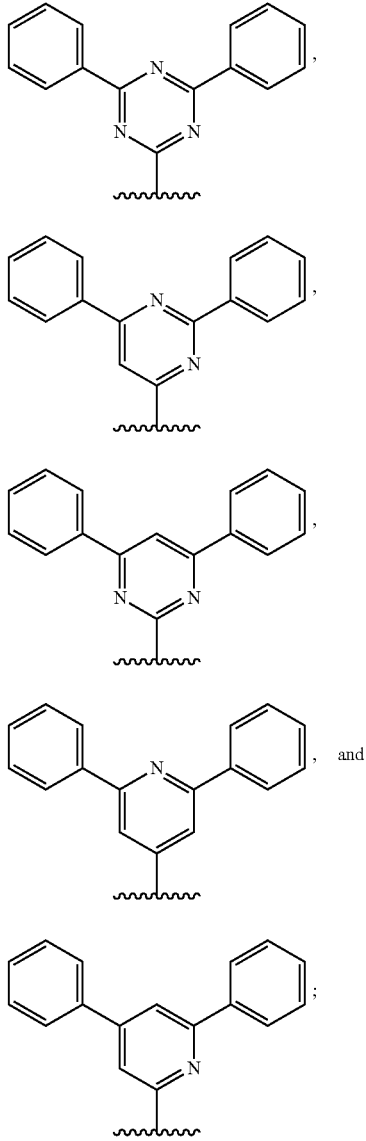
D and D' are independently $X_1$ and $X_2$ are independently selected from Ar and R;
Ar is independently selected from
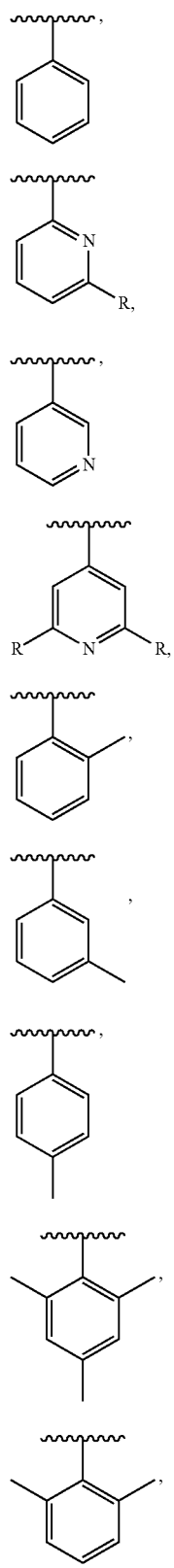
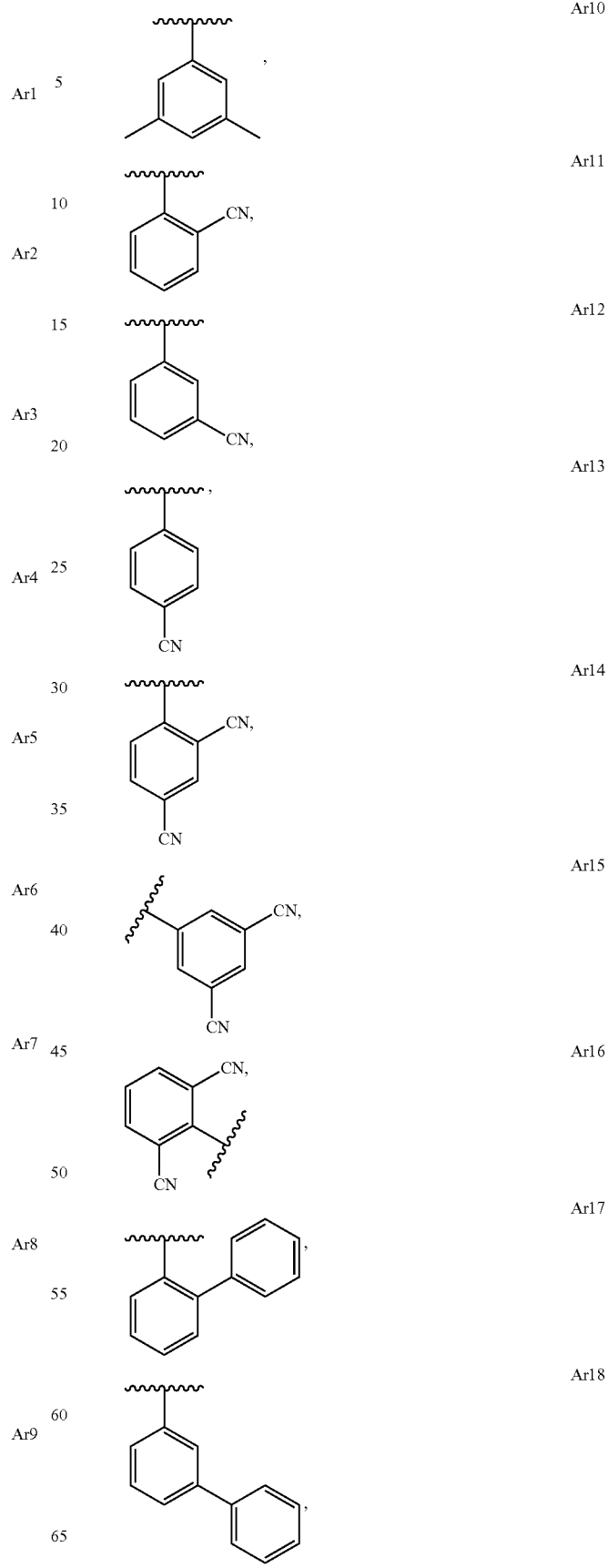

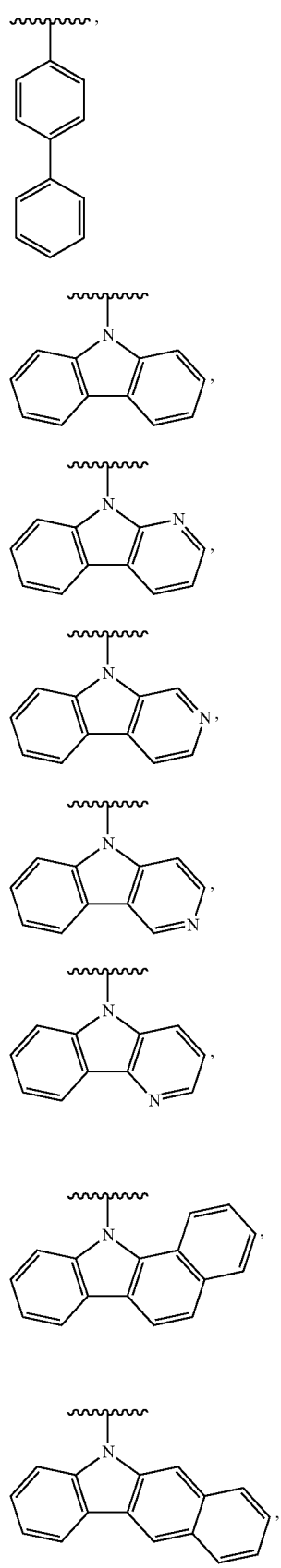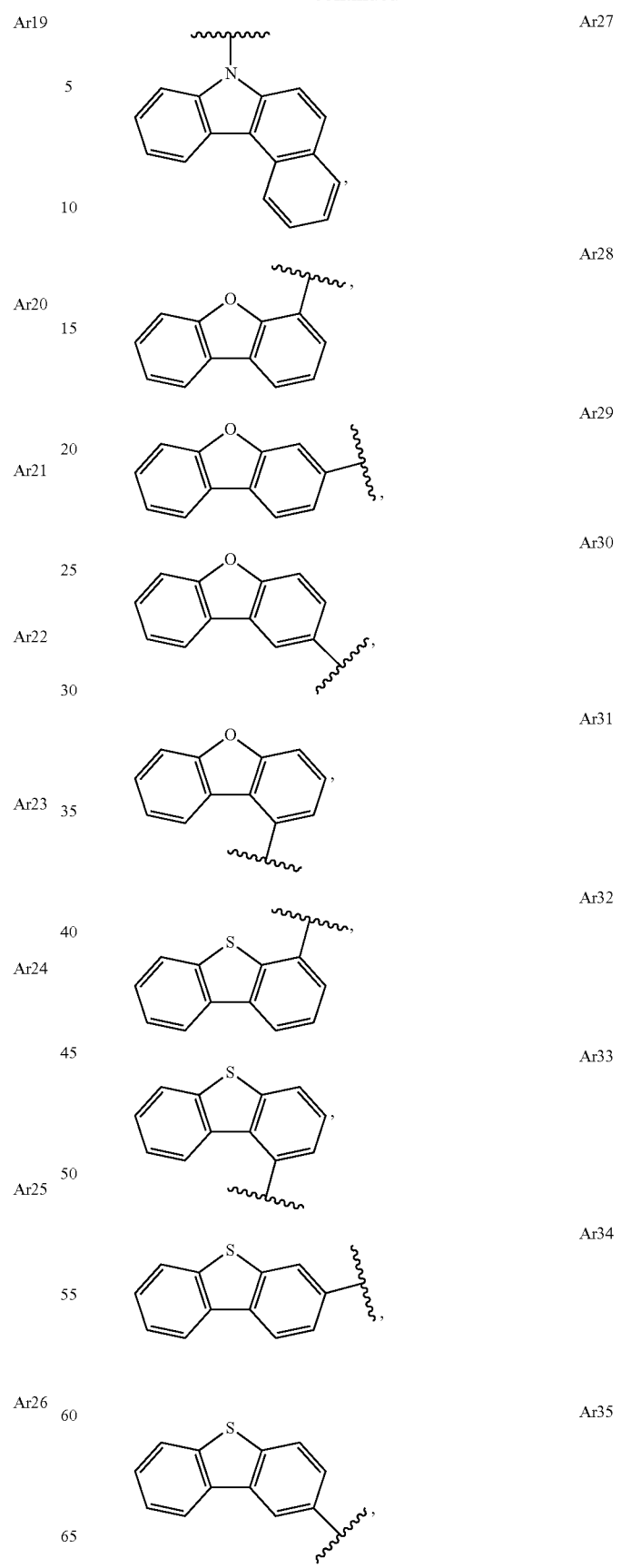

-continued

Ar36

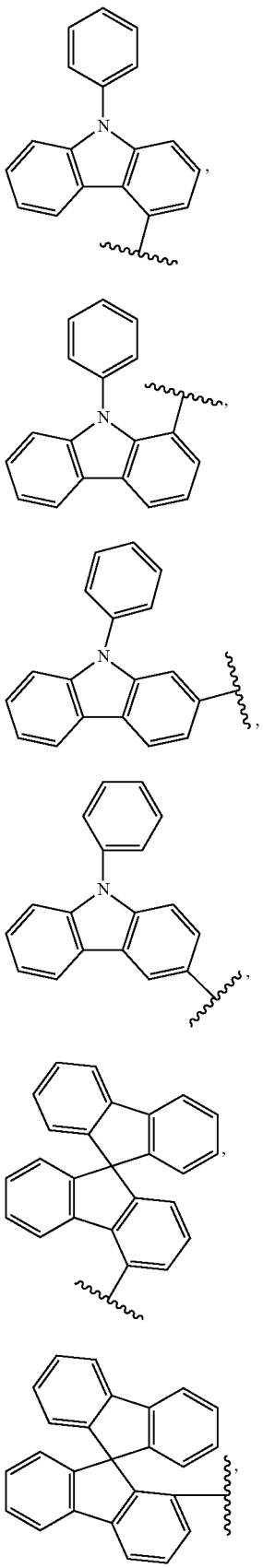

Ar37

Ar38

Ar39

Ar40

Ar41

-continued

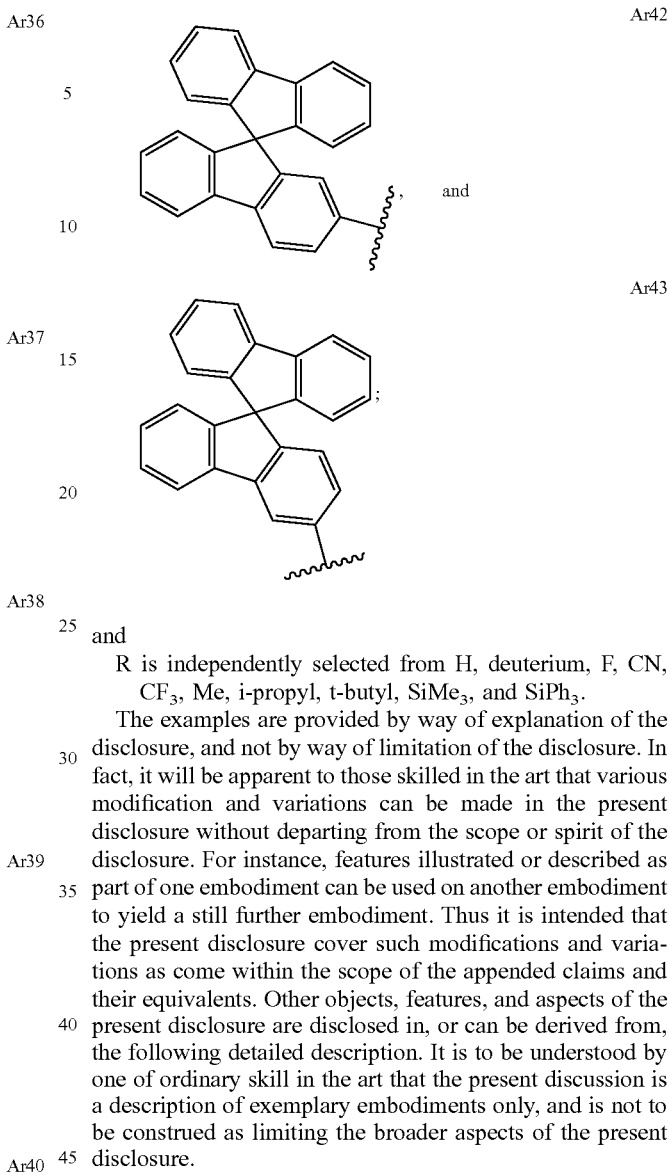

Ar42

, and

Ar43

;

and

R is independently selected from H, deuterium, F, CN, CF$_3$, Me, i-propyl, t-butyl, SiMe$_3$, and SiPh$_3$.

The examples are provided by way of explanation of the disclosure, and not by way of limitation of the disclosure. In fact, it will be apparent to those skilled in the art that various modification and variations can be made in the present disclosure without departing from the scope or spirit of the disclosure. For instance, features illustrated or described as part of one embodiment can be used on another embodiment to yield a still further embodiment. Thus it is intended that the present disclosure cover such modifications and variations as come within the scope of the appended claims and their equivalents. Other objects, features, and aspects of the present disclosure are disclosed in, or can be derived from, the following detailed description. It is to be understood by one of ordinary skill in the art that the present discussion is a description of exemplary embodiments only, and is not to be construed as limiting the broader aspects of the present disclosure.

Definitions

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

The term "acyl" is art-recognized and refers to a group represented by the general Formula hydrocarbylC(O)—, preferably alkylC(O)—.

The term "acylamino" is art-recognized and refers to an amino group substituted with an acyl group and may be represented, for example, by the Formula hydrocarbylC(O)NH—.

The term "acyloxy" is art-recognized and refers to a group represented by the general Formula hydrocarbylC(O)O—, preferably alkylC(O)O—.

The term "alkoxy" refers to an alkyl group, having an oxygen attached thereto. In some embodiments, an alkoxy has 1-20 carbon. In some embodiments, an alkoxy has 1-12 carbon atoms. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general Formula alkyl-O-alkyl.

The term "alkenyl", as used herein, refers to an aliphatic group comprising at least one double bond and is intended to include both "unsubstituted alkenyls" and "substituted alkenyls", the latter of which refers to alkenyl moieties having substituents replacing a hydrogen on one or more carbons of the alkenyl group. Typically, a straight chained or branched alkenyl group has from 1 to about 20 carbon atoms, preferably from 1 to about 12 unless otherwise defined. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 12 unless otherwise defined. In some embodiments, the alkyl group has from 1 to 8 carbon atoms, from 1 to 6 carbon atoms, from 1 to 4 carbon atoms, or from 1 to 3 carbon atoms. Examples of straight chained and branched alkyl groups include methyl, ethyl, n-propyl, iso-propyl, n-butyl, sec-butyl, tert-butyl, pentyl, hexyl, pentyl and octyl.

Moreover, the term "alkyl" as used throughout the specification, examples, and claims is intended to include both "unsubstituted alkyls" and "substituted alkyls", the latter of which refers to alkyl moieties having substituents replacing a hydrogen on one or more substitutable carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "arylthio", as used herein, refers to a thiol group substituted with an aryl group and may be represented by the general formula arylS—.

The term "alkynyl", as used herein, refers to an aliphatic group comprising at least one triple bond and is intended to include both "unsubstituted alkynyls" and "substituted alkynyls", the latter of which refers to alkynyl moieties having substituents replacing a hydrogen on one or more carbons of the alkynyl group. Typically, a straight chained or branched alkynyl group has from 1 to about 20 carbon atoms, preferably from 1 to about 10 unless otherwise defined. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

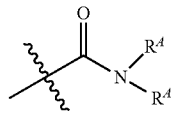

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

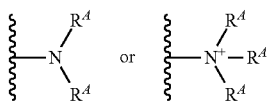

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 20-membered ring, more preferably a 6-membered ring. Preferably an aryl has 6-40 carbon atoms, more preferably has 6-25 carbon atoms. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

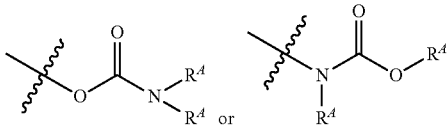

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. Preferably, a carbocylic group has from 3 to 20 carbon atoms. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl (Ph), may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Preferably, a cycloalkyl group has from 3 to 20 carbon atoms. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon comprising one or more double bonds.

The term "carbocyclylalkyl", as used herein, refers to an alkyl group substituted with a carbocycle group.

The term "carbonate", as used herein, refers to a group —OCO$_2$—R$^A$, wherein R$^A$ represents a hydrocarbyl group.

The term "carboxy", as used herein, refers to a group represented by the Formula —CO$_2$H.

The term "ester", as used herein, refers to a group —C(O)OR$^A$ wherein R$^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general Formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 20-membered rings, more preferably 5- to 6-membered rings, whose ring structures include at least one heteroatom, preferably one to four heteroatoms, more preferably one or two heteroatoms. Preferably a heteroaryl has 2-40 carbon atoms, more preferably has 2-25 carbon atoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, and carbazole, and the like.

The term "aryloxy" refers to an aryl group, having an oxygen attached thereto. Preferably an aryloxy has 6-40 carbon atoms, more preferably has 6-25 carbon atoms.

The term "heteroaryloxy" refers to an aryl group, having an oxygen attached thereto. Preferably a heteroaryloxy has 3-40 carbon atoms, more preferably has 3-25 carbon atoms.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 20-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom, wherein that carbon atom does not have a =O or =S substituent. Hydrocarbyls may optionally include heteroatoms. Hydrocarbyl groups include, but are not limited to, alkyl, alkenyl, alkynyl, alkoxyalkyl, aminoalkyl, aralkyl, aryl, aralkyl, carbocyclyl, cycloalkyl, carbocyclylalkyl, heteroaralkyl, heteroaryl groups bonded through a carbon atom, heterocyclyl groups bonded through a carbon atom, heterocyclylakyl, or hydroxyalkyl. Thus, groups like methyl, ethoxyethyl, 2-pyridyl, and trifluoromethyl are hydrocarbyl groups, but substituents such as acetyl (which has a =O substituent on the linking carbon) and ethoxy (which is linked through oxygen, not carbon) are not.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are six or fewer non-hydrogen atoms in the substituent. A "lower alkyl", for example, refers to an alkyl group that contains six or fewer carbon atoms. In some embodiments, the alkyl group has from 1 to 6 carbon atoms, from 1 to 4 carbon atoms, or from 1 to 3 carbon atoms. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

In the phrase "poly(meta-phenylene oxides)", the term "phenylene" refers inclusively to 6-membered aryl or 6-membered heteroaryl moieties. Exemplary poly(meta-phenylene oxides) are described in the first through twentieth aspects of the present disclosure.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Moieties that may be substituted can include any appropriate substituents described herein, for example, acyl, acylamino, acyloxy, alkoxy, alkoxyalkyl, alkenyl, alkyl, alkylamino, alkylthio, arylthio, alkynyl, amide, amino, aminoalkyl, aralkyl, carbamate, carbocyclyl, cycloalkyl, carbocyclylalkyl, carbonate, ester, ether, heteroaralkyl, heterocyclyl, heterocyclylalkyl, hydrocarbyl, silyl, sulfone, or thioether. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfonate" is art-recognized and refers to the group $SO_3H$, or a pharmaceutically acceptable salt thereof.

The term "sulfone" is art-recognized and refers to the group $—S(O)_2—R^A$, wherein $R^A$ represents a hydrocarbyl.

The term "thioether", as used herein, is equivalent to an ether, wherein the oxygen is replaced with a sulfur.

The term "symmetrical molecule," as used herein, refers to molecules that are group symmetric or synthetic symmetric. The term "group symmetric," as used herein, refers to molecules that have symmetry according to the group theory of molecular symmetry. The term "synthetic symmetric," as used herein, refers to molecules that are selected such that no regioselective synthetic strategy is required.

The term "donor," as used herein, refers to a molecular fragment that can be used in organic light-emitting diodes and is likely to donate electrons from its highest occupied molecular orbital to an acceptor upon excitation. In preferred embodiments, donors contain substituted amino groups. In an example embodiment, donors have an ionization potential greater than or equal to −6.5 eV.

The term "acceptor," as used herein, refers to a molecular fragment that can be used in organic light-emitting diodes and is likely to accept electrons into its lowest unoccupied molecular orbital from a donor that has been subject to excitation. In an example embodiment, acceptors have an electron affinity less than or equal to −0.5 eV.

The term "linker," or "bridge," as used herein, refers to a molecular fragment that can be included in a molecule which is covalently linked between acceptor and donor moieties. The linker can, for example, be further conjugated to the acceptor moiety, the donor moiety, or both. Without being bound to any particular theory, it is believed that the linker moiety can sterically restrict the acceptor and donor moieties into a specific configuration, thereby preventing the overlap between the conjugated a system of donor and acceptor moieties. Examples of suitable linker moieties include phenyl, ethenyl, and ethynyl.

The term "multivalent," as used herein, refers to a molecular fragment that is connected to at least two other molecular fragments. For example, a linker moiety, is multivalent.

" ~~~ " or "*" as used herein, refers to a point of attachment between two atoms.

"Hole transport layer (HTL)" and like terms mean a layer made from a material which transports holes. High hole mobility is recommended. The HTL is used to help block passage of electrons transported by the emitting layer. Low electron affinity is typically required to block electrons. The HTL should desirably have larger triplets to block exciton migrations from an adjacent emisse layer (EML). Examples of HTL compounds include, but are not limited to, di(p-tolyl)aminophenyl]cyclohexane (TAPC), N,N-diphenyl-N, N-bis(3-methylphenyl)-1,1-biphenyl-4,4-diamine (TPD), and N,N'-diphenyl-N,N'-bis(1-naphthyl)-(1,1'-biphenyl)-4, 4'-diamine (NPB, α-NPD).

"Emitting layer" and like terms mean a layer which emits light. In some embodiments, the emitting layer comprises host material and guest material. The guest material can also be referred to as a dopant material, but the disclosure is not limited there to. The host material or "host" could be bipolar or unipolar, and may be used alone or by combination of two or more host materials. The opto-electrical properties of the host material may differ to which type of guest material (TADF, Phosphorescent or Fluorescent) is used. For Fluorescent guest materials, the host materials should have good spectral overlap between absorption of the guest material and emission of the material to induce good Forster transfer to guest materials. For Phosphorescent guest materials, the host materials should have high triplet energy to confine triplets of the guest material. For TADF guest materials, the host materials should have both spectral overlap and higher triplet energy.

"Dopant" and like terms, refer to additive materials for carrier transporting layers, emitting layers or other layers. In carrier transporting layers, dopant and like terms perform as an electron acceptor or a donator that increases the conductivity of an organic layer of an organic electronic device, when added to the organic layer as an additive. Organic semiconductors may likewise be influenced, with regard to their electrical conductivity, by doping. Such organic semi-conducting matrix materials may be made up either of compounds with electron-donor properties or of compounds with electron-acceptor properties. In emitting layers, dopant and like terms also mean the light-emitting material which is dispersed in a matrix, for example, a host. When a triplet harvesting material is doped into an emitting layer or contained in an adjacent layer so as to improve exciton generation efficiency, it is named as assistant dopant. The content of the assistant dopant in the light-emitting layer or the adjacent layer is not particularly limited so as the triplet harvesting material improves the exciton generation efficiency. The content of the assistant dopant in the light-emitting layer is preferably higher than, more preferably at least twice than the light-emitting material. In the light-emitting layer, the content of the host material is preferably 50% by weight or more, the content of the assistant dopant is preferably from 5% by weight to less than 50% by weight, and the content of the light-emitting material is preferably more than 0% by weight to less than 25% by weight, more preferably from 0% by weight to less than 10% by weight. The content of the assistant dopant in the adjacent layer may be more than 50% by weight and may be 100% by weight. In the case where a device containing a triplet harvesting material in a light-emitting layer or an adjacent layer has a higher light emission efficiency than a device without the triplet harvesting material, such triplet harvesting material functions as an assistant dopant. A light-emitting layer containing a host material, an assistant dopant and a light-emitting material satisfies the following (A) and preferably satisfies the following (B):

$$ES1(A) > ES1(B) > ES1(C) \tag{A}$$

$$ET1(A) > ET1(B) \tag{B}$$

wherein ES1(A) represents a lowest excited singlet energy level of the host material; ES1(B) represents a lowest excited singlet energy level of the assistant dopant; ES1(C) represents a lowest excited singlet energy level of the light-emitting material; ET1(A) represents a lowest excited triplet energy level at 77 K of the host material; and ET1(B) represents a lowest excited triplet energy level at 77 K of the assistant dopant. The assistant dopant has an energy difference ΔEst between a lowest singlet excited state and a lowest triplet excited state at 77 K of preferably 0.3 eV or less, more preferably 0.2 eV or less, still more preferably 0.1 eV or less.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "deuterium", the position is understood to have deuterium at an abundance that is at least 3340 times greater than the natural abundance of deuterium, which is 0.015% (i.e., at least 50.1% incorporation of deuterium).

"d" refers to deuterium.

"Substituted with deuterium" refers to the replacement of one or more hydrogen atoms with a corresponding number of deuterium atoms.

The term "isotopic enrichment factor" as used herein means the ratio between the isotopic abundance and the natural abundance of a specified isotope.

In various embodiments, compounds of this invention have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90'/o deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

Principles of OLED

OLEDs are typically composed of a layer of organic materials or compounds between two electrodes, an anode and a cathode. The organic molecules are electrically conductive as a result of delocalization of π electronics caused by conjugation over part or all of the molecule. When voltage is applied, electrons from the highest occupied molecular orbital (HOMO) present at the anode flow into the lowest unoccupied molecular orbital (LUMO) of the organic molecules present at the cathode. Removal of electrons from the HOMO is also referred to as inserting electron holes into the HOMO. Electrostatic forces bring the electrons and the holes towards each other until they recombine and form an exciton (which is the bound state of the electron and the hole). As the excited state decays and the energy levels of the electrons relax, radiation having a frequency in the visible spectrum is emitted. The frequency of this radiation depends on the band gap of the material, which is the difference in energy between the HOMO and the LUMO.

As electrons and holes are fermions with half integer spin, an exciton may either be in a singlet state or a triplet state depending on how the spins of the electron and hole have been combined. Statistically, three triplet excitons will be formed for each singlet exciton. Decay from triplet states is spin forbidden, which results in increases in the timescale of the transition and limits the internal efficiency of fluorescent devices. Phosphorescent organic light-emitting diodes make use of spin-orbit interactions to facilitate intersystem crossing between singlet and triplet states, thus obtaining emission from both singlet and triplet states and improving the internal efficiency.

One prototypical phosphorescent material is iridium tris (2-phenylpyridine) (Ir(ppy)$_3$) in which the excited state is a charge transfer from the Ir atom to the organic ligand. Such approaches have reduced the triplet lifetime to about several is, several orders of magnitude slower than the radiative lifetimes of fully-allowed transitions such as fluorescence. Ir-based phosphors have proven to be acceptable for many display applications, but losses due to large triplet densities still prevent the application of OLEDs to solid-state lighting at higher brightness.

TADF seeks to minimize $\Delta E_{ST}$. The reduction in exchange splitting from typical values of 0.4-0.7 eV to a gap of the order of the thermal energy (proportional to kBT, where kB represents the Boltzmann constant, and T represents temperature) means that thermal agitation can transfer population between singlet levels and triplet sublevels in a relevant timescale even if the coupling between states is small.

TADF molecules consist of donor and acceptor moieties connected directly by a covalent bond or via a conjugated linker (or "bridge"). A "donor" moiety is likely to transfer electrons from its HOMO upon excitation to the "acceptor" moiety. An "acceptor" moiety is likely to accept the electrons from the "donor" moiety into its LUMO. The donor-acceptor nature of TADF molecules results in low-lying excited states with charge-transfer character that exhibit very low $\Delta E_{ST}$. Since thermal molecular motions can randomly vary the optical properties of donor-acceptor systems, a rigid three-dimensional arrangement of donor and acceptor moieties can be used to limit the non-radiative decay of the charge-transfer state by internal conversion during the lifetime of the excitation.

It is beneficial, therefore, to decrease $\Delta E_{ST}$, and to create a system with increased reversed intersystem crossing (RISC) capable of exploiting triplet excitons. Such a system, it is believed, will result in increased quantum efficiency and decreased emission lifetimes. Systems with these features will be capable of emitting light without being subject to the rapid degradation prevalent in OLEDs known today.

Compounds of the Disclosure

In some embodiments, the compounds have a structure of Formula (I):

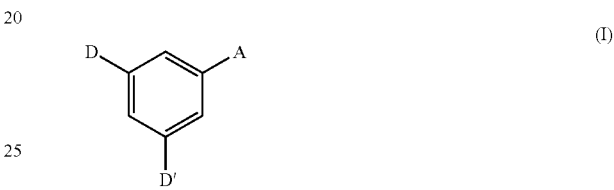

wherein

A is selected from

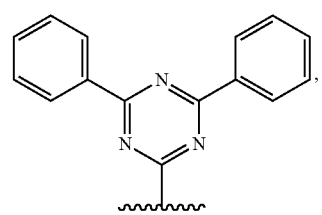

A1

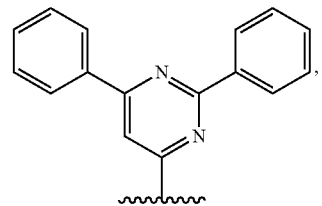

A2

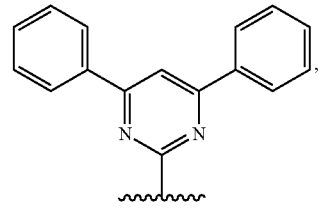

A3

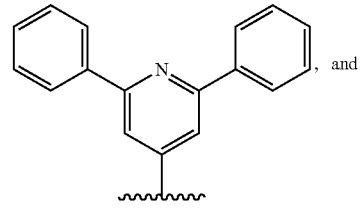

A4

, and

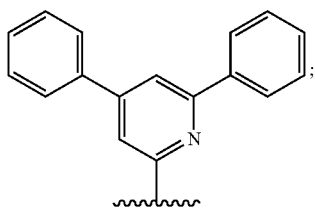
D and D' are independently selected from
A5 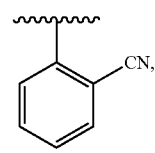 D8
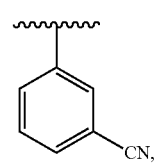 D9
D1 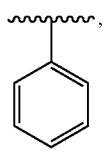
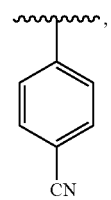 D10
D2 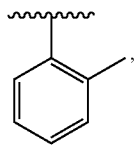
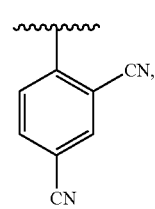 D11
D3 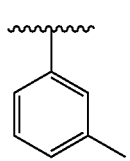
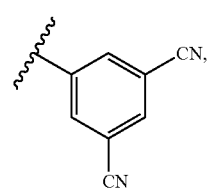 D12
D4 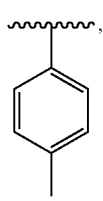
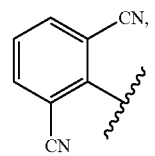 D13
D5 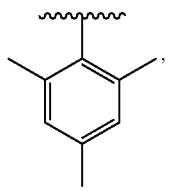
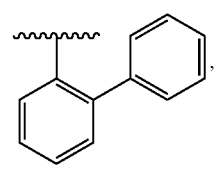 D14
D6 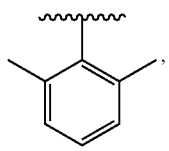
D15
D7 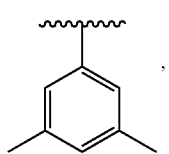

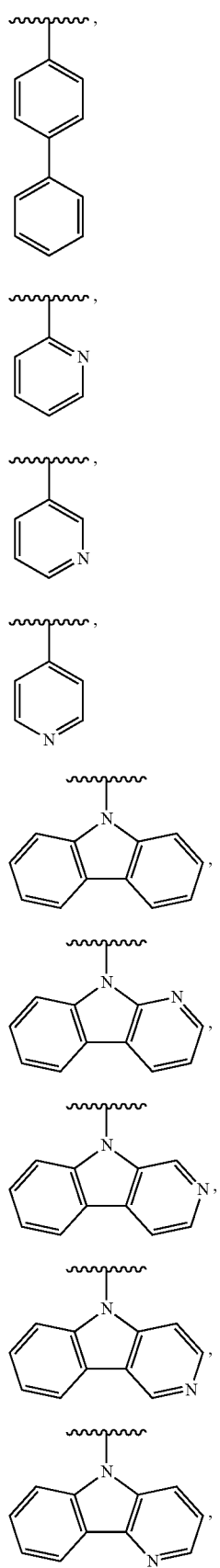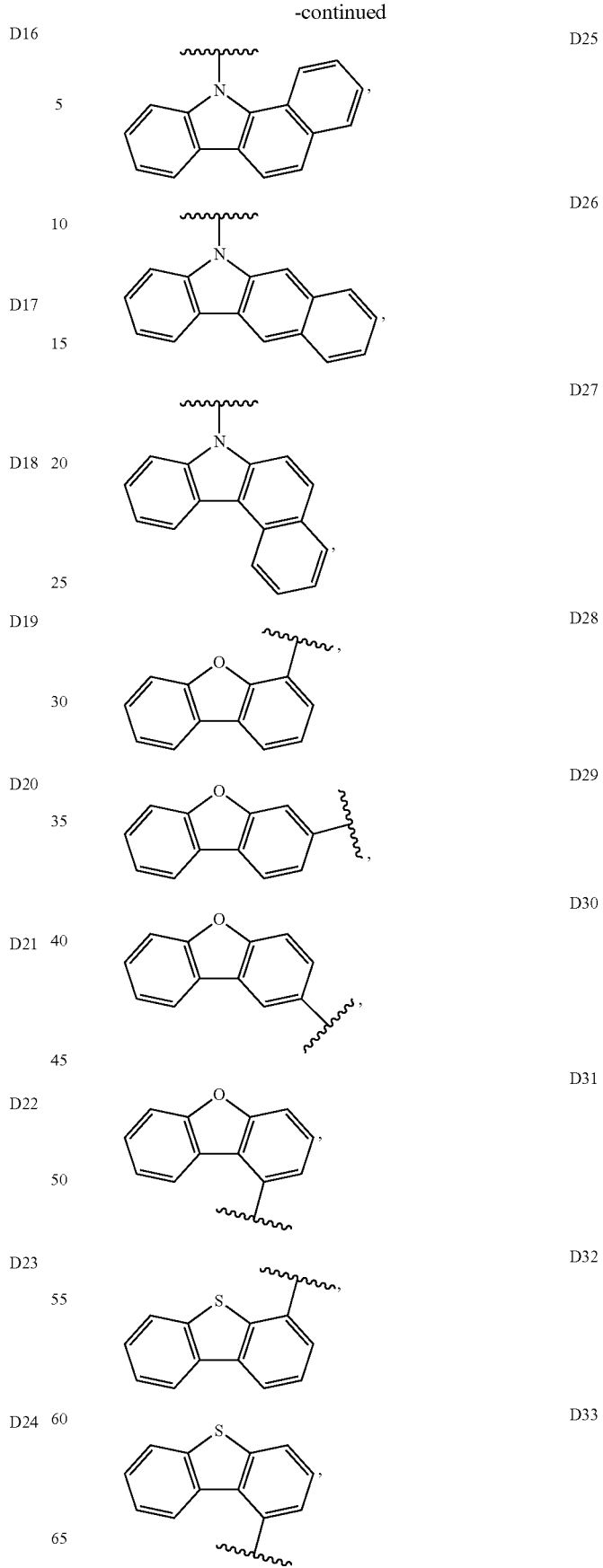

-continued
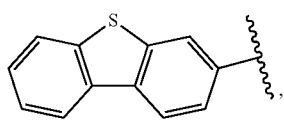,
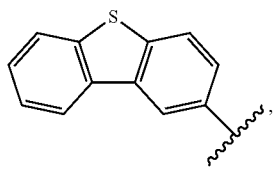,
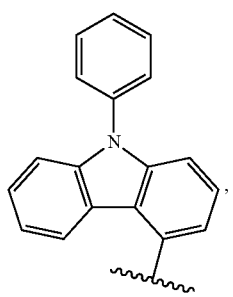,
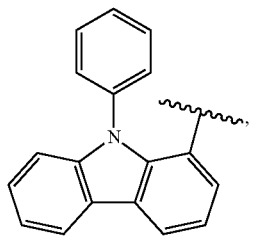,
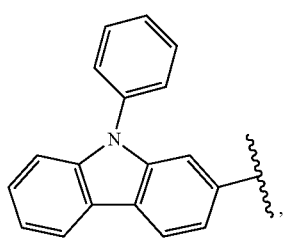,
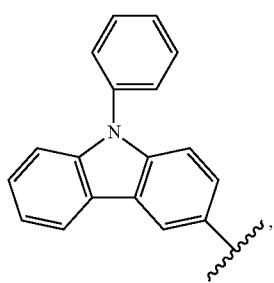,
-continued
D34
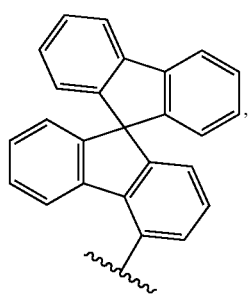,
D35
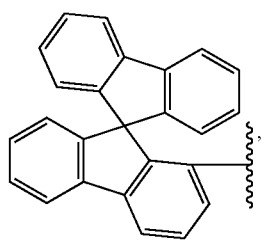,
D36
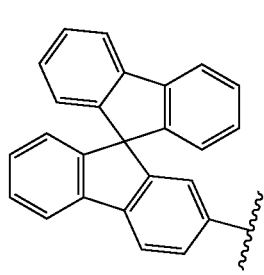
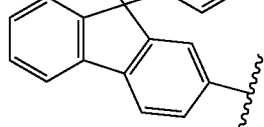,
D37
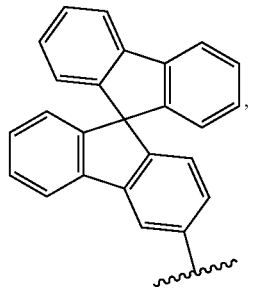,
D38
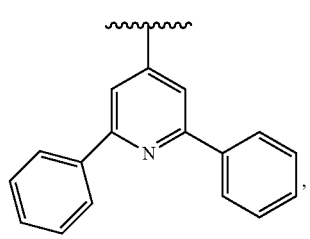,
D39
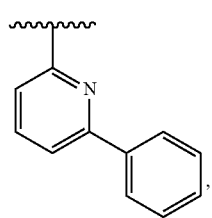,
D40
D41
D42
D43
D44
D45

-continued

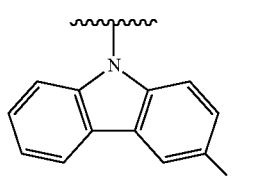
D46

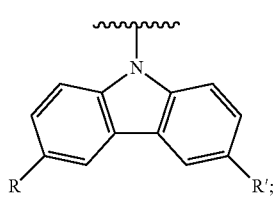
D47 and

R and R' are independently selected from F, CN, CF$_3$, Me, and t-butyl.

In some embodiments, A is A1. In some embodiments, A is A2. In some embodiments, A is A3. In some embodiments, A is A4. In some embodiments, A is A5. In some embodiments, A is A1 or A3.

In some embodiments, D is D1. In some embodiments, D is D2. In some embodiments, D is D3. In some embodiments, D is D4. In some embodiments, D is D5. In some embodiments, D is D6. In some embodiments, D is D7. In some embodiments, D is D8. In some embodiments, D is D9. In some embodiments, D is D10. In some embodiments, D is D11. In some embodiments, D is D12. In some embodiments, D is D13. In some embodiments, D is D14. In some embodiments, D is D15. In some embodiments, D is D16. In some embodiments, D is D17. In some embodiments, D is D18. In some embodiments, D is D19. In some embodiments, D is D20. In some embodiments, D is D21. In some embodiments, D is D22. In some embodiments, D is D23. In some embodiments, D is D24. In some embodiments, D is D25. In some embodiments, D is D26. In some embodiments, D is D27. In some embodiments, D is D28. In some embodiments, D is D29. In some embodiments, D is D30. In some embodiments, D is D31. In some embodiments, D is D32. In some embodiments, D is D33. In some embodiments, D is D34. In some embodiments, D is D35. In some embodiments, D is D36. In some embodiments, D is D37. In some embodiments, D is D38. In some embodiments, D is D39. In some embodiments, D is D40. In some embodiments, D is D41. In some embodiments, D is D42. In some embodiments, D is D43. In some embodiments, D is D44. In some embodiments, D is D45. In some embodiments, D is D46. In some embodiments, D is D47.

In some embodiments, D is selected from D1, D2, D3, D4, D5, D6, and D7. In some embodiments, D is selected from D8, D9, D10, D11, D12, and D13. In some embodiments, D is selected from D14, D15, and D16. In some embodiments, D is selected from D17, D18, and D19. In some embodiments, D is selected from D20, D21, D22, D23, and D24. In some embodiments, D is selected from D25, D26, and D27. In some embodiments, D is selected from D28, D29, D30, and D31. In some embodiments, D is selected from D32, D33, D34, and D35. In some embodiments, D is selected from D36, D37, D38, and D39. In some embodiments, D is selected from D40, D41, D42, and D43. In some embodiments, D is selected from D44 and D45. In some embodiments, D is selected from D46 and D47.

In some embodiments, D' is D1. In some embodiments, D' is D2. In some embodiments, D' is D3. In some embodiments, D' is D4. In some embodiments, D' is D5. In some embodiments, D' is D6. In some embodiments, D' is D7. In some embodiments, D' is D8. In some embodiments, D' is D9. In some embodiments, D' is D10. In some embodiments, D' is D11. In some embodiments, D' is D12. In some embodiments, D' is D13. In some embodiments, D' is D14. In some embodiments, D' is D15. In some embodiments, D' is D16. In some embodiments, D' is D17. In some embodiments, D' is D18. In some embodiments, D' is D19. In some embodiments, D' is D20. In some embodiments, D' is D21. In some embodiments, D' is D22. In some embodiments, D' is D23. In some embodiments, D' is D24. In some embodiments, D' is D25. In some embodiments, D' is D26. In some embodiments, D' is D27. In some embodiments, D' is D28. In some embodiments, D' is D29. In some embodiments, D' is D30. In some embodiments, D' is D31. In some embodiments, D' is D32. In some embodiments, D' is D33. In some embodiments, D' is D34. In some embodiments, D' is D35. In some embodiments, D' is D36. In some embodiments, D' is D37. In some embodiments, D' is D38. In some embodiments, D' is D39. In some embodiments, D' is D40. In some embodiments, D' is D41. In some embodiments, D' is D42. In some embodiments, D' is D43. In some embodiments, D' is D44. In some embodiments, D' is D45. In some embodiments, D' is D46. In some embodiments, D' is D47.

In some embodiments, D' is selected from D1, D2, D3, D4, D5, D6, and D7. In some embodiments, D' is selected from D8, D9, D10, D11, D12, and D13. In some embodiments, D' is selected from D14, D15, and D16. In some embodiments, D' is selected from D17, D18, and D19. In some embodiments, D' is selected from D20, D21, D22, D23, and D24. In some embodiments, D' is selected from D25, D26, and D27. In some embodiments, D' is selected from D28, D29, D30, and D31. In some embodiments, D' is selected from D32, D33, D34, and D35. In some embodiments, D' is selected from D36, D37, D38, and D39. In some embodiments, D' is selected from D40, D41, D42, and D43. In some embodiments, D' is selected from D44 and D45. In some embodiments, D' is selected from D46 and D47.

In some embodiments, R is F. In some embodiments, R is CN. In some embodiments, R is CF$_3$. In some embodiments, R is Me. In some embodiments, R is t-butyl.

In some embodiments, R' is F. In some embodiments, R' is CN. In some embodiments, R' is CF$_3$. In some embodiments, R' is Me. In some embodiments, R' is t-butyl.

In some embodiments, R and R' are the same. In some embodiments, R and R' are different.

In some embodiments, the compounds have a structure of Formula (II):

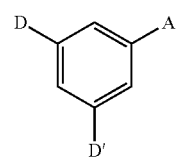
(II)

wherein
A is selected from
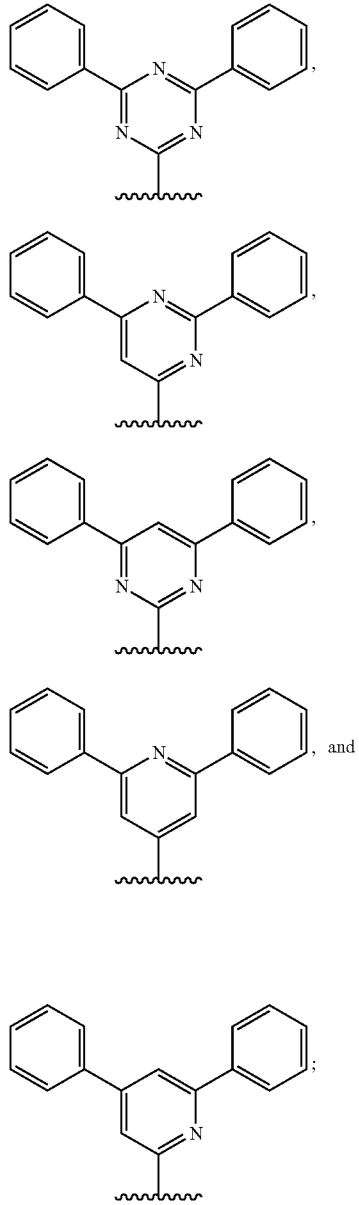
D and D' are independently
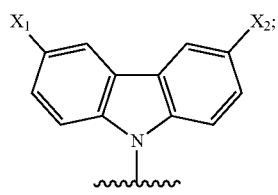
$X_1$ and $X_2$ are independently selected from Ar and R;
Ar is independently selected from
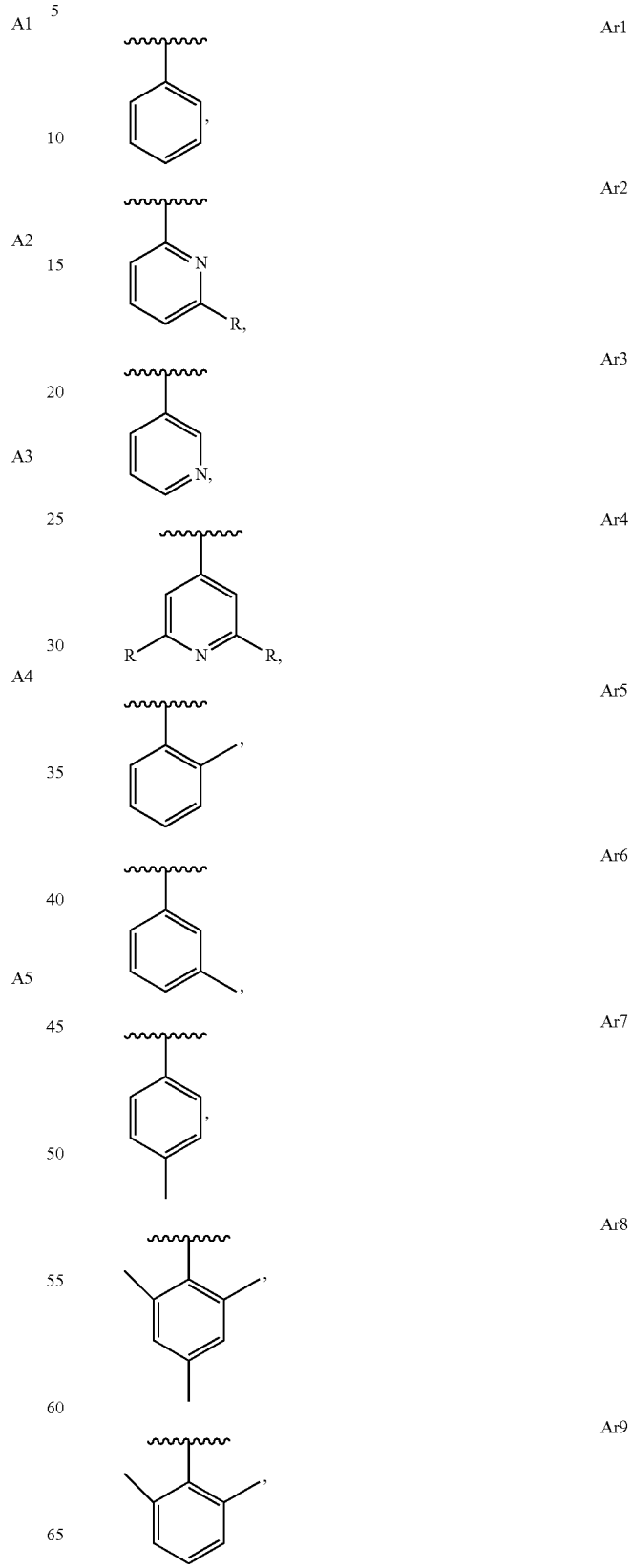

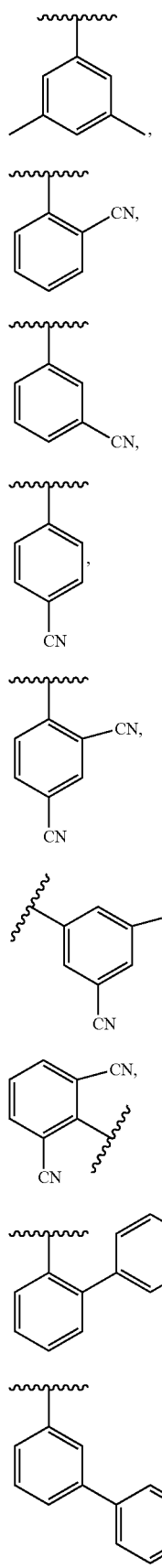
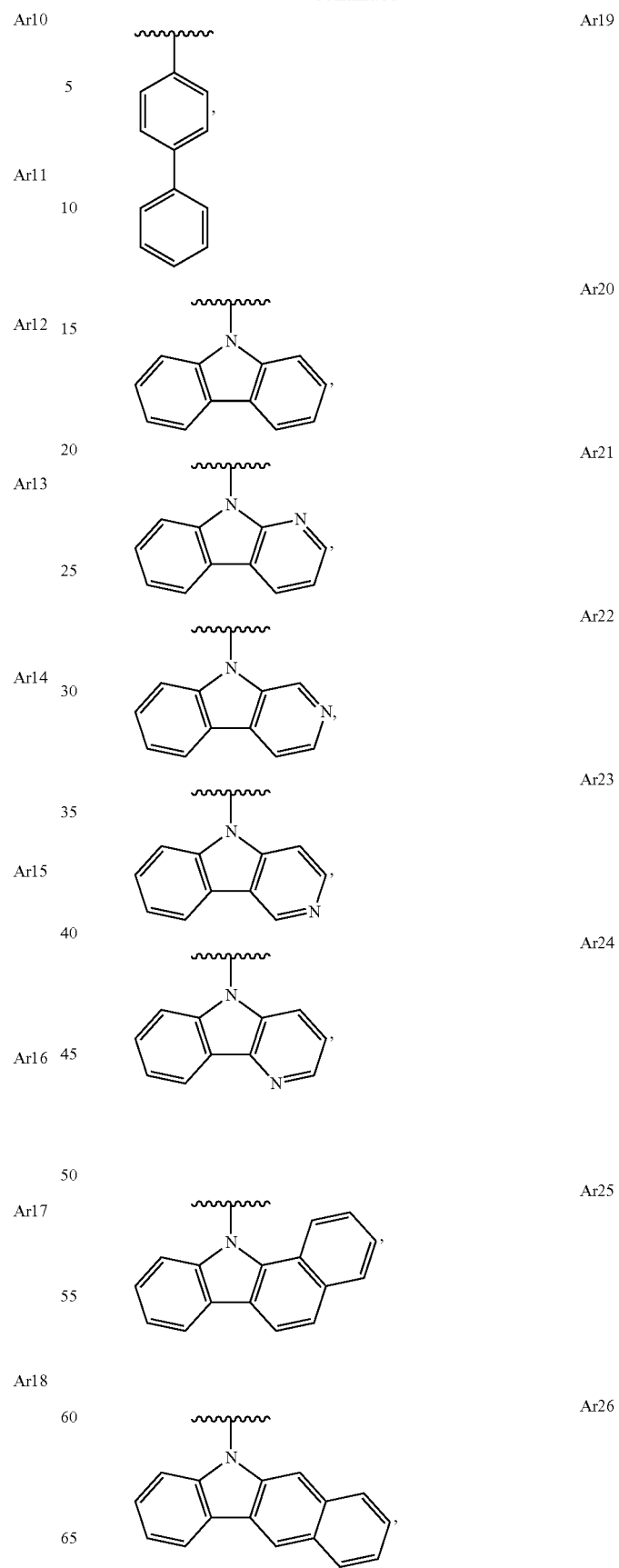

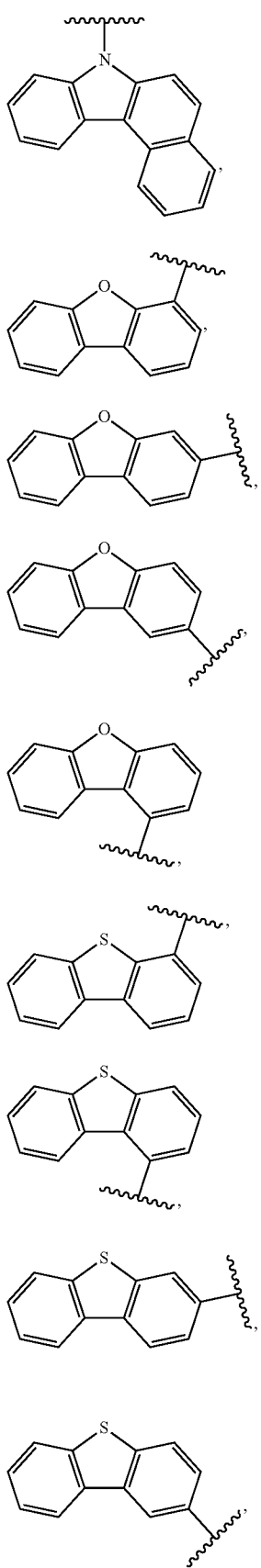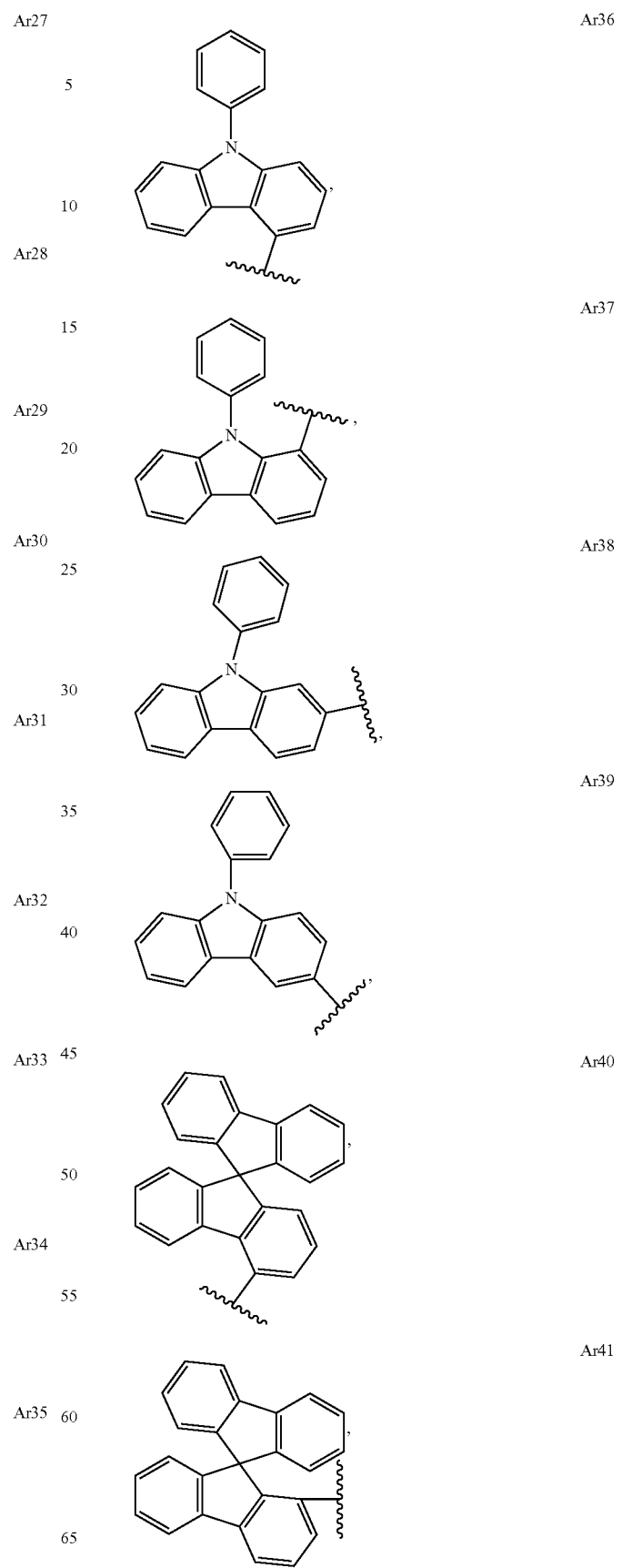

-continued

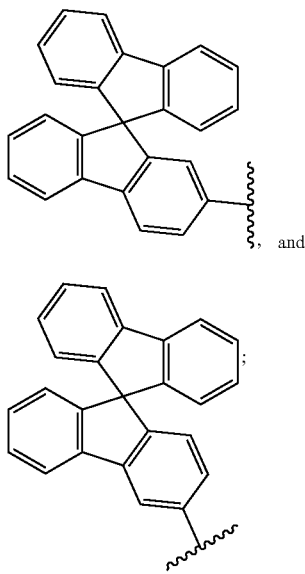

Ar42 and

Ar43 and

R is independently selected from H, deuterium, F, CN, CF$_3$, Me, i-propyl, t-butyl, SiMe$_3$, and SiPh$_3$.

In some embodiments, A is A1. In some embodiments, A is A2. In some embodiments, A is A3. In some embodiments, A is A4. In some embodiments, A is A5. In some embodiments, A is A1 or A3.

In some embodiments, D and D' are the same. In some embodiments, D and D' are different.

In some embodiments, X$_1$ is Ar. In some embodiments, X$_1$ is R.

In some embodiments, X$_2$ is Ar. In some embodiments, X$_2$ is R.

In some embodiments, X$_1$ and X$_2$ are the same. In some embodiments, X$_1$ and X$_2$ are different.

In some embodiments, Ar is Ar1. In some embodiments, Ar is Ar2. In some embodiments, Ar is Ar3. In some embodiments, Ar is Ar4. In some embodiments, D is D5. In some embodiments, Ar is Ar6. In some embodiments, Ar is Ar7. In some embodiments, Ar is Ar8. In some embodiments, Ar is Ar9. In some embodiments, Ar is Ar10. In some embodiments, Ar is Ar11. In some embodiments, Ar is Ar12. In some embodiments, Ar is Ar13. In some embodiments, Ar is Ar14. In some embodiments, Ar is Ar15. In some embodiments, Ar is Ar16. In some embodiments, Ar is Ar17. In some embodiments, Ar is Ar18. In some embodiments, Ar is Ar19. In some embodiments, Ar is Ar20. In some embodiments, Ar is Ar21. In some embodiments, Ar is Ar22. In some embodiments, Ar is Ar23. In some embodiments, Ar is Ar24. In some embodiments, Ar is Ar25. In some embodiments, Ar is Ar26. In some embodiments, Ar is Ar27. In some embodiments, Ar is Ar28. In some embodiments, Ar is Ar29. In some embodiments, Ar is Ar30. In some embodiments, Ar is Ar31. In some embodiments, Ar is Ar32. In some embodiments, Ar is Ar33. In some embodiments, Ar is Ar34. In some embodiments, Ar is Ar35. In some embodiments, Ar is Ar36. In some embodiments, Ar is Ar37. In some embodiments, Ar is Ar38. In some embodiments, Ar is Ar39. In some embodiments, Ar is Ar40. In some embodiments, Ar is Ar41. In some embodiments, Ar is Ar42. In some embodiments, Ar is Ar43.

In some embodiments, Ar is selected from Ar1, Ar2, Ar3, Ar4, Ar5, D6, Ar7, Ar8, Ar9, and Ar10. In some embodiments, Ar is selected from Ar11, Ar12, Ar13, Ar14, Ar15, and Ar16. In some embodiments, Ar is selected from Ar17, Ar18, and Ar19. In some embodiments, Ar is selected from Ar20, Ar21, Ar22, Ar23, and Ar24. In some embodiments, Ar is selected from Ar25, Ar26, and Ar27. In some embodiments, Ar is selected from Ar28, Ar29, Ar30, and Ar31. In some embodiments, Ar is selected from Ar32, Ar33, Ar34, and Ar35. In some embodiments, D' is selected from Ar36, Ar37, Ar38, and Ar39. In some embodiments, Ar is selected from Ar40, Ar41, Ar42 and Ar43.

In some embodiments, R is H. In some embodiments, R is deuterium. In some embodiments, R is F. In some embodiments, R is CN. In some embodiments, R is CF$_3$. In some embodiments, R is Me. In some embodiments, R is i-propyl. In some embodiments, R is t-butyl. In some embodiments, R is SiMe$_3$. In some embodiments, R is SiPh$_3$.

In some embodiments, X$_1$ or X$_2$ is Ar, and Ar is Ar20. In some embodiments, D and D' are the same, X$_1$ or X$_2$ is Ar, and Ar is Ar20. In some embodiments, A is A1 or A3, D and D' are the same, X$_1$ or X$_2$ is Ar, and Ar is Ar20.

In some embodiments the compound of Formula (I) or (II) is selected from 9,9'-(5-(4,6-diphenylpyrimidin-2-yl)-1,3-phenylene)bis(3,6-dimethyl-9H-carbazole)

9,9'-(5-(4,6-diphenyl-1,3,5-triazin-2-yl)-1,3-phenylene)bis(3,6-dimethyl-9H-carbazole)

9,9'-(5-(2,6-diphenylpyrimidin-4-yl)-1,3-phenylene)bis(3,6-dimethyl-9H-carbazole)

9,9'-(5-(4,6-diphenyl-1,3,5-triazin-2-yl)-1,3-phenylene)bis(3,6-di-tert-butyl-9H-carbazole)

9,9'-(5-(2,6-diphenylpyrimidin-4-yl)-1,3-phenylene)bis(3,6-di-tert-butyl-9H-carbazole)

9,9'-(5-(4,6-diphenyl-1,3,5-triazin-2-yl)-1,3-phenylene)bis(3-(pyridin-3-yl)-9H-carbazole)

9,9'-(5-(2,6-diphenylpyrimidin-4-yl)-1,3-phenylene)bis(3-(pyridin-3-yl)-9H-carbazole)

9,9'-(5-(4,6-diphenyl-1,3,5-triazin-2-yl)-1,3-phenylene)bis(3-(pyridin-4-yl)-9H-carbazole)

9,9'-(5-(4,6-diphenylpyrimidin-2-yl)-1,3-phenylene)bis(3,6-di(pyridin-3-yl)-9H-carbazole)

9,9'-(5-(4,6-diphenyl-1,3,5-triazin-2-yl)-1,3-phenylene)bis(3,6-di(pyridin-3-yl)-9H-carbazole)

9,9'-(5-(2,6-diphenylpyrimidin-4-yl)-1,3-phenylene)bis(3,6-di(pyridin-3-yl)-9H-carbazole)

9,9'-(5-(4,6-diphenyl-1,3,5-triazin-2-yl)-1,3-phenylene)bis(3,6-di(pyridin-2-yl)-9H-carbazole)

9,9'-(5-(2,6-diphenylpyrimidin-4-yl)-1,3-phenylene)bis(3,6-di(pyridin-2-yl)-9H-carbazole)

9,9'-(5-(4,6-diphenylpyrimidin-2-yl)-1,3-phenylene)bis(3-(pyridin-2-yl)-9H-carbazole)

9,9'-(5-(4,6-diphenyl-1,3,5-triazin-2-yl)-1,3-phenylene)bis(3-(pyridin-2-yl)-9H-carbazole)

9,9'-(5-(2,6-diphenylpyrimidin-4-yl)-1,3-phenylene)bis(3-(pyridin-2-yl)-9H-carbazole)

9,9'-(5-(4,6-diphenyl-1,3,5-triazin-2-yl)-1,3-phenylene)bis(3,6-di(pyridin-4-yl)-9H-carbazole)

9,9'-(5-(4,6-diphenylpyrimidin-2-yl)-1,3-phenylene)bis(3,6-diphenyl-9H-carbazole)

9,9'-(5-(4,6-diphenyl-1,3,5-triazin-2-yl)-1,3-phenylene)bis(3,6-diphenyl-9H-carbazole)

9,9'-(5-(2,6-diphenylpyrimidin-4-yl)-1,3-phenylene)bis(3,6-diphenyl-9H-carbazole)

9,9'-(5-(4,6-diphenyl-1,3,5-triazin-2-yl)-1,3-phenylene)bis(9H-carbazole-3-carbonitrile) 9,9'-(5-(4,6-diphenyl-1,3,5-triazin-2-yl)-1,3-phenylene)bis(3-(dibenzo[b,d]thiophen-4-yl)-9H-carbazole)
9,9'-(5-(4,6-diphenyl-1,3,5-triazin-2-yl)-1,3-phenylene)bis(3-(dibenzo[b,d]thiophen-1-yl)-9H-carbazole)
9,9'-(5-(4,6-diphenyl-1,3,5-triazin-2-yl)-1,3-phenylene)bis(3-(dibenzo[b,d]furan-4-yl)-9H-carbazole)
9,9'-(5-(4,6-diphenyl-1,3,5-triazin-2-yl)-1,3-phenylene)bis(3-(dibenzo[b,d]furan-1-yl)-9H-carbazole)
9,9'-(5-(4,6-diphenyl-1,3,5-triazin-2-yl)-1,3-phenylene)bis(3-([1,1'-biphenyl]-2-yl)-9H-carbazole)
9,9'-(5-(4,6-diphenyl-1,3,5-triazin-2-yl)-1,3-phenylene)bis(3,6-di([1,1'-biphenyl]-2-yl)-9H-carbazole)
9,9'-(5-(4,6-diphenyl-1,3,5-triazin-2-yl)-1,3-phenylene)bis(3-([1,1'-biphenyl]-3-yl)-9H-carbazole)
9,9'-(5-(4,6-diphenyl-1,3,5-triazin-2-yl)-1,3-phenylene)bis(3,6-di([1,1'-biphenyl]-4-yl)-9H-carbazole)
9,9'-(5-(4,6-diphenyl-1,3,5-triazin-2-yl)-1,3-phenylene)bis(3-phenyl-9H-carbazole)
9,9'-(5-(4,6-diphenyl-1,3,5-triazin-2-yl)-1,3-phenylene)bis(3-methyl-9H-carbazole)
9,9'-(5-(4,6-diphenyl-1,3,5-triazin-2-yl)-1,3-phenylene)bis(3-(tert-butyl)-9H-carbazole)
9,9'-(5-(4,6-diphenyl-1,3,5-triazin-2-yl)-1,3-phenylene)bis(3-([1,1'-biphenyl]-4-yl)-9H-carbazole)
9,9'-(5-(2,6-diphenylpyrimidin-4-yl)-1,3-phenylene)bis(3-([1,1'-biphenyl]-2-yl)-9H-carbazole)
9,9'-(5-(2,6-diphenylpyrimidin-4-yl)-1,3-phenylene)bis(3,6-di([1,1'-biphenyl]-2-yl)-9H-carbazole)
9,9'-(5-(2,6-diphenylpyrimidin-4-yl)-1,3-phenylene)bis(3-([1,1'-biphenyl]-3-yl)-9H-carbazole)
9,9'-(5-(2,6-diphenylpyrimidin-4-yl)-1,3-phenylene)bis(3-phenyl-9H-carbazole)
9,9'-(5-(2,6-diphenylpyrimidin-4-yl)-1,3-phenylene)bis(3-methyl-9H-carbazole)
9,9'-(5-(2,6-diphenylpyrimidin-4-yl)-1,3-phenylene)bis(3-(tert-butyl)-9H-carbazole)
9,9'-(5-(2,6-diphenylpyrimidin-4-yl)-1,3-phenylene)bis(3-([1,1'-biphenyl]-4-yl)-9H-carbazole)
9,9'-(5-(2,6-diphenylpyrimidin-4-yl)-1,3-phenylene)bis(3,6-di([1,1'-biphenyl]-3-yl)-9H-carbazole)
9,9'-(5-(4,6-diphenylpyrimidin-2-yl)-1,3-phenylene)bis(3-([1,1'-biphenyl]-3-yl)-9H-carbazole)
9,9'-(5-(4,6-diphenylpyrimidin-2-yl)-1,3-phenylene)bis(3,6-di([1,1'-biphenyl]-4-yl)-9H-carbazole)
9,9'-(5-(4,6-diphenylpyrimidin-2-yl)-1,3-phenylene)bis(3-phenyl-9H-carbazole)
9,9'-(5-(4,6-diphenylpyrimidin-2-yl)-1,3-phenylene)bis(3-methyl-9H-carbazole)
9,9'-(5-(4,6-diphenylpyrimidin-2-yl)-1,3-phenylene)bis(3-(tert-butyl)-9H-carbazole)
9,9'-(5-(4,6-diphenylpyrimidin-2-yl)-1,3-phenylene)bis(3-([1,1'-biphenyl]-4-yl)-9H-carbazole)
9,9'-(5-(4,6-diphenylpyrimidin-2-yl)-1,3-phenylene)bis(3,6-di([1,1'-biphenyl]-3-yl)-9H-carbazole)
9',9''''-(5-(4,6-diphenylpyridin-2-yl)-1,3-phenylene)bis(9'H-9,3':6',9''-tercarbazole)
5,5',5'',5'''-((5-(4,6-diphenylpyridin-2-yl)-1,3-phenylene)bis(9H-carbazole-9,3,6-triyl))tetrakis(5H-pyrido[3,2-b]indole)
4,4',4'',4'''-((5-(4,6-diphenylpyridin-2-yl)-1,3-phenylene)bis(9H-carbazole-9,3,6-triyl))tetraisophthalonitrile
9,9'-(5-(4,6-diphenylpyridin-2-yl)-1,3-phenylene)bis(3,6-di([1,1'-biphenyl]-2-yl)-9H-carbazole)
9,9'-(5-(4,6-diphenylpyridin-2-yl)-1,3-phenylene)bis(3,6-di-p-tolyl-9H-carbazole) 3,3',3'',3'''-((5-(2,6-diphenylpyridin-4-yl)-1,3-phenylene)bis(9H-carbazole-9,3,6-triyl))tetrabenzonitrile
4,4'-((5-(2,6-diphenylpyridin-4-yl)-1,3-phenylene)bis(9H-carbazole-9,3-diyl))diisophthalonitrile
5,5'-((5-(4,6-diphenylpyrimidin-2-yl)-1,3-phenylene)bis(9H-carbazole-9,3-diyl))bis(5H-pyrido[4,3-b]indole)
9,9'-(5-(4,6-diphenylpyrimidin-2-yl)-1,3-phenylene)bis(3-(9,9'-spirobi[fluoren]-3-yl)-9H-carbazole)
9,9'-(5-(4,6-diphenylpyrimidin-2-yl)-1,3-phenylene)bis(3-(o-tolyl)-9H-carbazole)
9,9'-(5-(4,6-diphenylpyrimidin-2-yl)-1,3-phenylene)bis(3-(dibenzo[b,d]furan-4-yl)-9H-carbazole)
9,9'-((5-(4,6-diphenylpyrimidin-2-yl)-1,3-phenylene)bis(9H-carbazole-9,3-diyl))bis(9H-pyrido[3,4-b]indole)
9,9'-(5-(4,6-diphenylpyrimidin-2-yl)-1,3-phenylene)bis(3-(dibenzo[b,d]thiophen-4-yl)-9H-carbazole)
9',9''''-(5-(4,6-diphenylpyrimidin-2-yl)-1,3-phenylene)bis(9-phenyl-9H,9'H-2,3'-bicarbazole)
9,9'-(5-(4,6-diphenylpyrimidin-2-yl)-1,3-phenylene)bis(3-(9,9'-spirobi[fluoren]-1-yl)-9H-carbazole)
9,9'-(5-(4,6-diphenylpyrimidin-2-yl)-1,3-phenylene)bis(3-(6-phenylpyridin-2-yl)-9H-carbazole)
9,9'-(5-(4,6-diphenylpyrimidin-2-yl)-1,3-phenylene)bis(3-(dibenzo[b,d]furan-3-yl)-9H-carbazole)
9,9'-(5-(4,6-diphenylpyrimidin-2-yl)-1,3-phenylene)bis(3-(dibenzo[b,d]thiophen-3-yl)-9H-carbazole)
9,9'-(5-(4,6-diphenylpyrimidin-2-yl)-1,3-phenylene)bis(3-fluoro-9H-carbazole)
9,9'-(5-(4,6-diphenylpyrimidin-2-yl)-1,3-phenylene)bis(3-(2,6-diphenylpyridin-4-yl)-9H-carbazole)
9,9'-(5-(4,6-diphenylpyrimidin-2-yl)-1,3-phenylene)bis(3-(dibenzo[b,d]furan-1-yl)-9H-carbazole)
9,9'-(5-(4,6-diphenylpyrimidin-2-yl)-1,3-phenylene)bis(3-(9,9'-spirobi[fluoren]-4-yl)-9H-carbazole) 4,4'-((5-(4,6-diphenylpyrimidin-2-yl)-1,3-phenylene)bis(9H-carbazole-9,3-diyl))diisophthalonitrile
9,9'-(5-(4,6-diphenylpyrimidin-2-yl)-1,3-phenylene)bis(3-(p-tolyl)-9H-carbazole)
9',9''''-(5-(4,6-diphenylpyrimidin-2-yl)-1,3-phenylene)bis(9'H-9,3':6',9''-tercarbazole)
5,5',5'',5'''-((5-(4,6-diphenylpyrimidin-2-yl)-1,3-phenylene)bis(9H-carbazole-9,3,6-triyl))tetrakis(5H-pyrido[4,3-b]indole)
9,9'-(5-(4,6-diphenylpyrimidin-2-yl)-1,3-phenylene)bis(3,6-di-o-tolyl-9H-carbazole)
9,9'-(5-(4,6-diphenylpyrimidin-2-yl)-1,3-phenylene)bis(3,6-dimesityl-9H-carbazole)
9,9'-(5-(4,6-diphenylpyrimidin-2-yl)-1,3-phenylene)bis(3,6-bis(dibenzo[b,d]furan-4-yl)-9H-carbazole)
5,5',5'',5'''-((5-(4,6-diphenylpyrimidin-2-yl)-1,3-phenylene)bis(9H-carbazole-9,3,6-triyl))tetrakis(5H-pyrido[3,2-b]indole)
9,9',9'',9'''-((5-(4,6-diphenylpyrimidin-2-yl)-1,3-phenylene)bis(9H-carbazole-9,3,6-triyl))tetrakis(9H-pyrido[2,3-b]indole)
9,9'-(5-(4,6-diphenylpyrimidin-2-yl)-1,3-phenylene)bis(3,6-bis(2,6-dimethylphenyl)-9H-carbazole)
9,9'-(5-(4,6-diphenylpyrimidin-2-yl)-1,3-phenylene)bis(3,6-bis(3,5-dimethylphenyl)-9H-carbazole)
9,9',9'',9'''-((5-(4,6-diphenylpyrimidin-2-yl)-1,3-phenylene)bis(9H-carbazole-9,3,6-triyl))tetrakis(9H-pyrido[3,4-b]indole)
9,9'-(5-(4,6-diphenylpyrimidin-2-yl)-1,3-phenylene)bis(3,6-bis(dibenzo[b,d]thiophen-4-yl)-9H-carbazole)

9,9'-(5-(4,6-diphenylpyrimidin-2-yl)-1,3-phenylene)bis(3,6-bis(6-phenylpyridin-2-yl)-9H-carbazole)
9,9'-(5-(4,6-diphenylpyrimidin-2-yl)-1,3-phenylene)bis(3,6-bis(dibenzo[b,d]furan-3-yl)-9H-carbazole)
9,9'-(5-(4,6-diphenylpyrimidin-2-yl)-1,3-phenylene)bis(3,6-bis(dibenzo[b,d]thiophen-3-yl)-9H-carbazole)
9,9'-(5-(4,6-diphenylpyrimidin-2-yl)-1,3-phenylene)bis(3,6-difluoro-9H-carbazole)
9,9'-(5-(4,6-diphenylpyrimidin-2-yl)-1,3-phenylene)bis(3,6-bis(dibenzo[b,d]furan-1-yl)-9H-carbazole)
9,9'-(5-(4,6-diphenylpyrimidin-2-yl)-1,3-phenylene)bis(3,6-bis(dibenzo[b,d]thiophen-2-yl)-9H-carbazole)
9,9'-(5-(4,6-diphenylpyrimidin-2-yl)-1,3-phenylene)bis(3,6-bis(dibenzo[b,d]furan-2-yl)-9H-carbazole)
9,9'-(5-(4,6-diphenylpyrimidin-2-yl)-1,3-phenylene)bis(3,6-bis(dibenzo[b,d]thiophen-1-yl)-9H-carbazole)
9,9'-(5-(4,6-diphenylpyrimidin-2-yl)-1,3-phenylene)bis(3,6-di-p-tolyl-9H-carbazole)
9',9''''-(5-(4,6-diphenyl-1,3,5-triazin-2-yl)-1,3-phenylene)bis(9'H-9,3':6',9''-tercarbazole)
3,3',3'',3'''-((5-(4,6-diphenyl-1,3,5-triazin-2-yl)-1,3-phenylene)bis(9H-carbazole-9,3,6-triyl))tetrabenzonitrile
5,5',5'',5'''-((5-(4,6-diphenyl-1,3,5-triazin-2-yl)-1,3-phenylene)bis(9H-carbazole-9,3,6-triyl))tetrakis(5H-pyrido[4,3-b]indole)
9,9'-(5-(4,6-diphenyl-1,3,5-triazin-2-yl)-1,3-phenylene)bis(3,6-di-o-tolyl-9H-carbazole)
9,9'-(5-(4,6-diphenyl-1,3,5-triazin-2-yl)-1,3-phenylene)bis(3,6-dimesityl-9H-carbazole)
9,9'-(5-(4,6-diphenyl-1,3,5-triazin-2-yl)-1,3-phenylene)bis(3,6-bis(dibenzo[b,d]furan-4-yl)-9H-carbazole)
2,2',2'',2'''-((5-(4,6-diphenyl-1,3,5-triazin-2-yl)-1,3-phenylene)bis(9H-carbazole-9,3,6-triyl))tetraisophthalonitrile
5,5',5'',5'''-((5-(4,6-diphenyl-1,3,5-triazin-2-yl)-1,3-phenylene)bis(9H-carbazole-9,3,6-triyl))tetrakis(5H-pyrido[3,2-b]indole)
2,2',2'',2'''-((5-(4,6-diphenyl-1,3,5-triazin-2-yl)-1,3-phenylene)bis(9H-carbazole-9,3,6-triyl))tetrabenzonitrile
9,9',9'',9'''-((5-(4,6-diphenyl-1,3,5-triazin-2-yl)-1,3-phenylene)bis(9H-carbazole-9,3,6-triyl))tetrakis(9H-pyrido[2,3-b]indole)
9,9'-(5-(4,6-diphenyl-1,3,5-triazin-2-yl)-1,3-phenylene)bis(3,6-bis(2,6-dimethylphenyl)-9H-carbazole)
9,9'-(5-(4,6-diphenyl-1,3,5-triazin-2-yl)-1,3-phenylene)bis(3,6-bis(3,5-dimethylphenyl)-9H-carbazole)
9,9',9'',9'''-((5-(4,6-diphenyl-1,3,5-triazin-2-yl)-1,3-phenylene)bis(9H-carbazole-9,3,6-triyl))tetrakis(9H-pyrido[3,4-b]indole)
9,9'-(5-(4,6-diphenyl-1,3,5-triazin-2-yl)-1,3-phenylene)bis(3,6-bis(dibenzo[b,d]thiophen-4-yl)-9H-carbazole)
9,9'-(5-(4,6-diphenyl-1,3,5-triazin-2-yl)-1,3-phenylene)bis(3,6-bis(dibenzo[b,d]furan-3-yl)-9H-carbazole)
9,9'-(5-(4,6-diphenyl-1,3,5-triazin-2-yl)-1,3-phenylene)bis(3,6-bis(dibenzo[b,d]thiophen-3-yl)-9H-carbazole)
9,9'-(5-(4,6-diphenyl-1,3,5-triazin-2-yl)-1,3-phenylene)bis(3,6-difluoro-9H-carbazole)
9,9'-(5-(4,6-diphenyl-1,3,5-triazin-2-yl)-1,3-phenylene)bis(3,6-bis(dibenzo[b,d]furan-1-yl)-9H-carbazole)
9,9'-(5-(4,6-diphenyl-1,3,5-triazin-2-yl)-1,3-phenylene)bis(3,6-bis(dibenzo[b,d]thiophen-2-yl)-9H-carbazole)
4,4',4'',4'''-((5-(4,6-diphenyl-1,3,5-triazin-2-yl)-1,3-phenylene)bis(9H-carbazole-9,3,6-triyl))tetraisophthalonitrile
5,5',5'',5'''-((5-(4,6-diphenyl-1,3,5-triazin-2-yl)-1,3-phenylene)bis(9H-carbazole-9,3,6-triyl))tetraisophthalonitrile
9,9'-(5-(4,6-diphenyl-1,3,5-triazin-2-yl)-1,3-phenylene)bis(3,6-bis(dibenzo[b,d]furan-2-yl)-9H-carbazole)
4,4',4'',4'''-((5-(4,6-diphenyl-1,3,5-triazin-2-yl)-1,3-phenylene)bis(9H-carbazole-9,3,6-triyl))tetrabenzonitrile
9,9'-(5-(4,6-diphenyl-1,3,5-triazin-2-yl)-1,3-phenylene)bis(3,6-bis(dibenzo[b,d]thiophen-1-yl)-9H-carbazole)
9,9'-(5-(4,6-diphenyl-1,3,5-triazin-2-yl)-1,3-phenylene)bis(3,6-di-m-tolyl-9H-carbazole)
9,9'-(5-(4,6-diphenyl-1,3,5-triazin-2-yl)-1,3-phenylene)bis(3,6-di-p-tolyl-9H-carbazole)
9',9''''-(5-(2,6-diphenylpyrimidin-4-yl)-1,3-phenylene)bis(9'H-9,3':6',9''-tercarbazole)
5,5',5'',5'''-((5-(2,6-diphenylpyrimidin-4-yl)-1,3-phenylene)bis(9H-carbazole-9,3,6-triyl))tetrakis(5H-pyrido[4,3-b]indole)
9,9'-(5-(2,6-diphenylpyrimidin-4-yl)-1,3-phenylene)bis(3,6-di-o-tolyl-9H-carbazole)
9,9'-(5-(2,6-diphenylpyrimidin-4-yl)-1,3-phenylene)bis(3,6-dimesityl-9H-carbazole)
9,9'-(5-(2,6-diphenylpyrimidin-4-yl)-1,3-phenylene)bis(3,6-bis(dibenzo[b,d]furan-4-yl)-9H-carbazole)
5,5',5'',5'''-((5-(2,6-diphenylpyrimidin-4-yl)-1,3-phenylene)bis(9H-carbazole-9,3,6-triyl))tetrakis(5H-pyrido[3,2-b]indole)
9,9',9'',9'''-((5-(2,6-diphenylpyrimidin-4-yl)-1,3-phenylene)bis(9H-carbazole-9,3,6-triyl))tetrakis(9H-pyrido[2,3-b]indole)
9,9'-(5-(2,6-diphenylpyrimidin-4-yl)-1,3-phenylene)bis(3,6-bis(2,6-dimethylphenyl)-9H-carbazole)
9,9'-(5-(2,6-diphenylpyrimidin-4-yl)-1,3-phenylene)bis(3,6-bis(3,5-dimethylphenyl)-9H-carbazole)
9,9',9'',9'''-((5-(2,6-diphenylpyrimidin-4-yl)-1,3-phenylene)bis(9H-carbazole-9,3,6-triyl))tetrakis(9H-pyrido[3,4-b]indole)
9,9'-(5-(2,6-diphenylpyrimidin-4-yl)-1,3-phenylene)bis(3,6-bis(dibenzo[b,d]thiophen-4-yl)-9H-carbazole)
9,9'-(5-(2,6-diphenylpyrimidin-4-yl)-1,3-phenylene)bis(3,6-bis(6-phenylpyridin-2-yl)-9H-carbazole)
9,9'-(5-(2,6-diphenylpyrimidin-4-yl)-1,3-phenylene)bis(3,6-bis(dibenzo[b,d]furan-3-yl)-9H-carbazole)
9,9'-(5-(2,6-diphenylpyrimidin-4-yl)-1,3-phenylene)bis(3,6-bis(dibenzo[b,d]thiophen-3-yl)-9H-carbazole)
9,9'-(5-(2,6-diphenylpyrimidin-4-yl)-1,3-phenylene)bis(3,6-difluoro-9H-carbazole)
9,9'-(5-(2,6-diphenylpyrimidin-4-yl)-1,3-phenylene)bis(3,6-bis(dibenzo[b,d]furan-1-yl)-9H-carbazole)
9,9'-(5-(2,6-diphenylpyrimidin-4-yl)-1,3-phenylene)bis(3,6-bis(dibenzo[b,d]thiophen-2-yl)-9H-carbazole)
4,4',4'',4'''-((5-(2,6-diphenylpyrimidin-4-yl)-1,3-phenylene)bis(9H-carbazole-9,3,6-triyl))tetraisophthalonitrile
9,9'-(5-(2,6-diphenylpyrimidin-4-yl)-1,3-phenylene)bis(3,6-bis(dibenzo[b,d]furan-2-yl)-9H-carbazole)
9,9'-(5-(2,6-diphenylpyrimidin-4-yl)-1,3-phenylene)bis(3,6-bis(dibenzo[b,d]thiophen-1-yl)-9H-carbazole)
9,9'-(5-(2,6-diphenylpyrimidin-4-yl)-1,3-phenylene)bis(3,6-di-m-tolyl-9H-carbazole)
9,9'-(5-(2,6-diphenylpyrimidin-4-yl)-1,3-phenylene)bis(3,6-di-p-tolyl-9H-carbazole)
9',9''''-(5-(2,6-diphenylpyrimidin-4-yl)-1,3-phenylene)bis(9-phenyl-9H,9'H-3,3'-bicarbazole)
9,9'-(5-(2,6-diphenylpyrimidin-4-yl)-1,3-phenylene)bis(3-(9,9'-spirobi[fluoren]-3-yl)-9H-carbazole)
9,9'-(5-(2,6-diphenylpyrimidin-4-yl)-1,3-phenylene)bis(3-(o-tolyl)-9H-carbazole)
9,9'-(5-(2,6-diphenylpyrimidin-4-yl)-1,3-phenylene)bis(3-mesityl-9H-carbazole)

9,9'-(5-(2,6-diphenylpyrimidin-4-yl)-1,3-phenylene)bis(3-(dibenzo[b,d]furan-4-yl)-9H-carbazole)
5,5'-((5-(2,6-diphenylpyrimidin-4-yl)-1,3-phenylene)bis(9H-carbazole-9,3-diyl))bis(5H-pyrido[3,2-b]indole)
9,9'-((5-(2,6-diphenylpyrimidin-4-yl)-1,3-phenylene)bis(9H-carbazole-9,3-diyl))bis(9H-pyrido[2,3-b]indole)
9,9'-(5-(2,6-diphenylpyrimidin-4-yl)-1,3-phenylene)bis(3-(2,6-dimethylphenyl)-9H-carbazole)
9,9'-(5-(2,6-diphenylpyrimidin-4-yl)-1,3-phenylene)bis(3-(3,5-dimethylphenyl)-9H-carbazole)
9,9'-(5-(2,6-diphenylpyrimidin-4-yl)-1,3-phenylene)bis(3-(dibenzo[b,d]thiophen-4-yl)-9H-carbazole)
9',9'''-(5-(2,6-diphenylpyrimidin-4-yl)-1,3-phenylene)bis(9-phenyl-9H,9'H-2,3'-bicarbazole)
9,9'-(5-(2,6-diphenylpyrimidin-4-yl)-1,3-phenylene)bis(3-(9,9'-spirobi[fluoren]-1-yl)-9H-carbazole)
9,9'-(5-(2,6-diphenylpyrimidin-4-yl)-1,3-phenylene)bis(3-(6-phenylpyridin-2-yl)-9H-carbazole)
9,9'-(5-(2,6-diphenylpyrimidin-4-yl)-1,3-phenylene)bis(3-(dibenzo[b,d]furan-3-yl)-9H-carbazole)
9,9'-(5-(2,6-diphenylpyrimidin-4-yl)-1,3-phenylene)bis(3-(dibenzo[b,d]thiophen-3-yl)-9H-carbazole)
9,9'-(5-(2,6-diphenylpyrimidin-4-yl)-1,3-phenylene)bis(3-fluoro-9H-carbazole)
9,9'-(5-(2,6-diphenylpyrimidin-4-yl)-1,3-phenylene)bis(3-(2,6-diphenylpyridin-4-yl)-9H-carbazole)
9,9'-(5-(2,6-diphenylpyrimidin-4-yl)-1,3-phenylene)bis(3-(9,9'-spirobi[fluoren]-2-yl)-9H-carbazole)
9,9'-(5-(2,6-diphenylpyrimidin-4-yl)-1,3-phenylene)bis(3-(dibenzo[b,d]furan-1-yl)-9H-carbazole)
9,9'-(5-(2,6-diphenylpyrimidin-4-yl)-1,3-phenylene)bis(3-(9,9'-spirobi[fluoren]-4-yl)-9H-carbazole)
9,9'-(5-(2,6-diphenylpyrimidin-4-yl)-1,3-phenylene)bis(3-(dibenzo[b,d]thiophen-2-yl)-9H-carbazole)
4,4'-((5-(2,6-diphenylpyrimidin-4-yl)-1,3-phenylene)bis(9H-carbazole-9,3-diyl))diisophthalonitrile
5,5'-((5-(2,6-diphenylpyrimidin-4-yl)-1,3-phenylene)bis(9H-carbazole-9,3-diyl))diisophthalonitrile
9,9'-(5-(2,6-diphenylpyrimidin-4-yl)-1,3-phenylene)bis(3-(dibenzo[b,d]furan-2-yl)-9H-carbazole)
9,9'-(5-(2,6-diphenylpyrimidin-4-yl)-1,3-phenylene)bis(3-(dibenzo[b,d]thiophen-1-yl)-9H-carbazole)
9,9'-(5-(2,6-diphenylpyrimidin-4-yl)-1,3-phenylene)bis(3-(m-tolyl)-9H-carbazole)
9,9'-(5-(2,6-diphenylpyrimidin-4-yl)-1,3-phenylene)bis(3-(p-tolyl)-9H-carbazole) 4,4'-((5-(4,6-diphenylpyridin-2-yl)-1,3-phenylene)bis(9H-carbazole-9,3-diyl))diisophthalonitrile
9,9'-(5-(4,6-diphenylpyridin-2-yl)-1,3-phenylene)bis(3-(p-tolyl)-9H-carbazole)
3,3'-((5-(4,6-diphenyl-1,3,5-triazin-2-yl)-1,3-phenylene)bis(9H-carbazole-9,3-diyl))dibenzonitrile
5,5'-((5-(4,6-diphenyl-1,3,5-triazin-2-yl)-1,3-phenylene)bis(9H-carbazole-9,3-diyl))bis(5H-pyrido[4,3-b]indole)
9,9'-(5-(4,6-diphenyl-1,3,5-triazin-2-yl)-1,3-phenylene)bis(3-(9,9'-spirobi[fluoren]-3-yl)-9H-carbazole)
9,9'-(5-(4,6-diphenyl-1,3,5-triazin-2-yl)-1,3-phenylene)bis(3-(o-tolyl)-9H-carbazole)
9,9'-(5-(4,6-diphenyl-1,3,5-triazin-2-yl)-1,3-phenylene)bis(3-mesityl-9H-carbazole)
2,2'-((5-(4,6-diphenyl-1,3,5-triazin-2-yl)-1,3-phenylene)bis(9H-carbazole-9,3-diyl))diisophthalonitrile
5,5'-((5-(4,6-diphenyl-1,3,5-triazin-2-yl)-1,3-phenylene)bis(9H-carbazole-9,3-diyl))bis(5H-pyrido[3,2-b]indole)
2,2'-((5-(4,6-diphenyl-1,3,5-triazin-2-yl)-1,3-phenylene)bis(9H-carbazole-9,3-diyl))dibenzonitrile
9,9'-((5-(4,6-diphenyl-1,3,5-triazin-2-yl)-1,3-phenylene)bis(9H-carbazole-9,3-diyl))bis(9H-pyrido[2,3-b]indole)
9,9'-(5-(4,6-diphenyl-1,3,5-triazin-2-yl)-1,3-phenylene)bis(3-(2,6-dimethylphenyl)-9H-carbazole)
9,9'''-(5-(4,6-diphenyl-1,3,5-triazin-2-yl)-1,3-phenylene)bis(9'-phenyl-9H,9'H-3,4'-bicarbazole)
9,9'-(5-(4,6-diphenyl-1,3,5-triazin-2-yl)-1,3-phenylene)bis(3-(3,5-dimethylphenyl)-9H-carbazole)
9,9'-((5-(4,6-diphenyl-1,3,5-triazin-2-yl)-1,3-phenylene)bis(9H-carbazole-9,3-diyl))bis(9H-pyrido[3,4-b]indole)
9,9'-(5-(4,6-diphenyl-1,3,5-triazin-2-yl)-1,3-phenylene)bis(3-(trifluoromethyl)-9H-carbazole)
9',9'''-(5-(4,6-diphenyl-1,3,5-triazin-2-yl)-1,3-phenylene)bis(9-phenyl-9H,9'H-2,3'-bicarbazole)
9,9'-(5-(4,6-diphenyl-1,3,5-triazin-2-yl)-1,3-phenylene)bis(3-(9,9'-spirobi[fluoren]-1-yl)-9H-carbazole)
9,9'-(5-(4,6-diphenyl-1,3,5-triazin-2-yl)-1,3-phenylene)bis(3-(6-phenylpyridin-2-yl)-9H-carbazole)
9,9'-(5-(4,6-diphenyl-1,3,5-triazin-2-yl)-1,3-phenylene)bis(3-(dibenzo[b,d]furan-3-yl)-9H-carbazole)
9,9'-(5-(4,6-diphenyl-1,3,5-triazin-2-yl)-1,3-phenylene)bis(3-(dibenzo[b,d]thiophen-3-yl)-9H-carbazole)
9,9'-(5-(4,6-diphenyl-1,3,5-triazin-2-yl)-1,3-phenylene)bis(3-fluoro-9H-carbazole)
9,9'-(5-(4,6-diphenyl-1,3,5-triazin-2-yl)-1,3-phenylene)bis(3-(2,6-diphenylpyridin-4-yl)-9H-carbazole)
9,9'-(5-(4,6-diphenyl-1,3,5-triazin-2-yl)-1,3-phenylene)bis(3-(9,9'-spirobi[fluoren]-2-yl)-9H-carbazole)
9,9'-(5-(4,6-diphenyl-1,3,5-triazin-2-yl)-1,3-phenylene)bis(3-(9,9'-spirobi[fluoren]-4-yl)-9H-carbazole)
9,9'-(5-(4,6-diphenyl-1,3,5-triazin-2-yl)-1,3-phenylene)bis(3-(dibenzo[b,d]thiophen-2-yl)-9H-carbazole)
9',9'''-(5-(4,6-diphenyl-1,3,5-triazin-2-yl)-1,3-phenylene)bis(9-phenyl-9H,9'H-1,3'-bicarbazole)
4,4'-((5-(4,6-diphenyl-1,3,5-triazin-2-yl)-1,3-phenylene)bis(9H-carbazole-9,3-diyl))diisophthalonitrile
5,5'-((5-(4,6-diphenyl-1,3,5-triazin-2-yl)-1,3-phenylene)bis(9H-carbazole-9,3-diyl))diisophthalonitrile
9,9'-(5-(4,6-diphenyl-1,3,5-triazin-2-yl)-1,3-phenylene)bis(3-(dibenzo[b,d]furan-2-yl)-9H-carbazole)
4,4'-((5-(4,6-diphenyl-1,3,5-triazin-2-yl)-1,3-phenylene)bis(9H-carbazole-9,3-diyl))dibenzonitrile
9,9'-(5-(4,6-diphenyl-1,3,5-triazin-2-yl)-1,3-phenylene)bis(3-(m-tolyl)-9H-carbazole); and
9,9'-(5-(4,6-diphenyl-1,3,5-triazin-2-yl)-1,3-phenylene)bis(3-(p-tolyl)-9H-carbazole).

In some embodiments, the compound of Formula (I) or (II) is selected from:

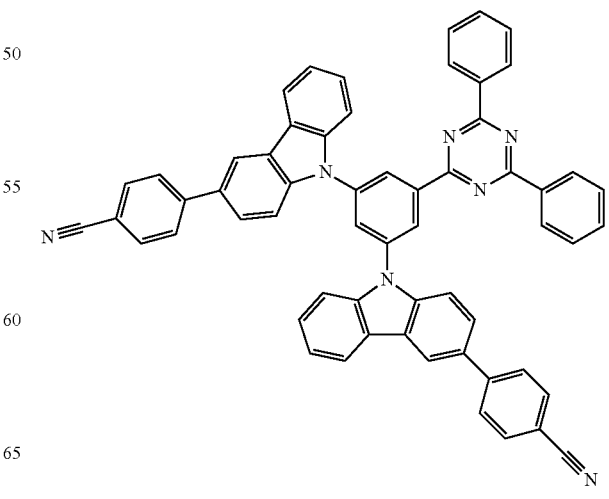

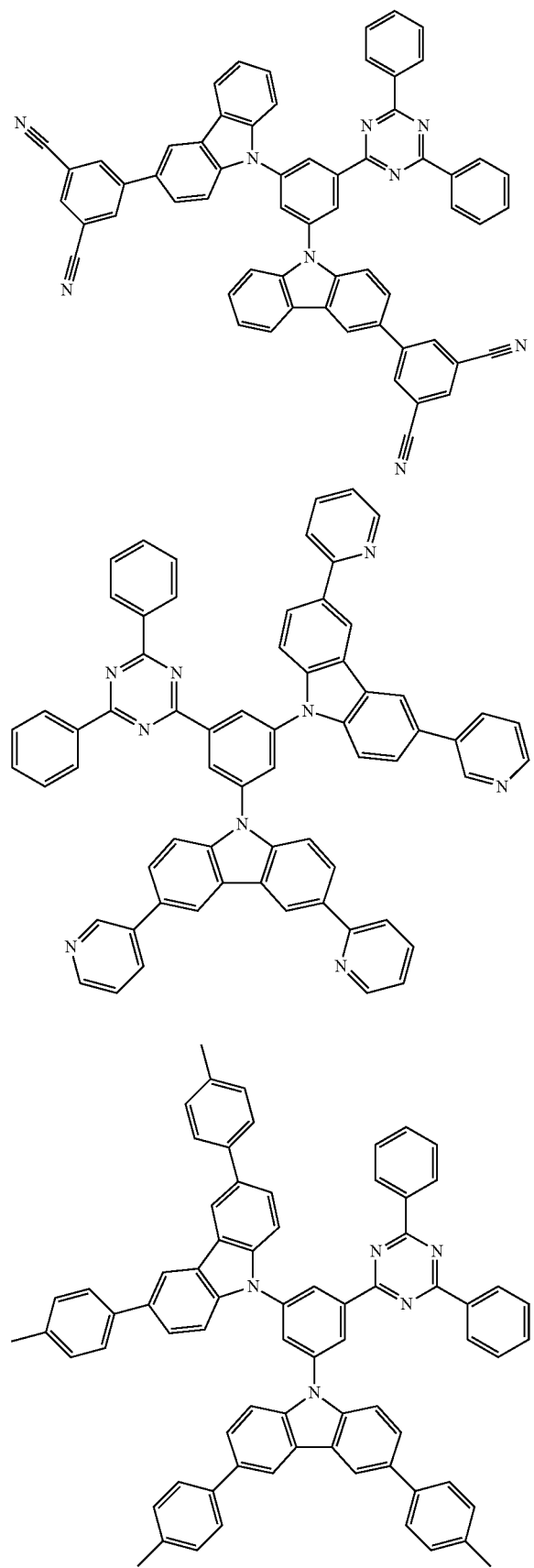
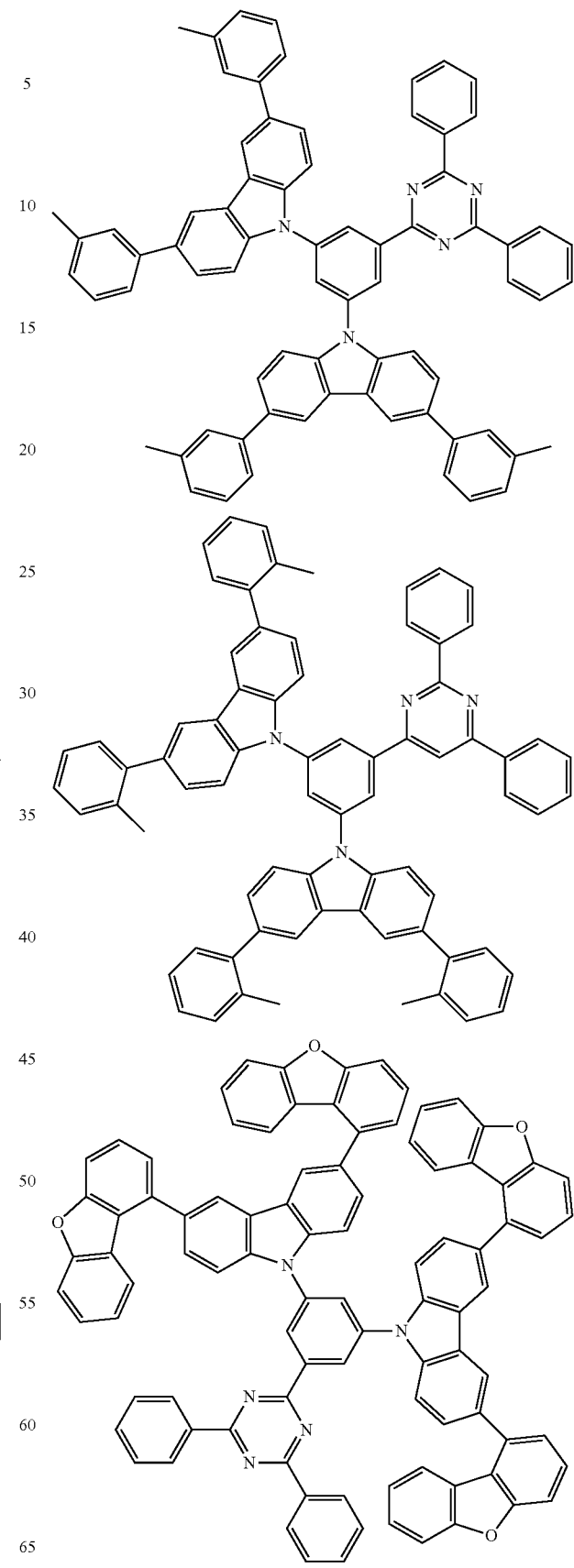

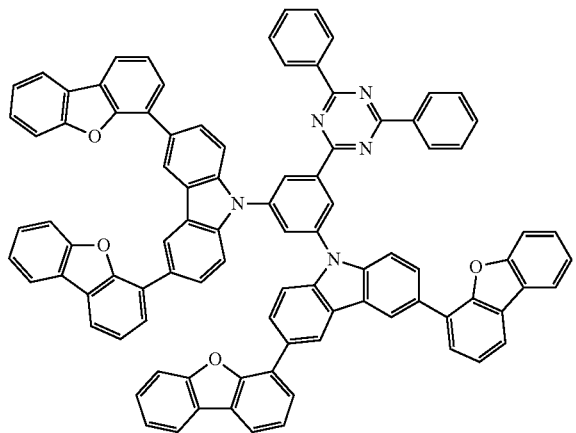
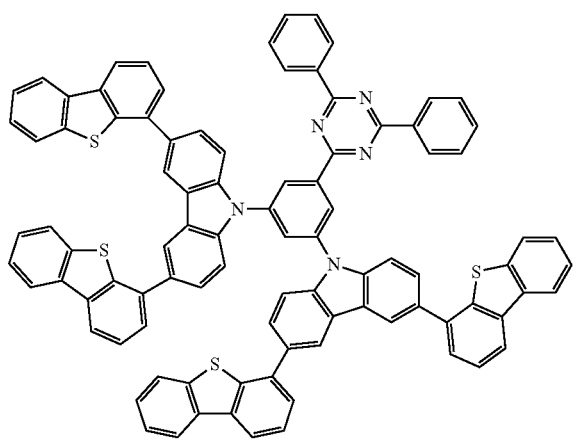
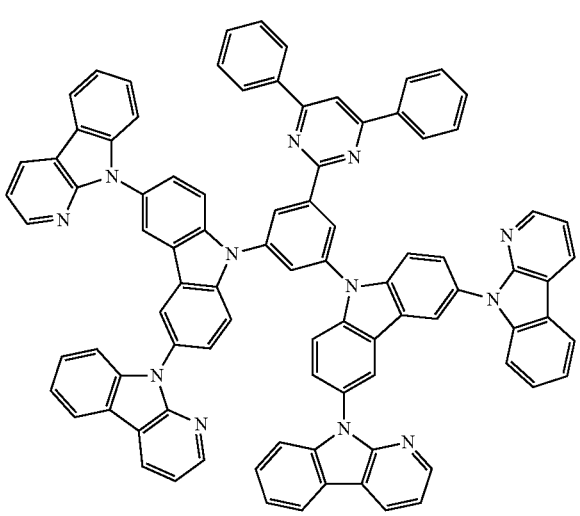
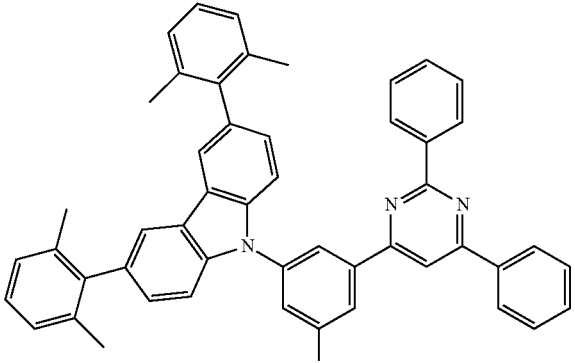
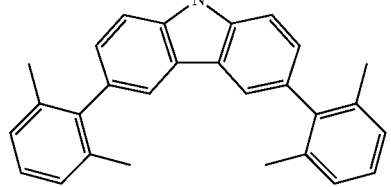
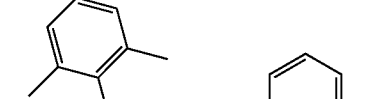
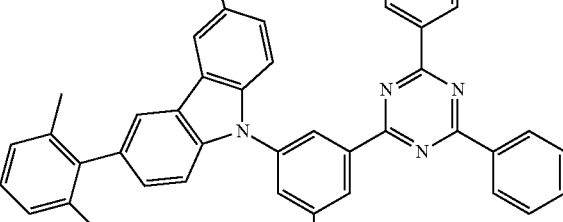
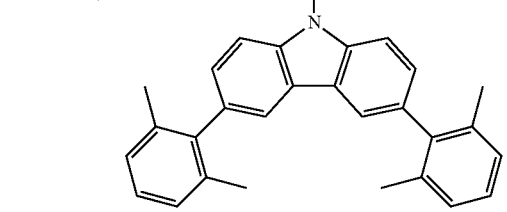
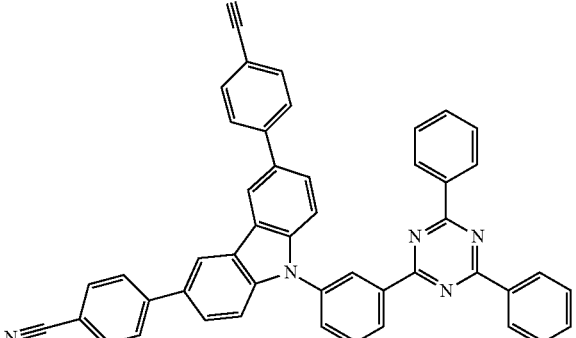
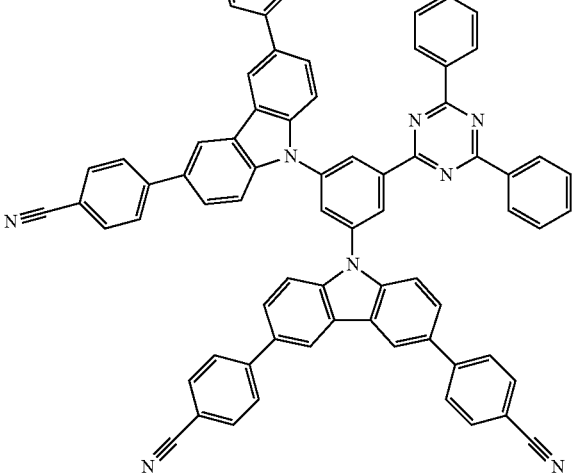

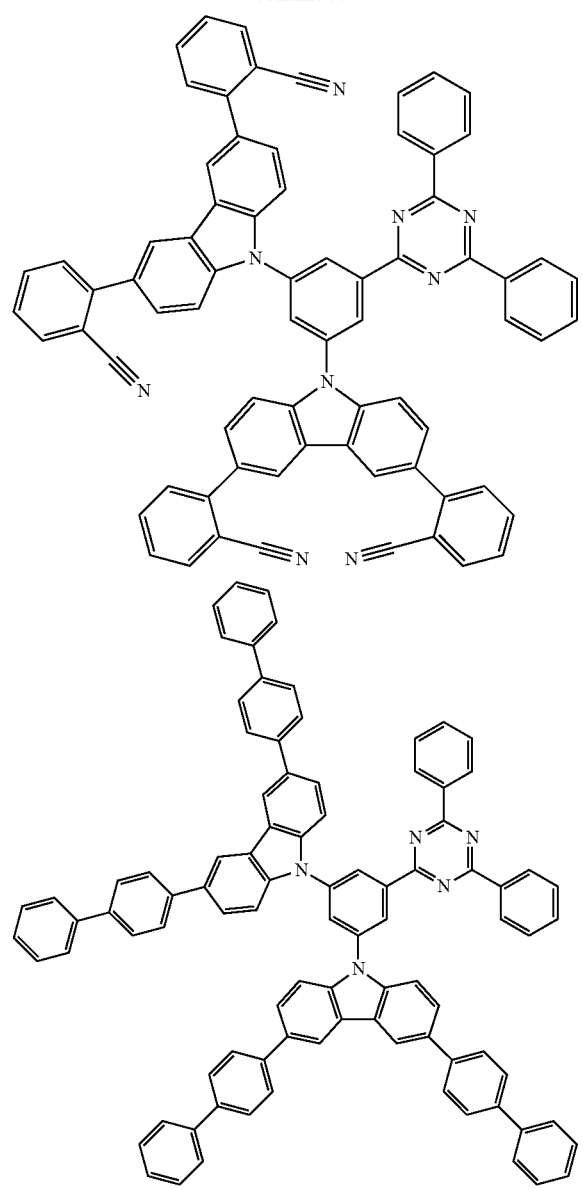
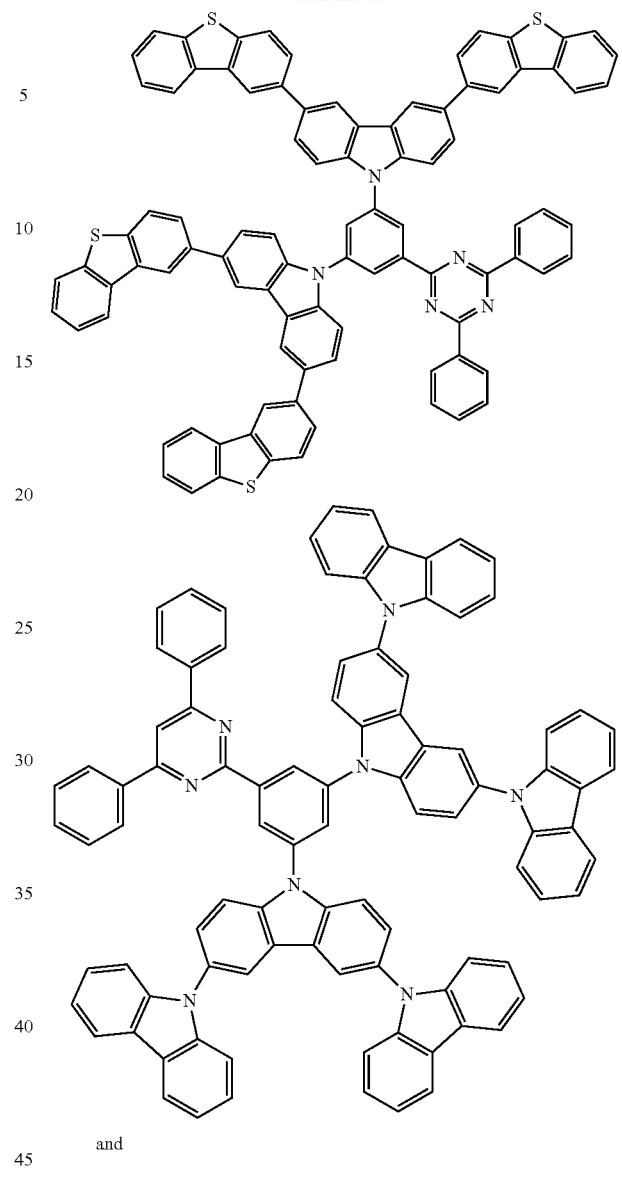
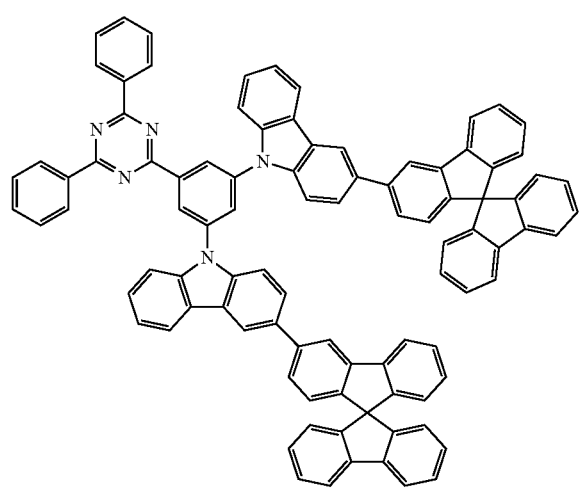
and
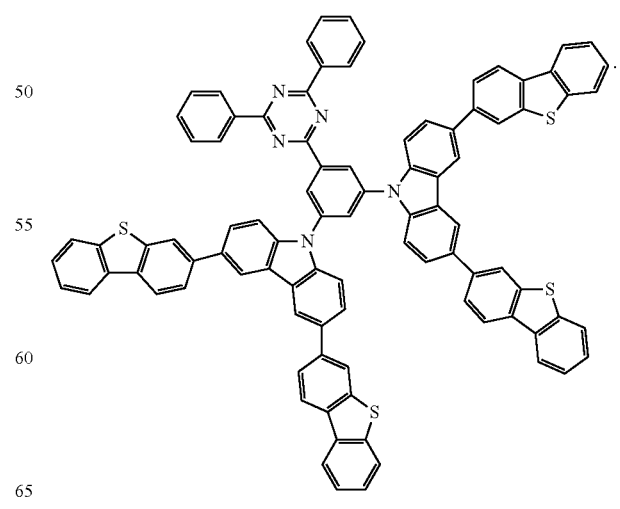

In some embodiments, the compound of Formula (I) or (II) is selected from

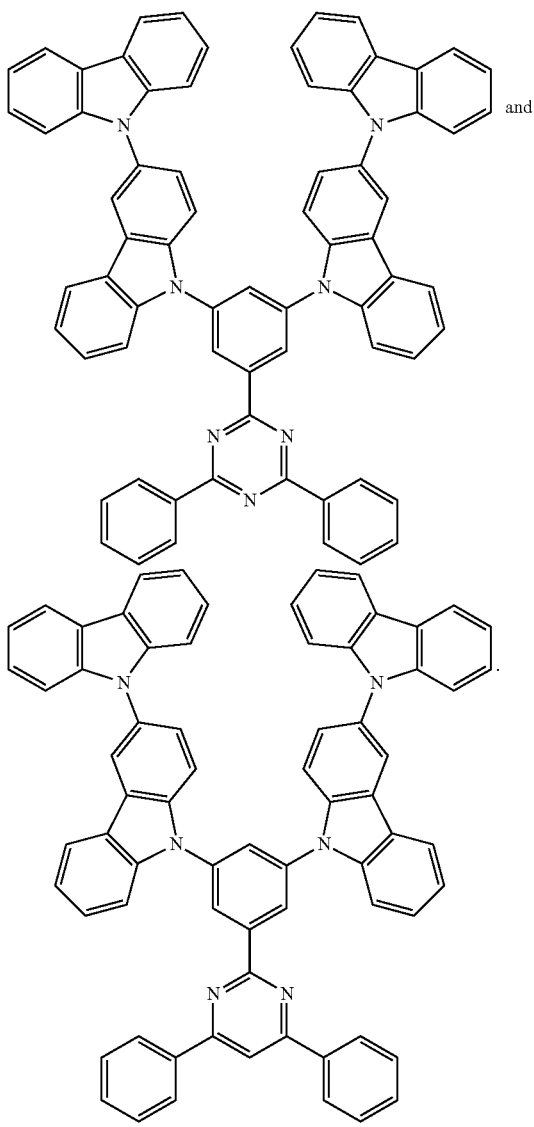

and

.

In some embodiments, compounds of Formula (I) or (II) are substituted with deuterium.

In some embodiments, compounds of Formula (I) or (II) are light-emitting materials.

In some embodiments, compounds of Formula (I) or (II) are compound capable of emitting delayed fluorescence.

In some embodiments of the present disclosure, when excited via thermal or electronic means, the compounds of Formula (I) or (II) can produce light in ultraviolet region, the blue, green, yellow, orange, or red region of the visible spectrum (e.g., about 420 nm to about 500 nm, about 500 nm to about 600 nm, or about 600 nm to about 700 nm), or near-infrared region.

In some embodiments of the present disclosure, when excited via thermal or electronic means, the compounds of Formula (I) or (II) can produce light in the red or orange region of the visible spectrum (e.g., about 620 nm to about 780 nm; about 650 nm).

In some embodiments of the present disclosure, when excited via thermal or electronic means, the compounds of Formula (I) or (II) can produce light in the orange or yellow region of the visible spectrum (e.g., about 570 nm to about 620 nm; about 590 nm; about 570 nm).

In some embodiments of the present disclosure, when excited via thermal or electronic means, the compounds of Formula (I) or (II) can produce light in the green region of the visible spectrum (e.g., about 490 nm to about 575 nm; about 510 nm).

In some embodiments of the present disclosure, when excited via thermal or electronic means, the compounds of Formula (I) or (II) can produce light in the blue region of the visible spectrum (e.g., about 400 nm to about 490 nm; about 475 nm).

Electronic properties of a library of small chemical molecules can be computed using known ab initio quantum mechanical computations. For example, using a time-dependent density functional theory using, as a basis set, the set of functions known as 6-31G* and a Becke, 3-parameter, Lee-Yang-Parr hybrid functional to solve Hartree-Fock equations (TD-DFT/B3LYP/6-31G*), molecular fragments (moieties) can be screened which have HOMOs above a specific threshold and LUMOs below a specific threshold, and wherein the calculated triplet state of the moieties is above 2.75 eV.

Therefore, for example, a donor moiety ("D") can be selected because it has a HOMO energy (e.g., an ionization potential) of greater than or equal to −6.5 eV. An acceptor moiety ("A") can be selected because it has, for example, a LUMO energy (e.g., an electron affinity) of less than or equal to −0.5 eV. The linker moiety ("L") can be a rigid conjugated system which can, for example, sterically restrict the acceptor and donor moieties into a specific configuration, thereby preventing the overlap between the conjugated a system of donor and acceptor moieties.

In some embodiments, the compound library is filtered using one or more of the following properties:
1. emission near a certain wavelength;
2. calculated triplet state above a certain energy level;
3. $\Delta E_{ST}$ value below a certain value;
4. quantum yield above a certain value;
5. HOMO level; and
6. LUMO level.

In some embodiments, the difference between the lowest singlet excited state and the lowest triplet excited state at 77K ($\Delta E_{ST}$) is less than about 0.5 eV, less than about 0.4 eV, less than about 0.3 eV, less than about 0.2 eV, or less than about 0.1 eV. In some embodiments, the $\Delta E_{ST}$ value is less than about 0.09 eV, less than about 0.08 eV, less than about 0.07 eV, less than about 0.06 eV, less than about 0.05 eV, less than about 0.04 eV, less than about 0.03 eV, less than about 0.02 eV, or less than about 0.01 eV.

In some embodiments, a compound of Formula (I) or (II) exhibits a quantum yield of greater than 25%, such as about 30%, about 35%, about 40%, about 45%, about 50%, about 55%, about 60%/a, about 65%, about 70%, about 75%, about 80%, about 85%, about 90%, about 95%, or greater.

Compositions with the Disclosed Compounds

In some embodiments, a compound of Formula (I) or (II) is combined with, dispersed within, covalently bonded to, coated with, formed on, or otherwise associated with, one or more materials (e.g., small molecules, polymers, metals, metal complexes, etc.) to form a film or layer in solid state. For example, the compound of Formula (I) or (II) may be combined with an electroactive material to form a film. In some cases, the compound of Formula (I) or (II) may be combined with a hole-transport polymer. In some cases, the compound of Formula (I) or (II) may be combined with an electron-transport polymer. In some cases, the compound of Formula (I) or (II) may be combined with a hole-transport polymer and an electron-transport polymer. In some cases, the compound of Formula (I) or (II) may be combined with a copolymer comprising both hole-transport portions and electron-transport portions. In such embodiments, electrons and/or holes formed within the solid film or layer may interact with the compound of Formula (I) or (II).

Exemplary Uses of the Disclosed Compound

Organic Light-Emitting Diodes

One aspect of the invention relates to use of the compound of Formula (I) or (II) of the invention as a light-emitting material of an organic light-emitting device. In some embodiments, the compound represented by the Formula (I) or (II) of the invention may be effectively used as a light-emitting material in a light-emitting layer of an organic light-emitting device. In some embodiments, the compound of Formula (I) or (II) comprises a delayed fluorescent material emitting delayed fluorescent light (delayed fluorescence emitter).

In some embodiments, the invention provides a delayed fluorescence emitter having the structure of Formula (I) or (II). In some embodiments, the invention relates to the use of the compound of Formula (I) or (II) as the delayed fluorescence emitter. In some embodiments, the light-emitting layer comprises a compound of Formula (I) or (II) as an assist dopant. In some embodiments, the compound of Formula (I) or (II) can be used as a host material and used with one or more light-emitting materials, and the light-emitting material can be a fluorescent material, a phosphorescent material or a TADF material. In some embodiments, the compound of Formula (I) or (II) can be used as a hole transport material. In some embodiments, the compound of Formula (I) or (II) can be used as an electron transport material. In some embodiments, the invention relates to a method for emitting delayed fluorescent light from the compound of Formula (I) or (II). In some embodiments, an organic light-emitting device comprising the compound as a light-emitting material, emits delayed fluorescent light, and has a high light emission efficiency.

In some embodiments, a light-emitting layer comprises a compound of Formula (I) or (II), wherein the compound of Formula (I) or (II) is oriented parallel to the substrate. In some embodiments, the substrate is a film forming surface. In some embodiments, the orientation of the compound of Formula (I) or (II) with respect to the film forming surface influences or determines the propagation directions of the light emitted by the compound to be aligned. In some embodiments, the alignment of the propagation directions of the light emitted by the compound of Formula (I) or (II) enhances the light extraction efficiency from the light-emitting layer.

One aspect of the invention relates to an organic light-emitting device. In some embodiments, the organic light-emitting device comprises a light-emitting layer. In some embodiments, the light-emitting layer comprises a compound of Formula (I) or (II) as a light-emitting material. In some embodiments, the organic light-emitting device is an organic photoluminescent device (organic PL device). In some embodiments, the organic light-emitting device is an organic electroluminescent device (organic EL device). In some embodiments, the compound of Formula (I) or (II) assists the light emission of another light-emitting material comprised in the light-emitting layer, i.e., as a so-called assistant dopant. In some embodiments, the compound of Formula (I) or (II) comprised in the light-emitting layer is in its lowest excited singlet energy level, which is comprised between the lowest excited singlet energy level of the host material comprised in the light-emitting layer and the lowest excited singlet energy level of another light-emitting material comprised in the light-emitting layer.

In some embodiments, the organic photoluminescent device comprises at least one light-emitting layer. In some embodiments, the organic electroluminescent device comprises at least an anode, a cathode, and an organic layer between the anode and the cathode. In some embodiments, the organic layer comprises at least a light-emitting layer. In some embodiments, the organic layer comprises only a light-emitting layer. In some embodiments, the organic layer, comprises one or more organic layers in addition to the light-emitting layer. Examples of the organic layer include a hole transporting layer, a hole injection layer, an electron barrier layer, a hole barrier layer, an electron injection layer, an electron transporting layer and an exciton barrier layer. In some embodiments, the hole transporting layer may be a hole injection and transporting layer having a hole injection function, and the electron transporting layer may be an electron injection and transporting layer having an electron injection function. An example of an organic electroluminescent device is shown in the FIGURE.

Substrate

In some embodiments, the organic electroluminescent device of the invention is supported by a substrate, wherein the substrate is not particularly limited and may be any of those that have been commonly used in an organic electroluminescent device, for example those formed of glass, transparent plastics, quartz and silicon.

Anode

In some embodiments, the anode of the organic electroluminescent device is made of a metal, an alloy, an electroconductive compound, or a combination thereof. In some embodiments, the metal, alloy, or electroconductive compound has a large work function (4 eV or more). In some embodiments, the metal is Au. In some embodiments, the electroconductive transparent material is selected from CuI, indium tin oxide (ITO), $SnO_2$, and ZnO. In some embodiments, an amorphous material capable of forming a transparent electroconductive film, such as IDIXO ($In_2O_3$—ZnO), is be used. In some embodiments, the anode is a thin film. In some embodiments the thin film is made by vapor deposition or sputtering. In some embodiments, the film is patterned by a photolithography method. In some embodiments, where the pattern may not require high accuracy (for example, approximately 100 μm or more), the pattern may be formed with a mask having a desired shape on vapor deposition or sputtering of the electrode material. In some embodiments, when a material can be applied as a coating, such as an organic electroconductive compound, a wet film forming method, such as a printing method and a coating method is used. In some embodiments, when the emitted light goes through the anode, the anode has a transmittance of more than 10%, and the anode has a sheet resistance of several hundred Ohm per square or less. In some embodiments, the thickness of the anode is from 10 to 1,000 nm. In some embodiments, the thickness of the anode is from 10 to 200 nm. In some embodiments, the thickness of the anode varies depending on the material used.

Cathode

In some embodiments, the cathode is made of an electrode material a metal having a small work function (4 eV or less) (referred to as an electron injection metal), an alloy, an electroconductive compound, or a combination thereof. In some embodiments, the electrode material is selected from sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. In some embodiments, a mixture of an electron injection metal and a second metal that is a stable metal having a larger work function than the electron injection metal is used. In some embodiments, the mixture is selected from a magnesium-silver mixture, a magnesium-aluminum mixture, a magnesium-indium mixture, an aluminum-aluminum oxide ($Al_2O_3$) mixture, a lithium-aluminum mixture, and aluminium. In some embodiments, the mixture increases the electron injection property and the durability against oxidation. In some embodiments, the cathode is produced by forming the electrode material into a thin film by vapor deposition or sputtering. In some embodiments, the cathode has a sheet resistance of several hundred Ohm per square or less. In some embodiments, the thickness of the cathode ranges from 10 nm to 5 μm. In some embodiments, the thickness of the cathode ranges from 50 to 200 nm. In some embodiments, for transmitting the emitted light, any one of the anode and the cathode of the organic electroluminescent device is transparent or translucent. In some embodiments, the transparent or translucent electroluminescent devices enhances the light emission luminance.

In some embodiments, the cathode is formed with an electroconductive transparent material, as described for the anode, to form a transparent or translucent cathode. In some embodiments, a device comprises an anode and a cathode, both being transparent or translucent.

Light-Emitting Layer

In some embodiments, the light-emitting layer is a layer, in which holes and electrons, injected respectively from the anode and the cathode, are recombined to form excitons. In some embodiments the layer emits light.

In some embodiments, a light-emitting material is solely used as the light-emitting layer. In some embodiments, the light-emitting layer contains a light-emitting material, and a host material. In some embodiments, the light-emitting material is one or more compounds of Formula (I) or (II). In some embodiments, for the organic electroluminescent device and the organic photoluminescent device to exhibit a high light emission efficiency, the singlet excitons and the triplet excitons generated in the light-emitting material are confined in the light-emitting material. In some embodiments, a host material is used in addition to the light-emitting material in the light-emitting layer. In some embodiments, the host material is an organic compound. In some embodiments, the organic compounds have excited singlet energy and excited triplet energy, at least one of which is higher than those of the light-emitting material of the invention. In some embodiments, the singlet excitons and the triplet excitons generated in the light-emitting material of the invention are confined in the molecules of the light-emitting material of the invention. In some embodiments, the singlet and triplet excitons are sufficiently confined to elicit the light emission efficiency. In some embodiments, the singlet excitons and the triplet excitons are not confined sufficiently, though a high light emission efficiency is still obtained, and thus a host material capable of achieving a high light emission efficiency can be used in the invention without any particular limitation. In some embodiments, the light emission occurs in the light-emitting material of the light-emitting layer in the devices of the invention. In some embodiments, the emitted light contains both fluorescent light and delayed fluorescent light. In some embodiments, the emitted light comprises emitted light from the host material. In some embodiments, the emitted light consists of emitted light from the host material. In some embodiments, the emitted light comprises emitted light from a compound of Formula (I) or (II), and emitted light from the host material. In some embodiments, a TADF molecule and a host material are used. In some embodiments, the TADF is an assistant dopant.

In some embodiments, when a host material is used, the amount of the compound of the invention as the light-emitting material contained in the light-emitting layer is 0.1% by weight or more. In some embodiments, when a host material is used, the amount of the compound of the invention as the light-emitting material contained in the light-emitting layer is 1% by weight or more. In some embodiments, when a host material is used, the amount of the compound of the invention as the light-emitting material contained in the light-emitting layer is 50% by weight or less. In some embodiments, when a host material is used, the amount of the compound of the invention as the light-emitting material contained in the light-emitting layer is 20% by weight or less. In some embodiments, when a host material is used, the amount of the compound of the invention as the light-emitting material contained in the light-emitting layer is 10% by weight or less.

In some embodiments, the host material in the light-emitting layer is an organic compound comprising a hole transporting function and an electron transporting function. In some embodiments, the host material in the light-emitting layer is an organic compound that prevents the emitted light from being increased in wavelength. In some embodiments, the host material in the light-emitting layer is an organic compound with a high glass transition temperature.

In some embodiments, the host material is selected from the group consisting of:

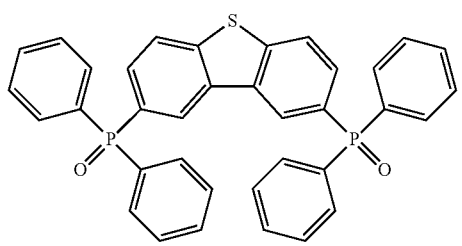

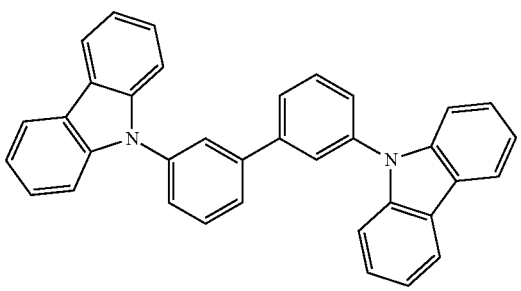

-continued
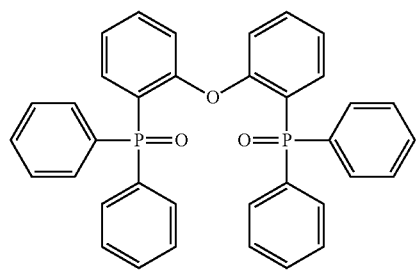
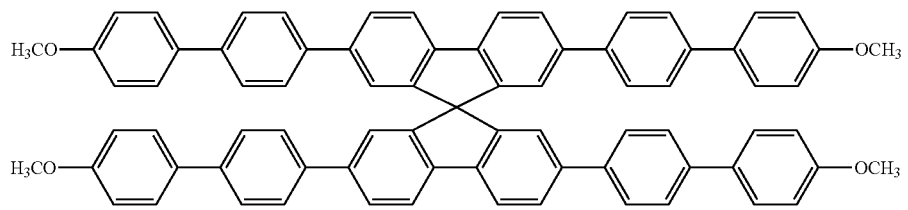
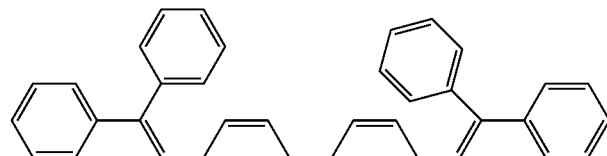
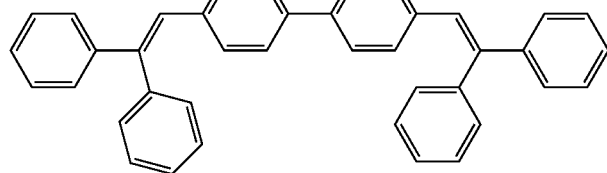
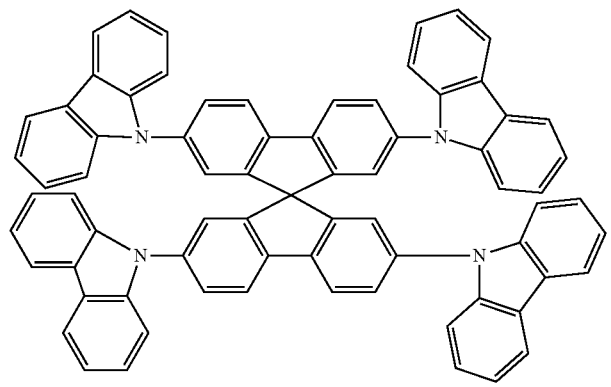
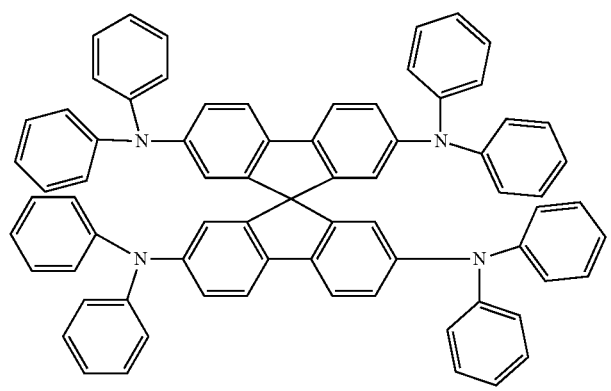

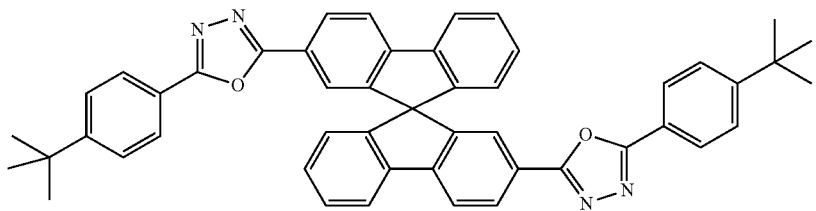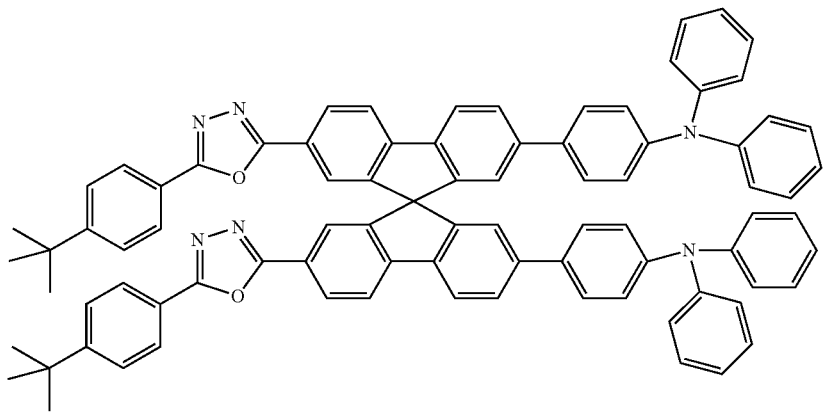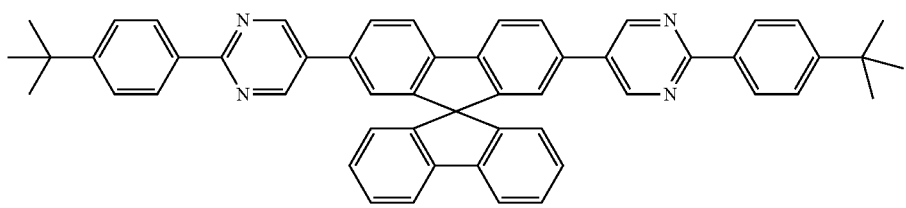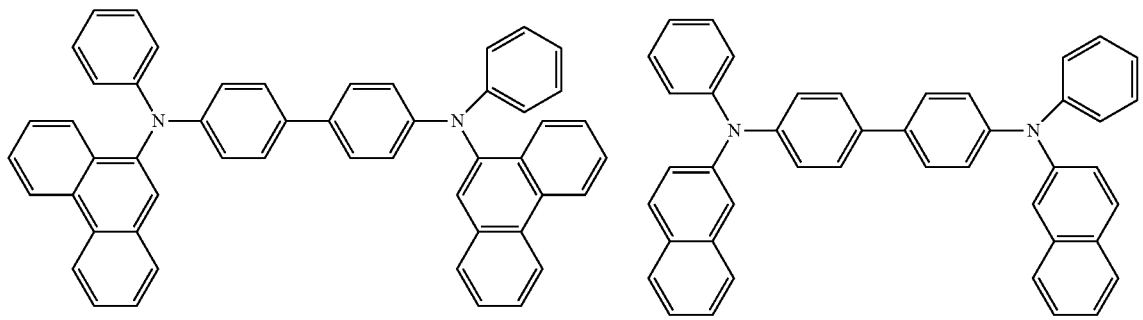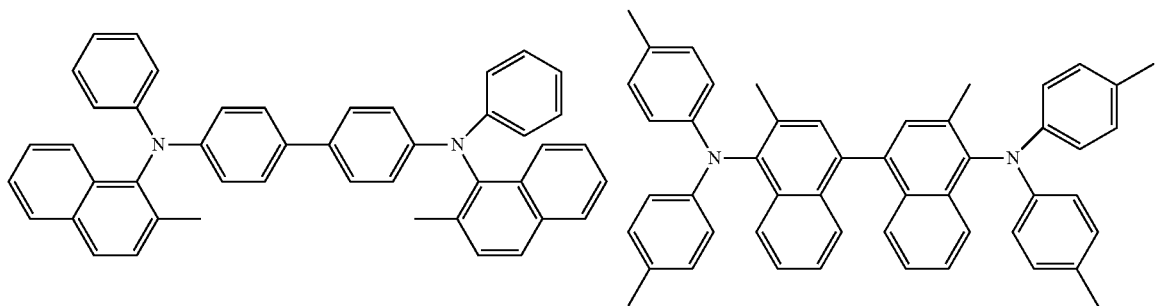

-continued
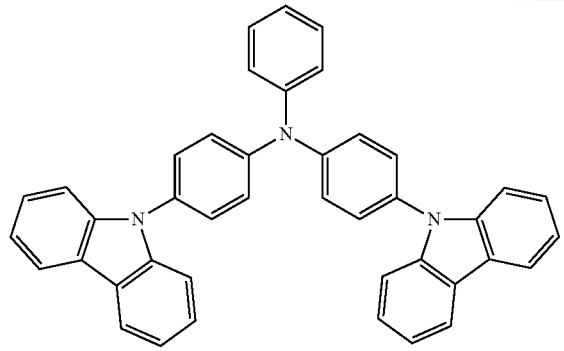
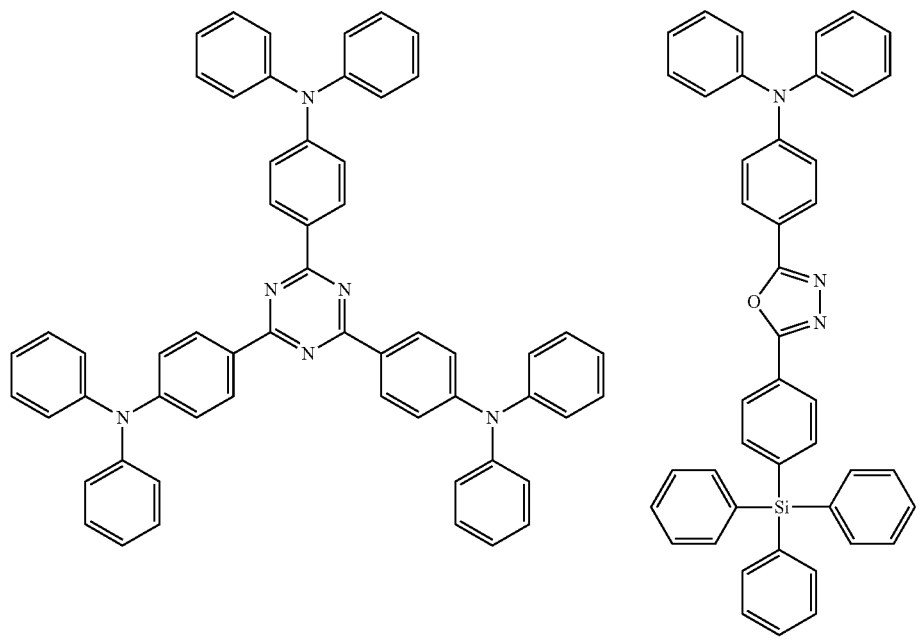
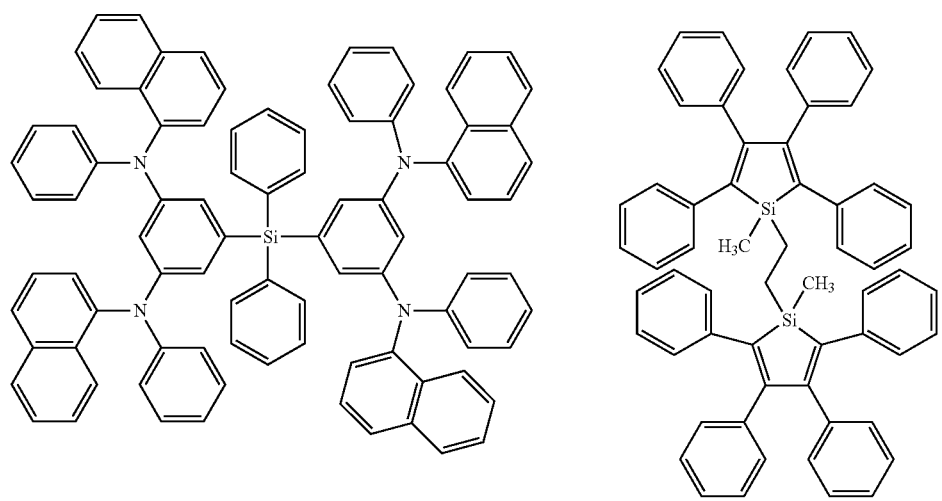

81
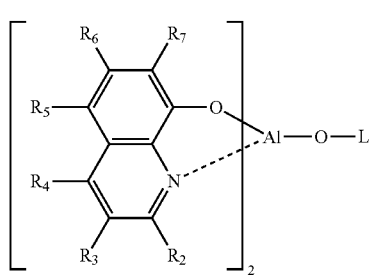
82
-continued
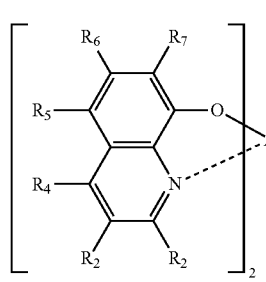
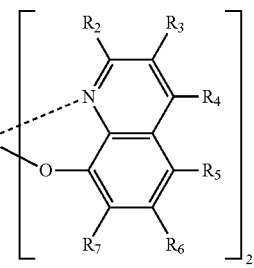
$R_2$-$R_7$ = H or substituent
L = Ligand
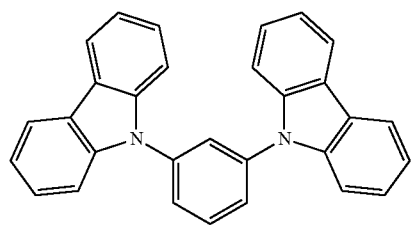
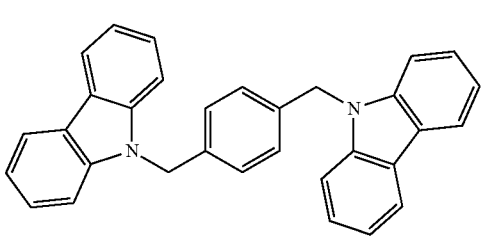
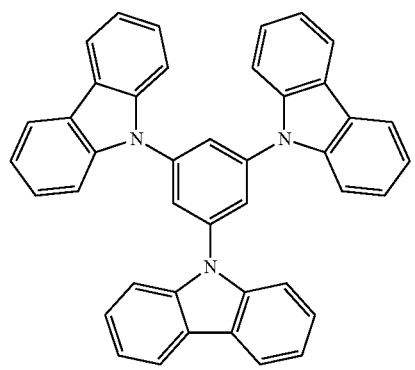
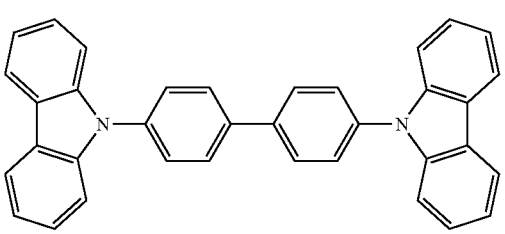
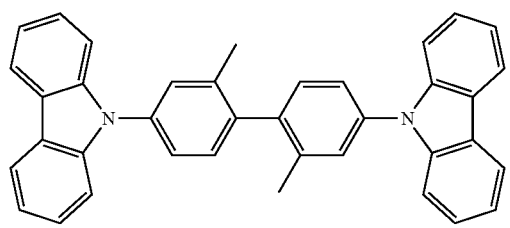
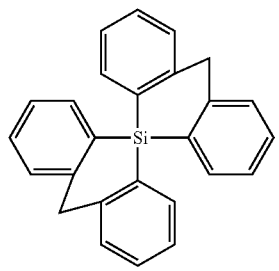
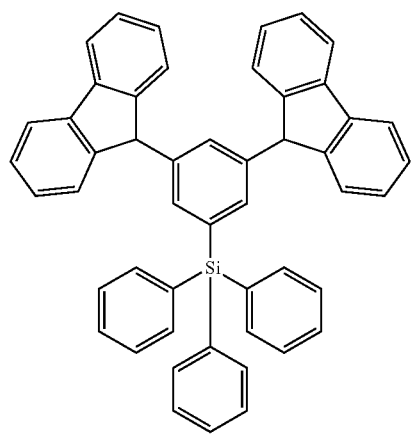
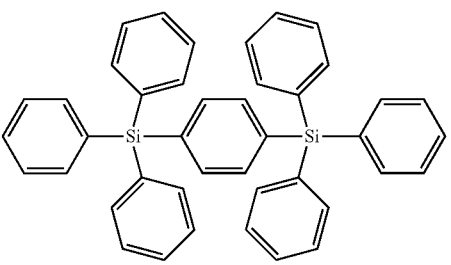

83
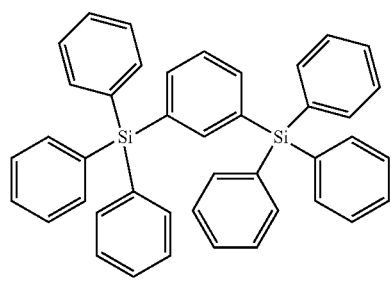
-continued
84
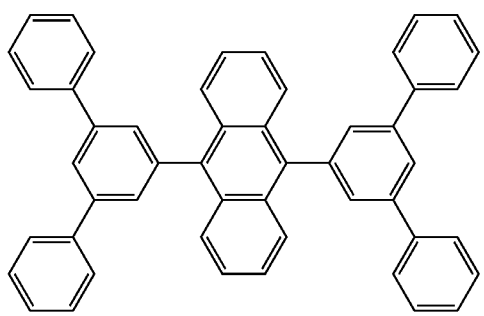
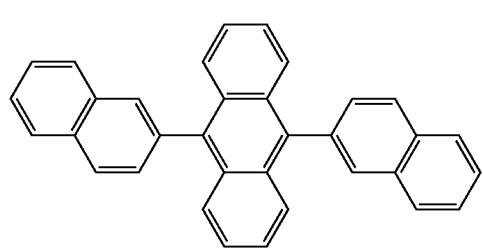
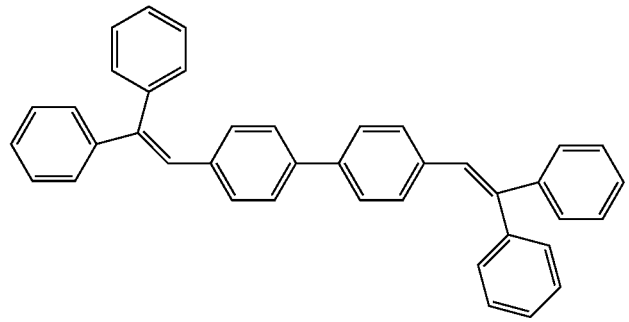
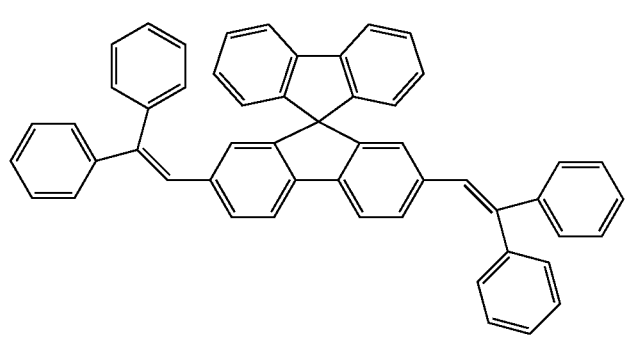
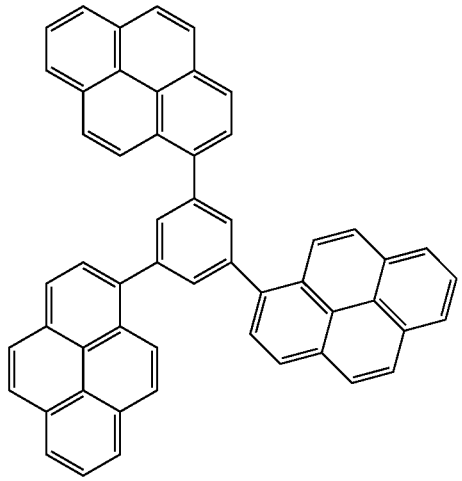

-continued
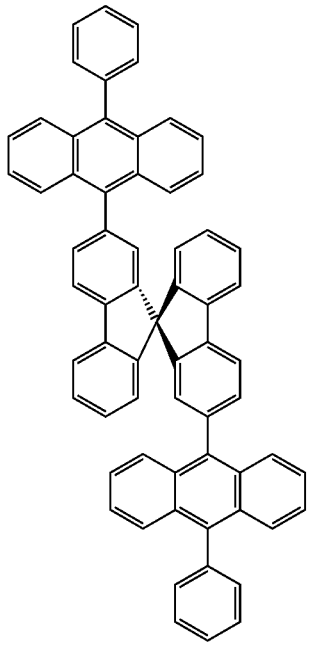
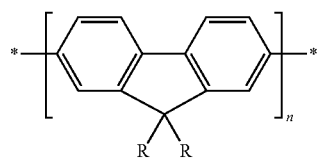
R = alkyl, aryl
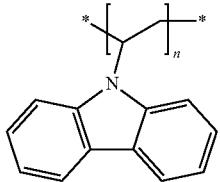
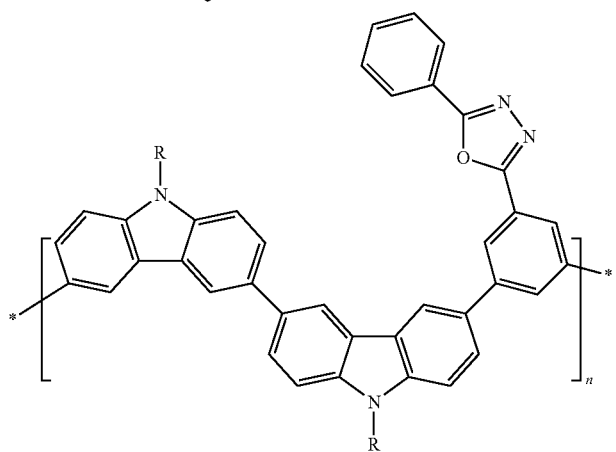
R = alkyl, aryl
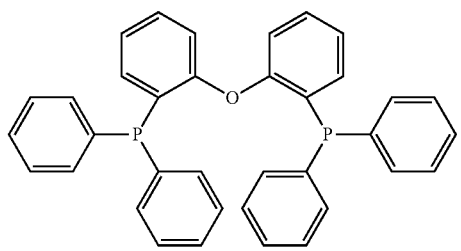
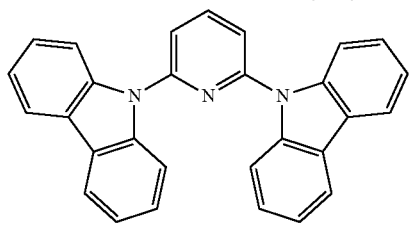
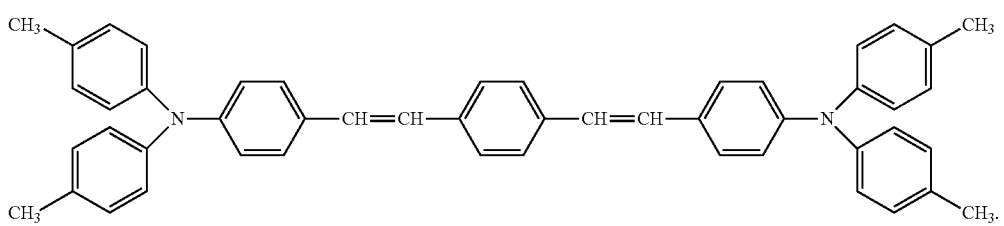

Injection Layer

An injection layer is a layer between the electrode and the organic layer. In some embodiments, the injection layer decreases the driving voltage and enhances the light emission luminance. In some embodiments, the injection layer includes a hole injection layer and an electron injection layer. The injection layer can be positioned between the anode and the light-emitting layer or the hole transporting layer, and between the cathode and the light-emitting layer or the electron transporting layer. In some embodiments, an injection layer is present. In some embodiments, no injection layer is present.

Barrier Layer

A barrier layer is a layer capable of inhibiting charges (electrons or holes) and/or excitons present in the light-emitting layer from being diffused outside the light-emitting layer. In some embodiments, the electron barrier layer is between the light-emitting layer and the hole transporting layer, and inhibits electrons from passing through the light-emitting layer toward the hole transporting layer. In some embodiments, the hole barrier layer is between the light-emitting layer and the electron transporting layer, and inhibits holes from passing through the light-emitting layer toward the electron transporting layer. In some embodiments, the barrier layer inhibits excitons from being diffused outside the light-emitting layer. In some embodiments, the electron barrier layer and the hole barrier layer are exciton barrier layers. As used herein, the term "electron barrier layer" or "exciton barrier layer" includes a layer that has the functions of both electron barrier layer and of an exciton barrier layer.

Hole Barrier Layer

A hole barrier layer acts as an electron transporting layer. In some embodiments, the hole barrier layer inhibits holes from reaching the electron transporting layer while transporting electrons. In some embodiments, the hole barrier layer enhances the recombination probability of electrons and holes in the light-emitting layer. The material for the hole barrier layer may be the same materials as the ones described for the electron transporting layer.

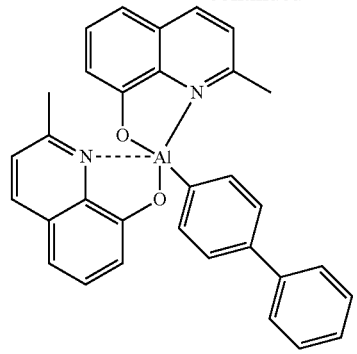

-continued

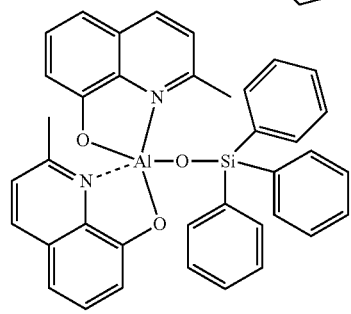

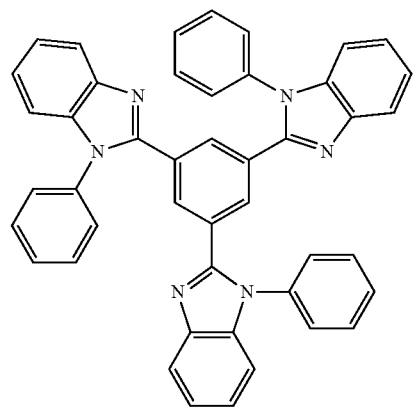

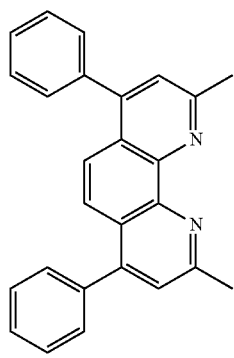

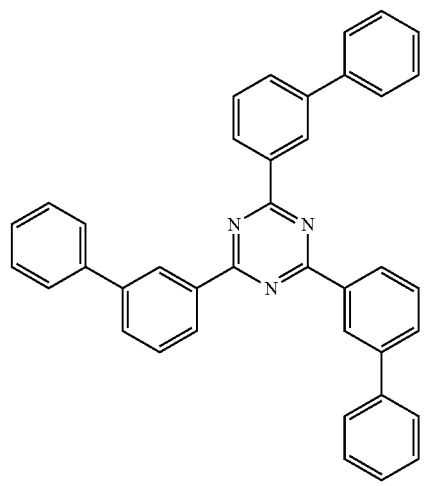

-continued

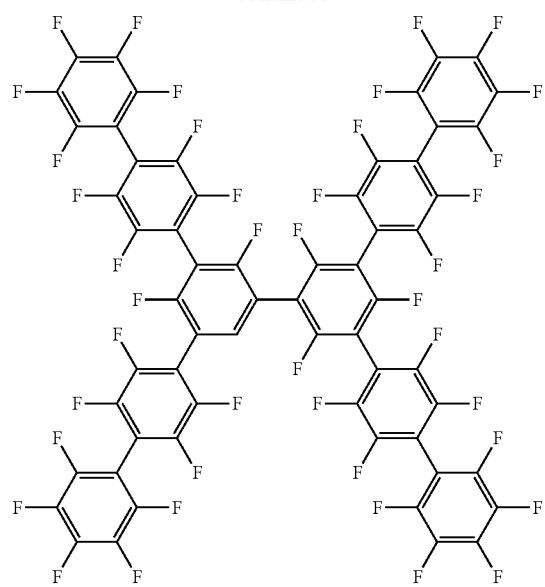

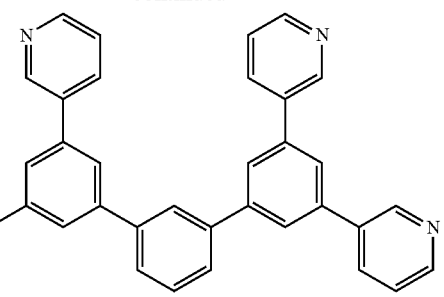

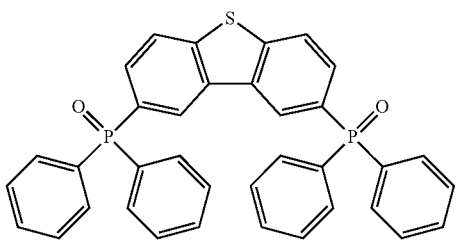

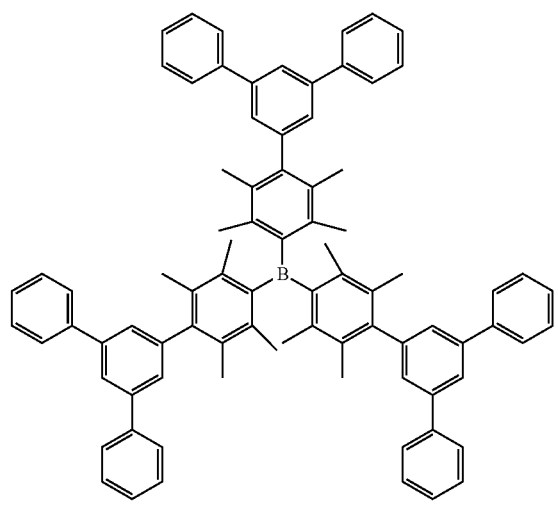

Electron Barrier Layer

As electron barrier layer transports holes. In some embodiments, the electron barrier layer inhibits electrons from reaching the hole transporting layer while transporting holes. In some embodiments, the electron barrier layer enhances the recombination probability of electrons and holes in the light-emitting layer. Next, preferred examples of compounds usable as an electron barrier material are mentioned below.

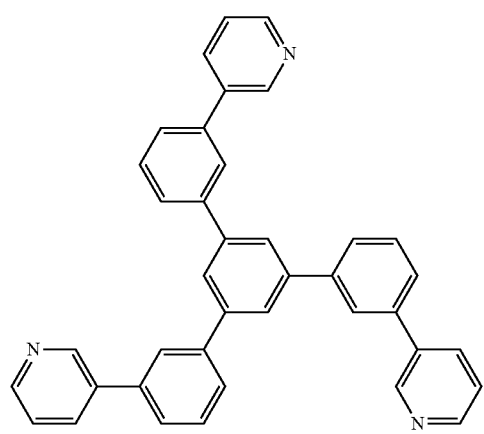

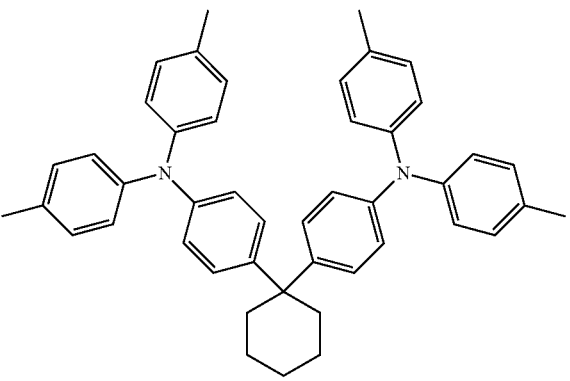

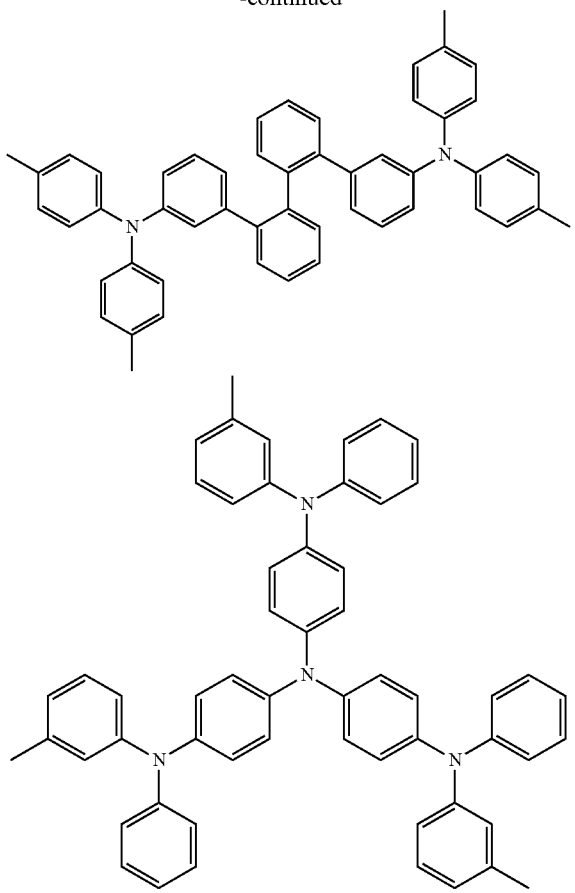

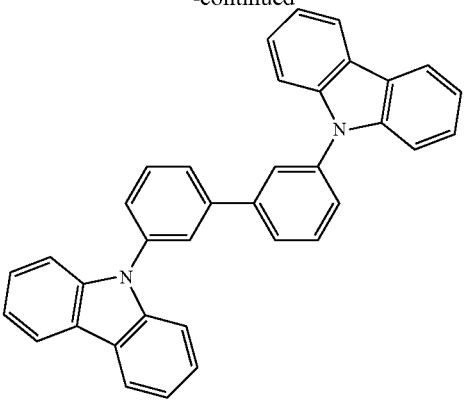

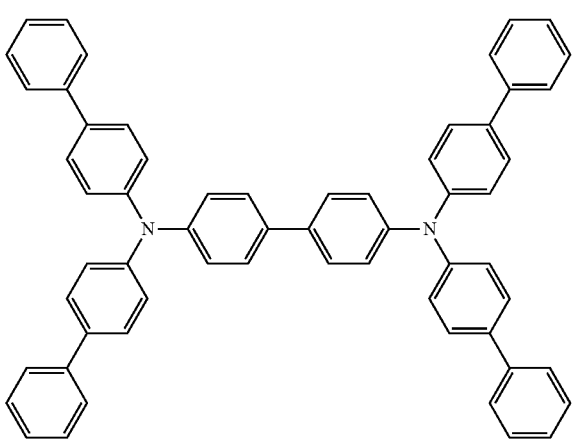

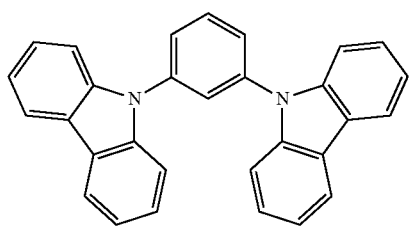

Exciton Barrier Layer

An exciton barrier layer inhibits excitons generated through recombination of holes and electrons in the light-emitting layer from being diffused to the charge transporting layer. In some embodiments, the exciton barrier layer enables effective confinement of excitons in the light-emitting layer. In some embodiments, the light emission efficiency of the device is enhanced. In some embodiments, the exciton barrier layer is adjacent to the light-emitting layer on any of the side of the anode and the side of the cathode, and on both the sides. In some embodiments, where the exciton barrier layer is on the side of the anode, the layer can be between the hole transporting layer and the light-emitting layer and adjacent to the light-emitting layer. In some embodiments, where the exciton barrier layer is on the side of the cathode, the layer can be between the light-emitting layer and the cathode and adjacent to the light-emitting layer. In some embodiments, a hole injection layer, an electron barrier layer, or a similar layer is between the anode and the exciton barrier layer that is adjacent to the light-emitting layer on the side of the anode. In some embodiments, a hole injection layer, an electron barrier layer, a hole barrier layer, or a similar layer is between the cathode and the exciton barrier layer that is adjacent to the light-emitting layer on the side of the cathode. In some embodiments, the exciton barrier layer comprises excited singlet energy and excited triplet energy, at least one of which is higher than the excited singlet energy and the excited triplet energy of the light-emitting material, respectively.

Hole Transporting Layer

The hole transporting layer comprises a hole transporting material. In some embodiments, the hole transporting layer is a single layer. In some embodiments, the hole transporting layer comprises a plurality of layers.

In some embodiments, the hole transporting material has one of injection or transporting property of holes and barrier property of electrons. In some embodiments, the hole transporting material is an organic material. In some embodiments, the hole transporting material is an inorganic material. Examples of known hole transporting materials that may be used herein include but are not limited to a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer, or a combination thereof. In some embodiments, the hole transporting material is selected from a porphyrin compound, an aromatic tertiary amine compound, and a styrylamine compound. In some embodiments, the hole transporting material is an aromatic tertiary amine compound. Next, preferred examples of compounds usable as a hole transport material are mentioned below.

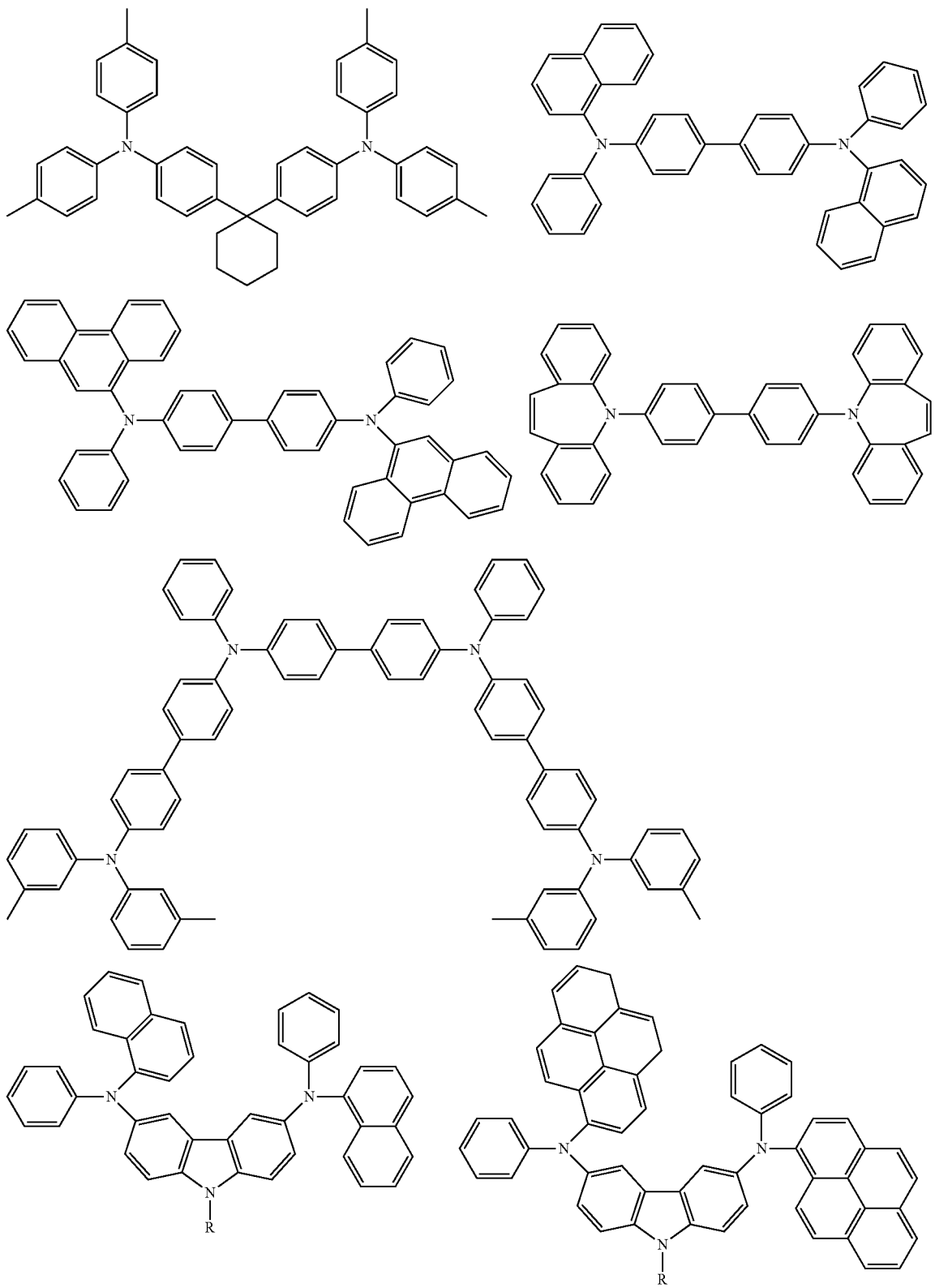

95
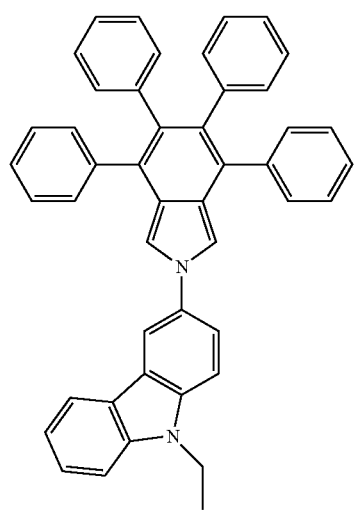
96
-continued
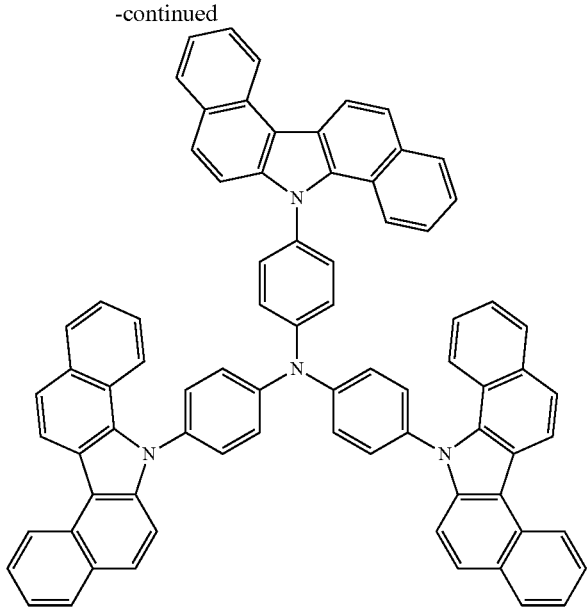
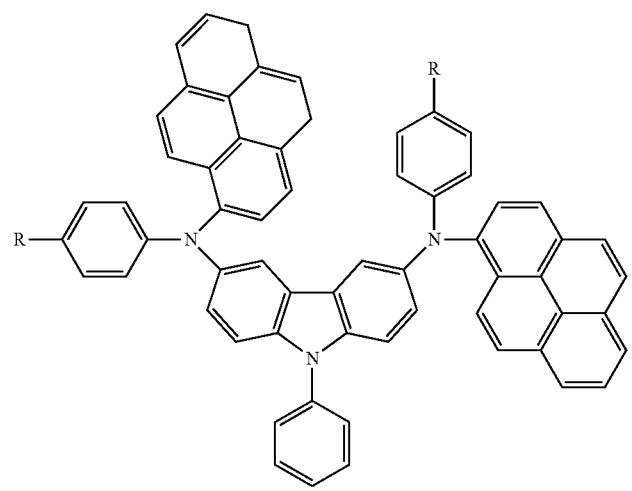
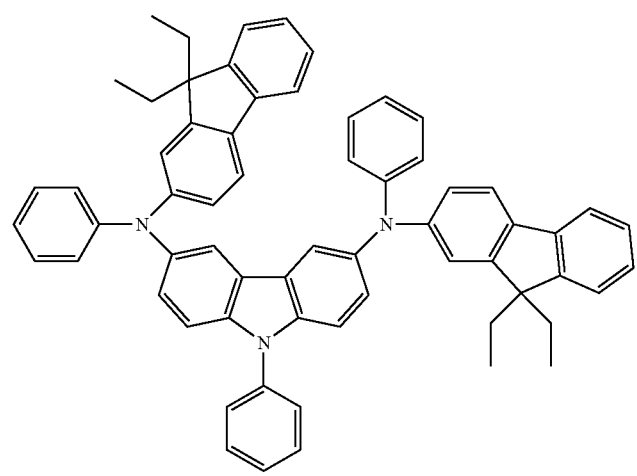

-continued
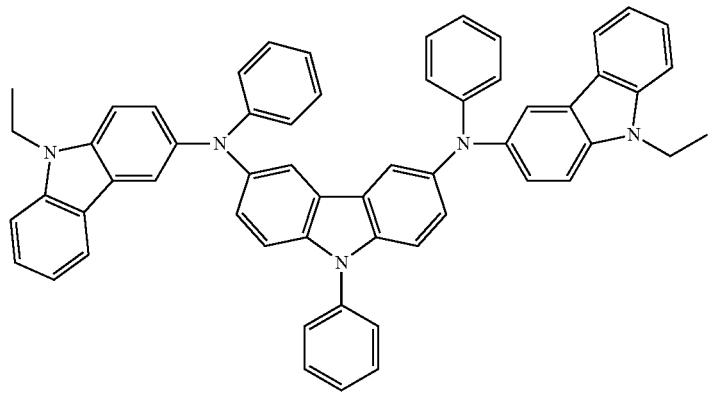
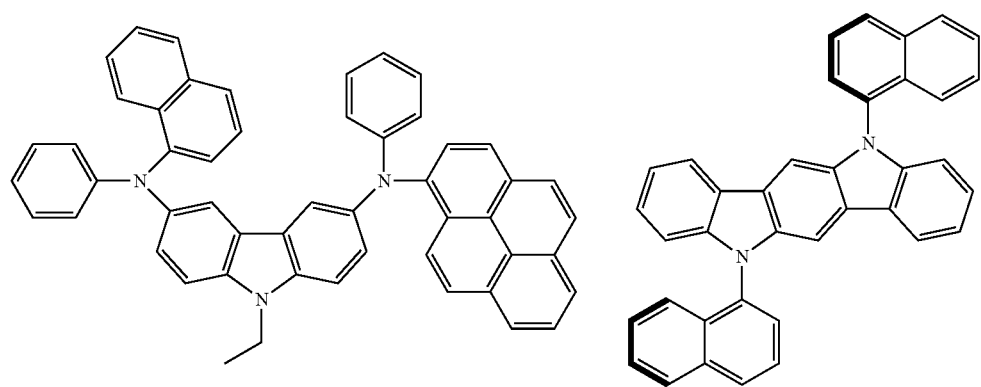
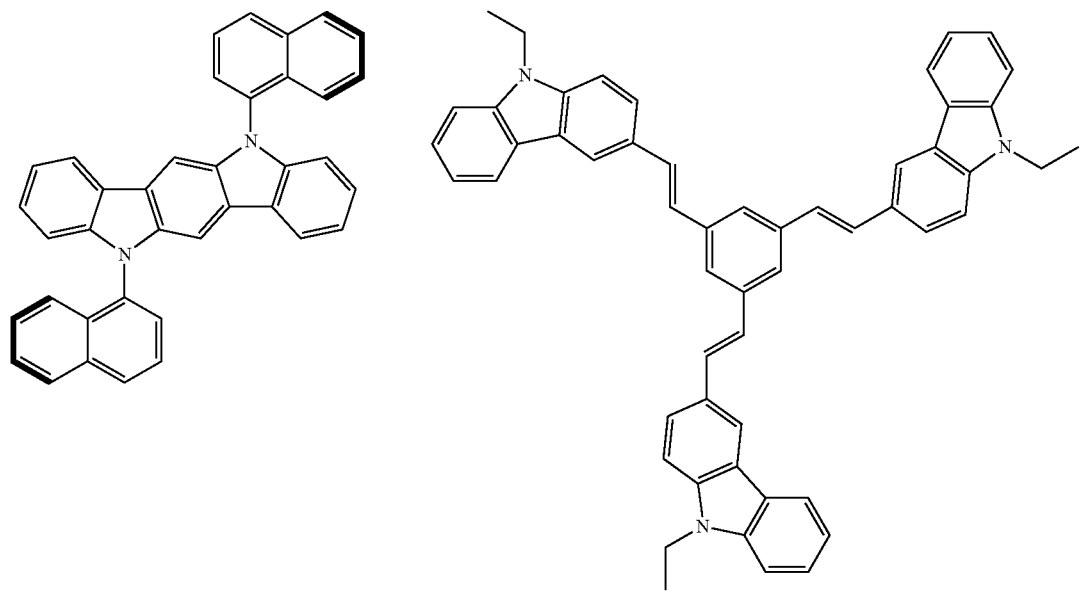

-continued
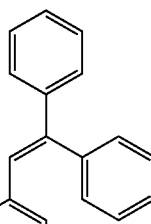
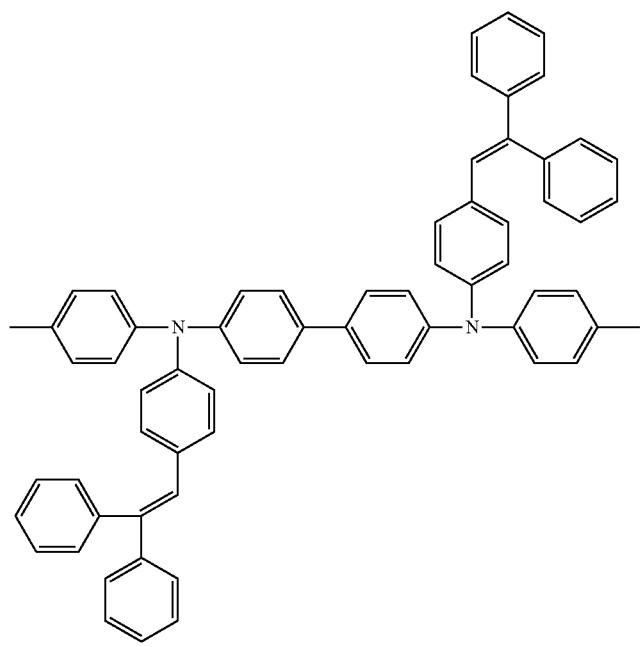
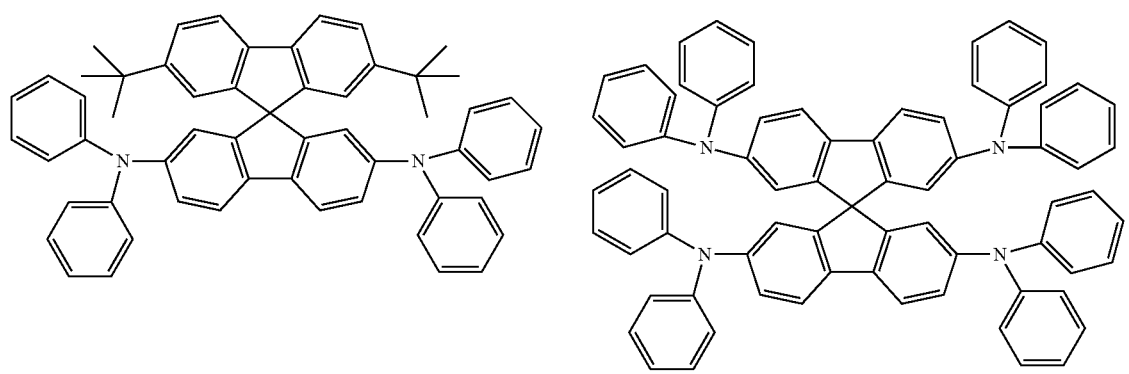
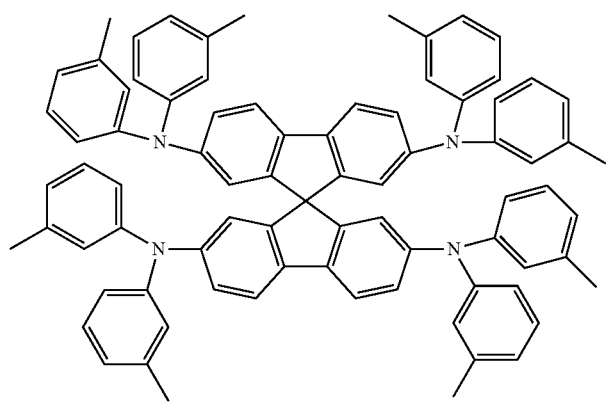

-continued
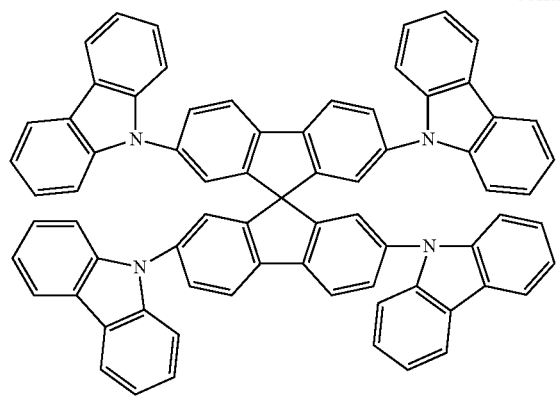
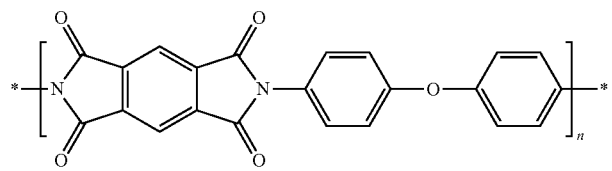
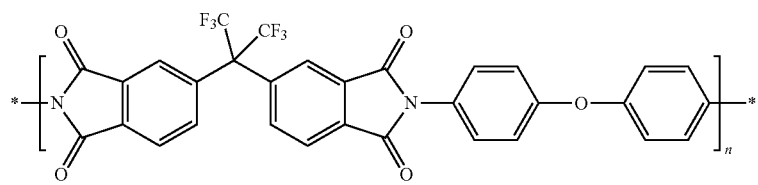
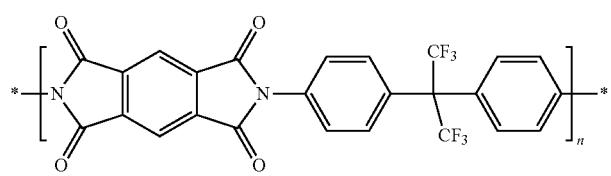
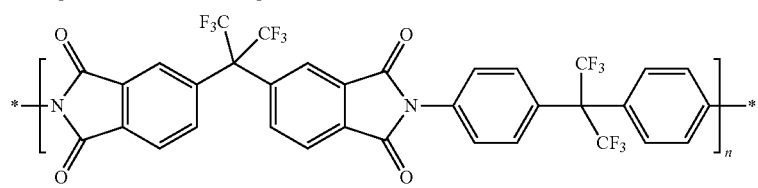
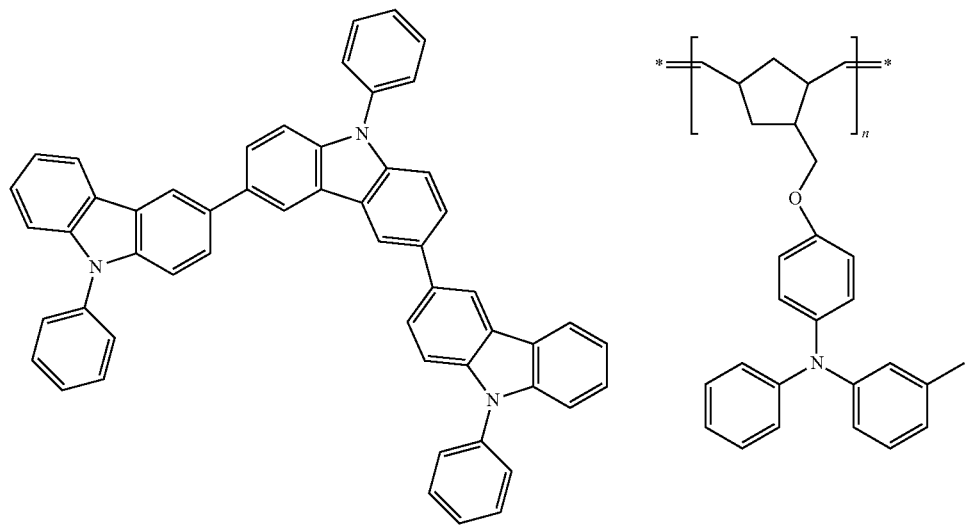

-continued
103
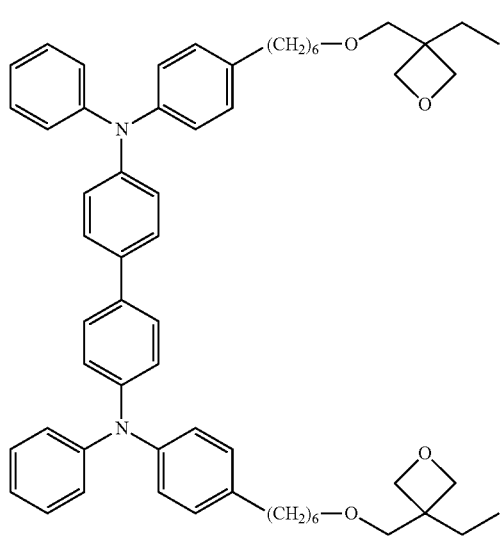
104
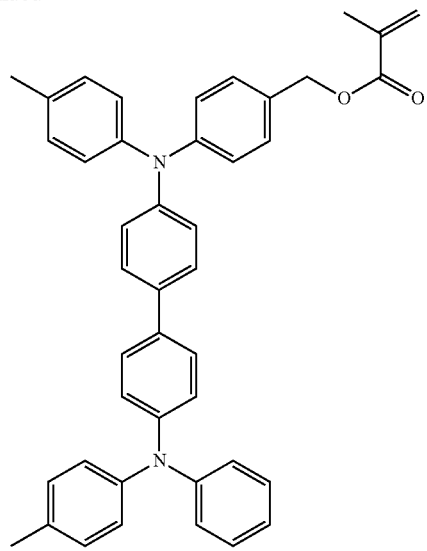
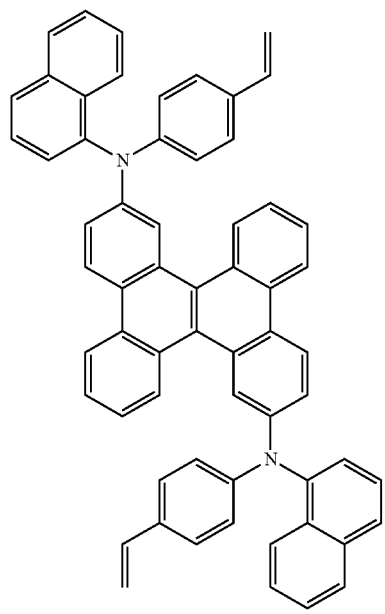
R =
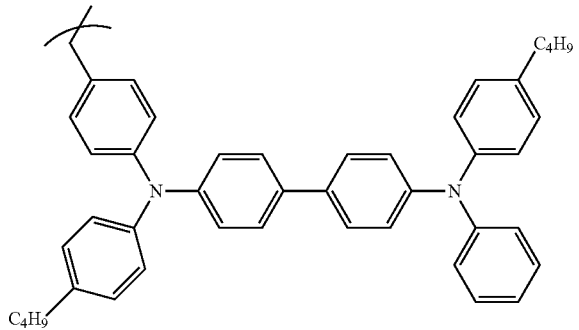
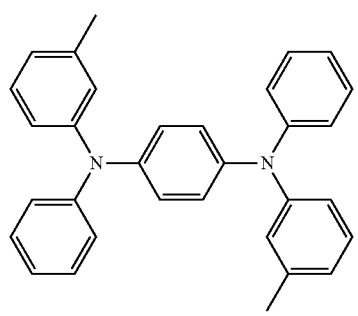
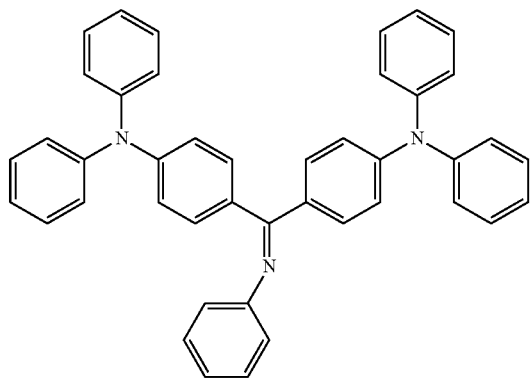

-continued
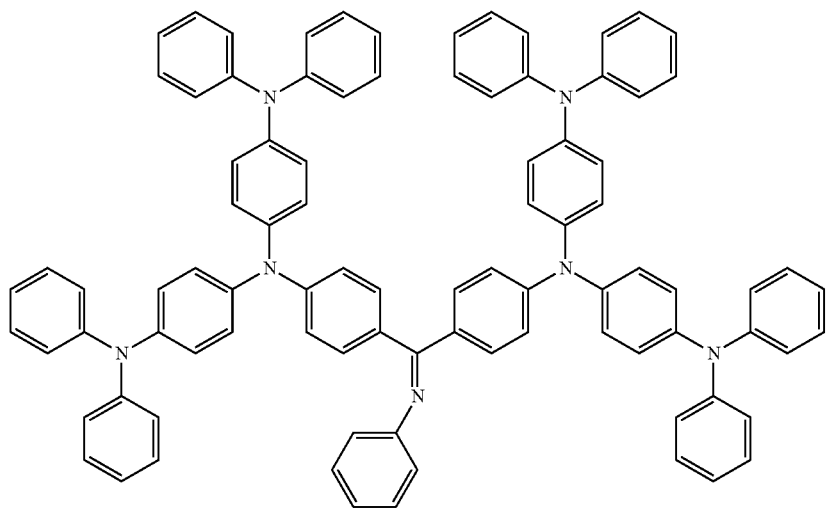
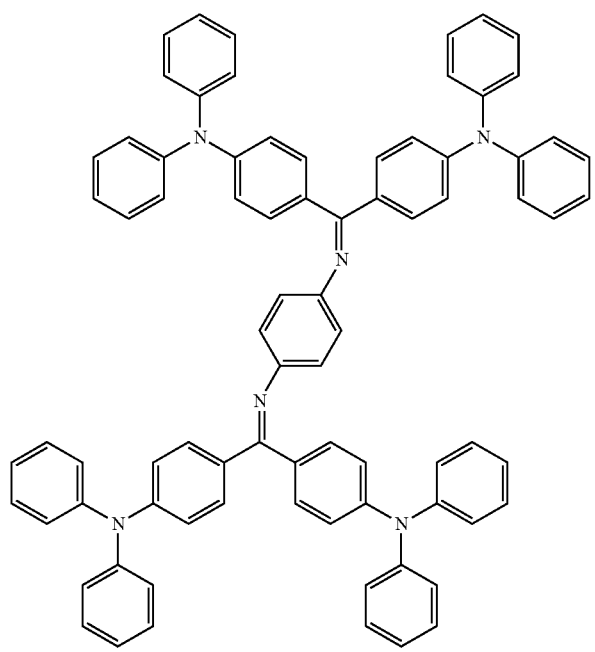

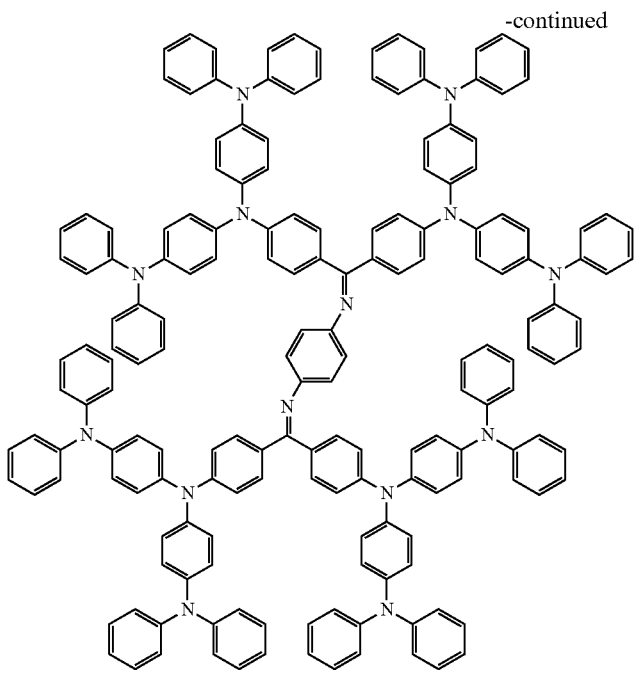

Electron Transporting Layer

The electron transporting layer comprises an electron transporting material. In some embodiments, the electron transporting layer is a single layer. In some embodiments, the electron transporting layer comprises a plurality of layer.

In some embodiments, the electron transporting material needs only to have a function of transporting electrons, which are injected from the cathode, to the light-emitting layer. In some embodiments, the electron transporting material also function as a hole barrier material. Examples of the electron transporting layer that may be used herein include but are not limited to a nitro-substituted fluorene derivative, a diphenylquinone derivative, a thiopyran dioxide derivative, carbodiimide, a fluorenylidene methane derivative, anthraquinodimethane, an anthrone derivatives, an oxadiazole derivative, an azole derivative, an azine derivative, or a combination thereof, or a polymer thereof. In some embodiments, the electron transporting material is a thiadiazole derivative, or a quinoxaline derivative. In some embodiments, the electron transporting material is a polymer material. Next, preferred examples of compounds usable as an electron transport material are mentioned below.

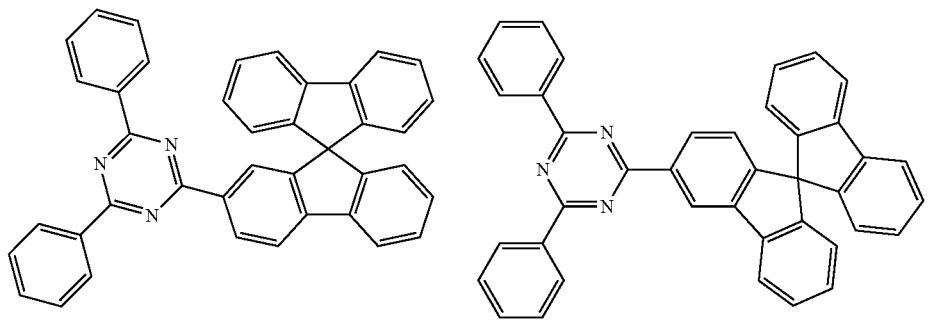

-continued
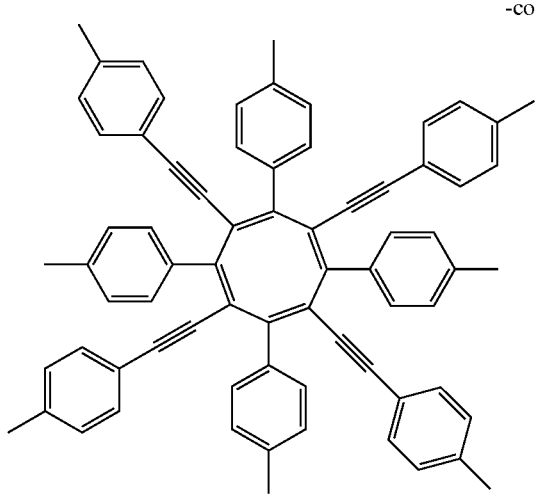
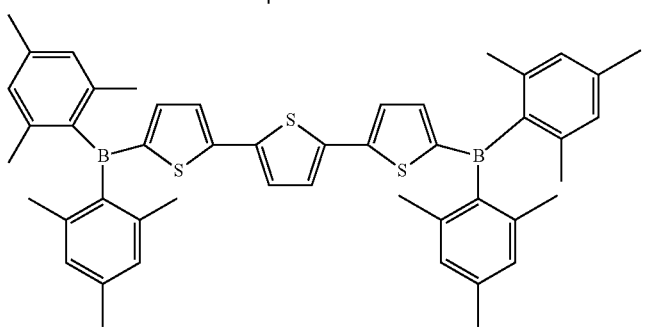
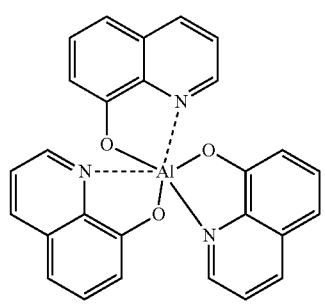
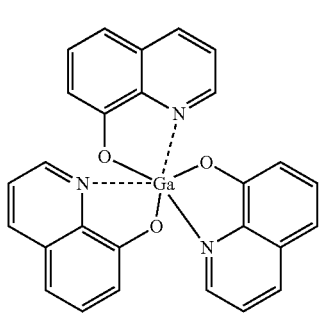
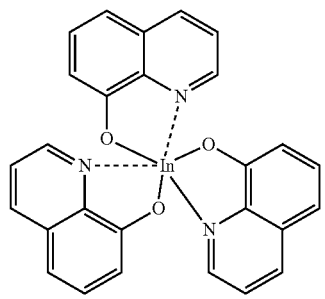
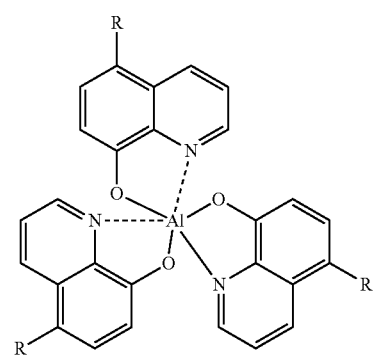
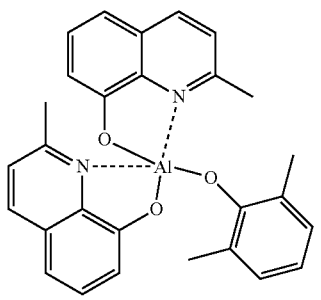
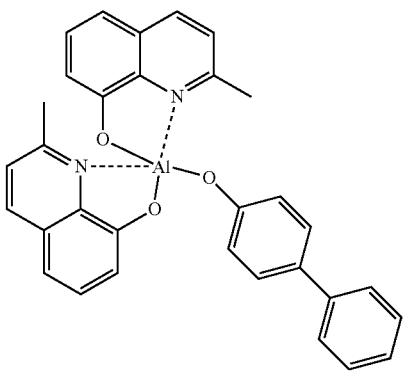

-continued
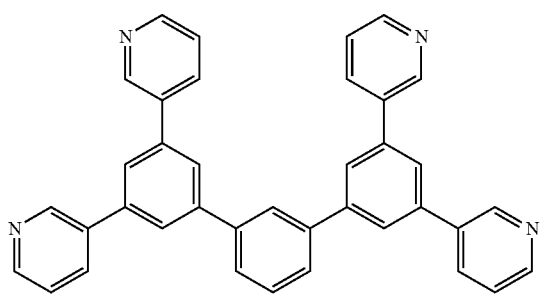
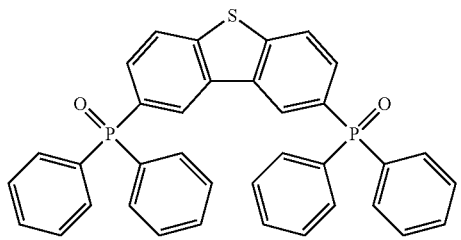
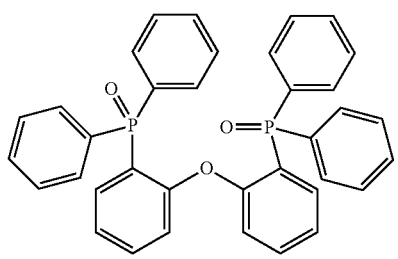
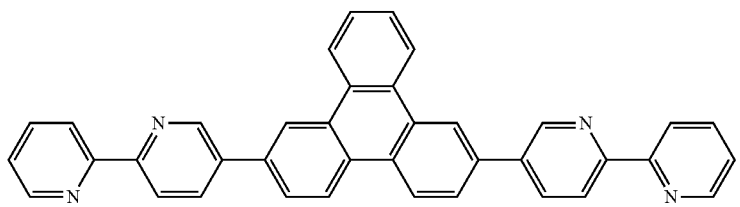
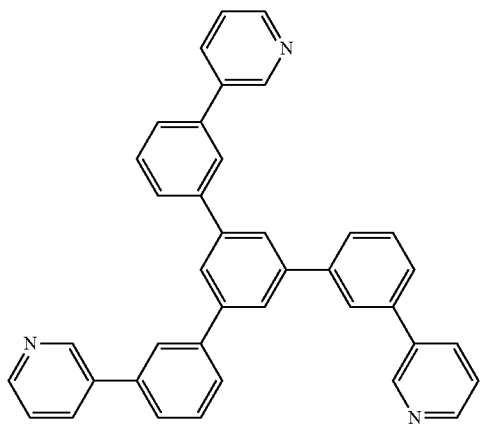
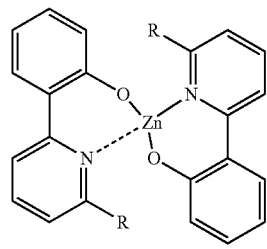
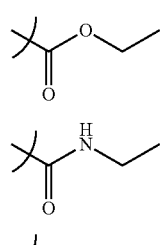
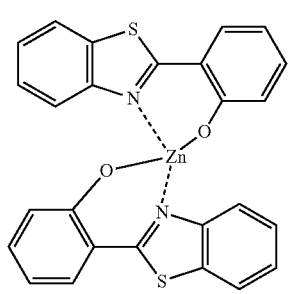
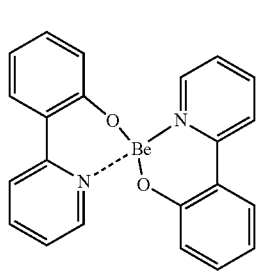
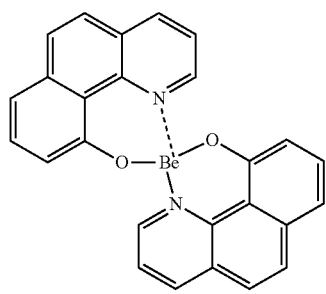

113
-continued
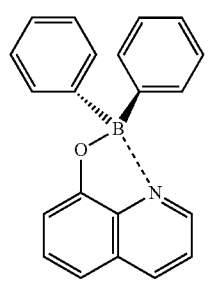 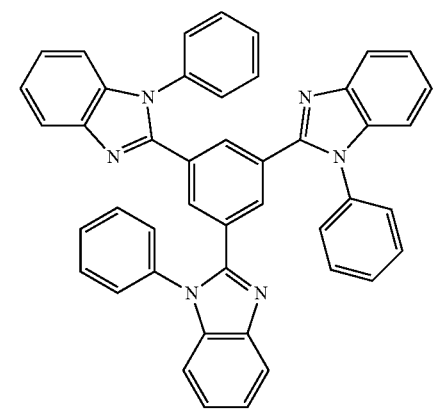
114
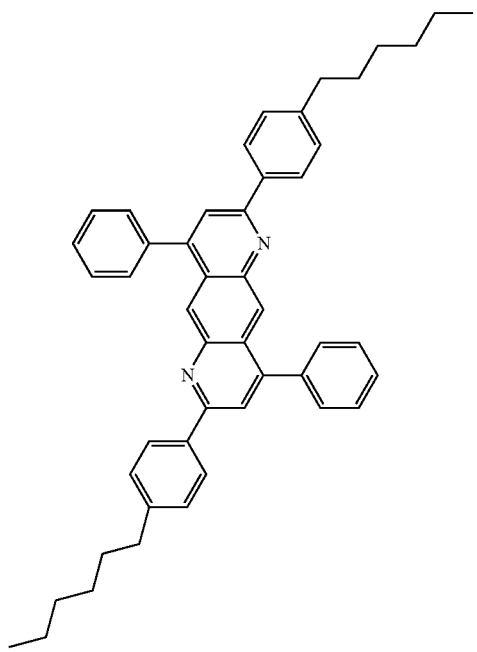
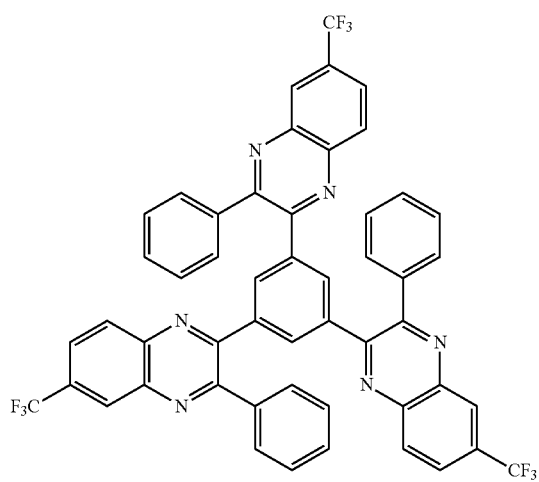
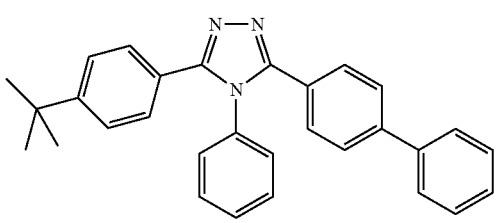
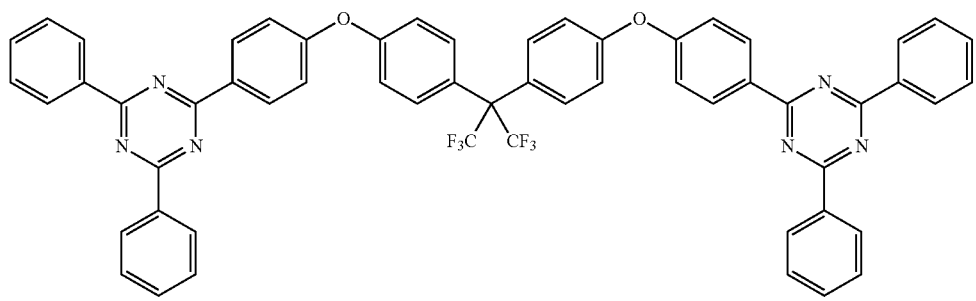
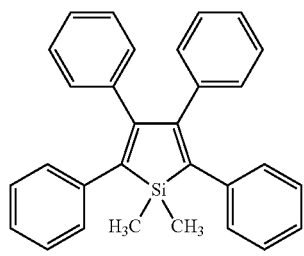 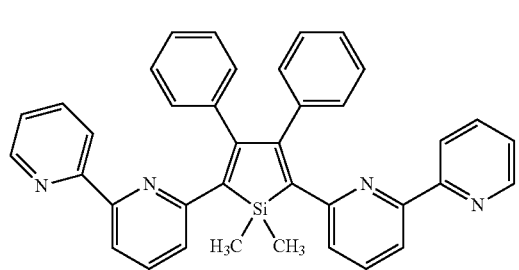

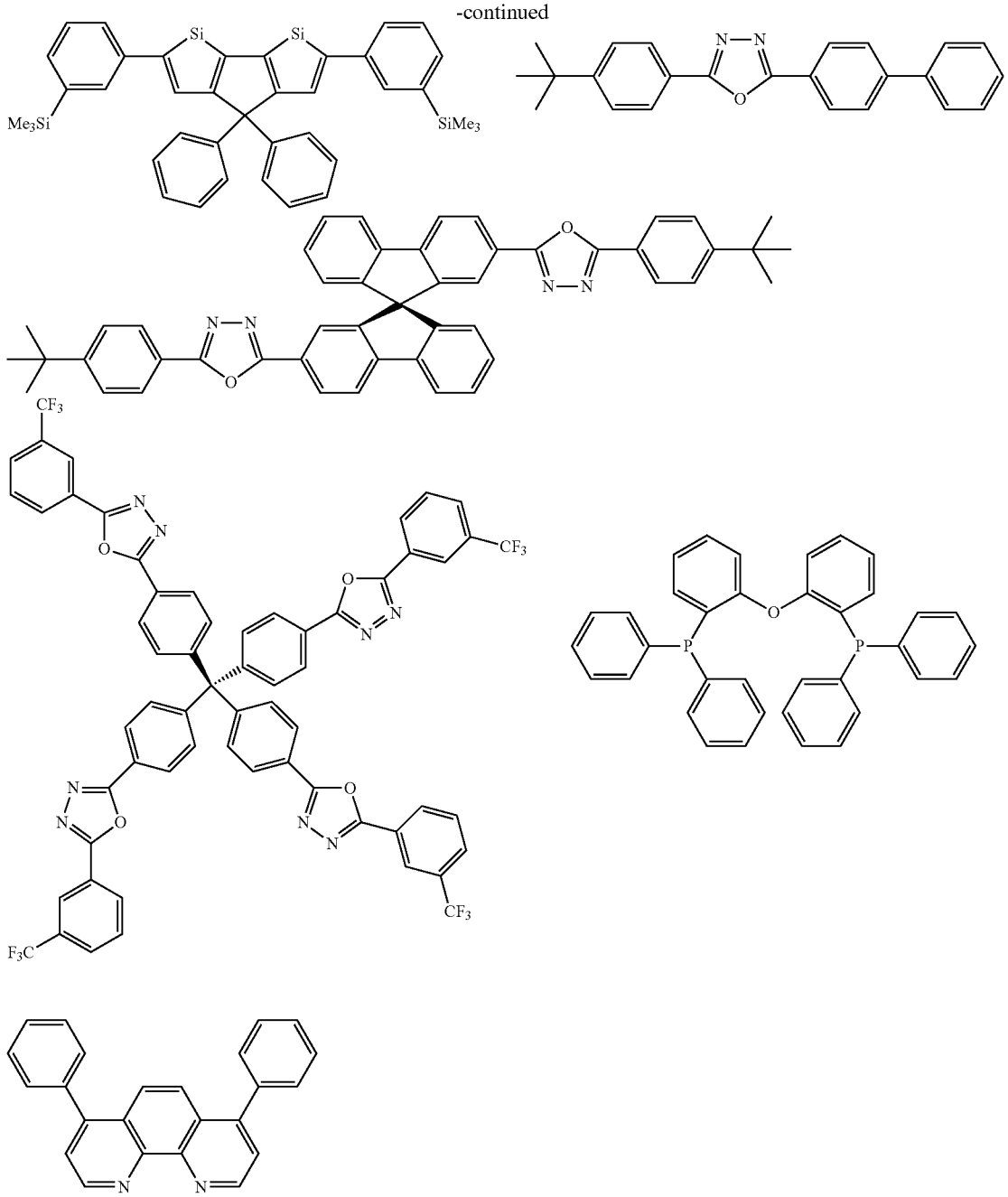

Molecular Weight

The molecular weight of the compound represented by the Formula (I) or (II) is, for example, in the case of using it by forming an organic layer that contains a compound represented by the Formula (I) or (II) according to a vapor deposition method, preferably 1500 or less, more preferably 1200 or less, even more preferably 1000 or less, still more preferably 900 or less.

Polymer

Compounds of Formula (I) or (II) may be formed into a film according to a coating method irrespective of the molecular weight of the compound. Accordingly, even a compound having a relatively large molecular weight can be formed into a film.

In some embodiments, a film comprises a plurality of independently selected compounds of Formula (I) or (II). In some embodiments, a compound of Formula (I) or (II) is modified to incorporate a polymerizable group. The modified compound is then polymerized to obtain a polymer comprising a compound of Formula (I) or (II). For example, a monomer is obtained by replacing any one of the hydrogen of a compound of Formula (I) or (II) by a polymerizable functional group. The monomer is then homo-polymerized or copolymerized with any other monomer to give a polymer having a repeating unit. Alternatively, different compounds of Formula (I) or (II) are coupled to give a dimer or a trimer. Examples of the polymer having a repeating unit comprising a compound of Formula (I) or (II) include polymers comprising a unit of Formula (A) or (B).

Formula (A)

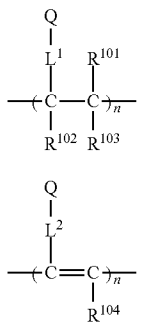

Formula (B)

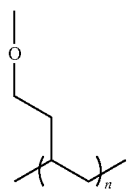

wherein:

Q represents a group containing a compound of Formula (I) or (II);

$L^1$ and $L^2$ each represents a linking group; and $R^{101}$, $R^{102}$, $R^{103}$ and $R^{104}$ each independently represent a substituent.

In some embodiments, the linking group is preferably 0 to 20 carbons, more preferably 1 to 15, even more preferably 2 to 10. In some embodiments, the linking is $-X^{11}-L^{11}-$; wherein $X^{11}$ is oxygen or sulphur, and $L^{11}$ represents a linking group.

In some embodiments, $X^{11}$ is oxygen. In some embodiments, $L^{11}$ is a substituted or unsubstituted alkylene or a substituted or unsubstituted arylene. In some embodiments, the substituted or unsubstituted alkylene is C1 to C10 alkylene. In some embodiments, substituted or unsubstituted arylene is substituted or unsubstituted phenylene.

In some embodiments, $R^{101}$, $R^{102}$, $R^{103}$ and $R^{104}$ are independently a substituted or unsubstituted alkyl group having 1 to 6 carbon atoms, a substituted or unsubstituted alkoxy group having 1 to 6 carbon atoms, or a halogen atom. In some embodiments, $R^{101}$, $R^{102}$, $R^{103}$ and $R^{104}$ are independently unsubstituted alkyl having 1 to 3 carbon atoms, an unsubstituted alkoxy having 1 to 3 carbon atoms, a fluorine atom or a chlorine atom. In some embodiments, $R^{101}$, $R^{102}$, $R^{103}$ and $R^{104}$ are independently unsubstituted alkyl group having 1 to 3 carbon atoms, or an unsubstituted alkoxy group having 1 to 3 carbon atoms.

$L^1$ and $L^2$ may be introduced by replacing any one of the hydrogen in the structure of the Formula (I) or (II). Two or more linking groups may bond to one Q to form a cross-linked structure or a network structure.

Specific structural examples of the repeating unit include structures represented by the following Formulae (C) to (F).

Formula (C)

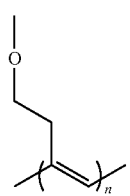

Formula (D)

Formula (E)

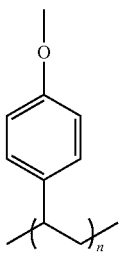

Formula (F)

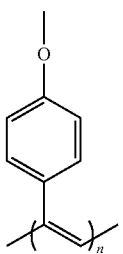

Polymers having a repeating unit of the Formulae (C) to (F) may be synthesized by replacing any one of the hydrogen by a hydroxy group into a structure of the Formula (I) or (II), then introducing a polymerizable group into the structure through reaction with any of the following compounds via the hydroxy group serving as a linker, and polymerizing the polymerizable group.

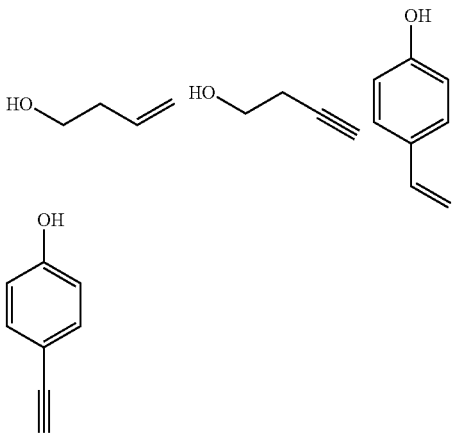

The polymer having a structure represented by the Formula (I) or (II) may be a polymer containing a repeating unit alone having a structure represented by the Formula (I) or (II) or may be a polymer containing a repeating unit having any other structure. The repeating unit having a structure represented by the Formula (I) or (II) contained in the polymer may be one type alone or may contain two or more types of repeating units. A repeating unit not having a structure represented by the Formula (I) or (II) includes those derived from monomers to be used in ordinary copolymerization. For example, there are mentioned repeating units derived from monomers having an ethylenic unsaturated bond such as ethylene, styrene, etc.

In some embodiments, a compound of Formula (I) or (II) is comprised in the light-emitting layer of a device of the invention. In some embodiments, a compound of Formula (I) or (II) is comprised in the light-emitting layer and at least one other layers. In some embodiments, the compounds of Formula (I) or (II) are independently selected for each layers. In some embodiments, the compounds of Formula (I) or (II) are the same. In some embodiments, the compounds of Formula (I) or (II) are different. For example, the compound represented by the Formula (I) or (II) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any dry processes and/or wet processes.

Specific examples of materials that can be used in the organic electroluminescent device are shown above, but the materials that may be used in the invention are not construed as being limited to the example compounds. In some embodiments, a material having a particular function can also have another function.

Film Forming Method

The compound of the invention may be formed as a film on a substrate by any methods.

Before forming the film, the substrate may be heated or cooled, and the film quality and the molecular packing in the film may be controlled by changing the temperature of the substrate. The temperature of the substrate is not particularly limited, and is preferably in a range of 0 to 200° C., more preferably in a range of 15 to 100° C., and particularly preferably in a range of 20 to 95° C.

Before forming a film of the compound of the invention on a substrate, the film may be formed by a vacuum process or a solution process, both of which are preferred.

Specific examples of the film formation by a vacuum process include a physical vapor deposition, such as vacuum deposition, sputtering method, ion plating method and molecular beam epitaxy (MBE), and chemical vapor deposition (CVD), such as plasma polymerization, and vacuum deposition is preferably used.

The film formation by a solution process means a method, in which an organic compound is dissolved in a solvent capable of dissolving the same, and a film is formed by using the resulting solution. Specific examples thereof include ordinary methods, for example, a coating method, such as a casting method, a dip coating method, a die coater method, a roll coater method, a bar coater method and a spin coating method, a printing method, such as ink-jet method, screen printing method, gravure printing method, flexography printing method, offset printing method and microcontact printing method, and Langmuir-Blodgett (LB) method, and casting method, spin-coating method, preferably ink-jet method, gravure printing method, flexography printing method, offset printing method and microcontact printing method are used.

The coating solution for an organic semiconductor device of the invention capable of being used for film formation by a solution process will be described below.

In the case where the film is formed on a substrate by a solution process, the material for forming the layer may be dissolved or dispersed in a suitable organic solvent (for example, a hydrocarbon solvent, such as hexane, octane, decane, toluene, xylene, mesitylene, ethylbenzene, decalin and 1-methylnaphthalene, a ketone solvent, such as acetone, methyl ethyl ketone, methyl isobutyl ketone and cyclohexanone, a halogenated hydrocarbon solvent, such as dichloromethane, chloroform, tetrachloromethane, dichloroethane, trichloroethane, tetrachloroethane, chlorobenzene, dichlorobenzene and chlorotoluene, an ester solvent, such as ethyl acetate, butyl acetate and amyl acetate, an alcohol solvent, such as methanol, ethanol, propanol, butanol, pentanol, hexanol, cyclohexanol, methyl cellosolve, ethyl cellosolve and ethylene glycol, an ether solvent, such as diethyl ether, dibutyl ether, tetrahydrofuran, dioxane and anisole, an amide or imide solvent, such as N,N-dimethylformamide, N,N-dimethylacetamide, 1-methyl-2-pyrrolidone and 1-methyl-2-imidazolidinone, a sulfoxide solvent, such as dimethylsulfoxide, and a nitrile solvent, such as acetonitrile) and/or water to prepare a coating liquid, which may be then coated by various coating methods to form the thin film.

Devices

In some embodiments, the compounds of the disclosure are incorporated into a device. For example, the device includes, but is not limited to an OLED bulb, an OLED lamp, a television screen, a computer monitor, a mobile phone, and a tablet.

In some embodiments, an electronic device comprises an OLED comprising an anode, a cathode, and at least one organic layer comprising a light-emitting layer between the anode and the cathode, wherein the light-emitting layer comprises a host material; and a compound of Formula (I) or (II).

In some embodiments, the light-emitting layer comprises a compound of Formula (I) or (II) as a light-emitting material.

In some embodiments, the light-emitting layer comprises a compound of Formula (I) or (II) as an assist dopant.

In some embodiments, the light-emitting layer of the OLED further comprises a fluorescent material wherein the compound of Formula (I) or (II) converts triplets to singlets for the fluorescent emitter.

In some embodiments, compositions described herein may be incorporated into various light-sensitive or light-activated devices, such as a OLEDs or photovoltaic devices. In some embodiments, the composition may be useful in facilitating charge transfer or energy transfer within a device and/or as a hole-transport material. The device may be, for example, an organic light-emitting diode (OLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser).

Bulbs or Lamps

In some embodiments, an electronic device comprises an OLED comprising an anode, a cathode, and at least one organic layer comprising a light-emitting layer between the anode and the cathode, wherein the light-emitting layer comprises a host material;

a compound of Formula (I) or (II); wherein the compound of Formula (I) or (II) is a light-emitting material; and an OLED driver circuit.

In some embodiments, the light-emitting layer comprises a compound of Formula (I) or (II) as an assist dopant.

In some embodiments, a device comprises OLEDs that differ in color. In some embodiments, a device comprises an array comprising a combination of OLEDs. In some embodiments, the combination of OLEDs is a combination of three colors (e.g., RGB). In some embodiments, the combination of OLEDs is a combination of colors that are not red, green, or blue (for example, orange and yellow green). In some embodiments, the combination of OLEDs is a combination of two, four, or more colors.

In some embodiments, a device is an OLED light comprising:
  a circuit board having a first side with a mounting surface and an opposing second side, and defining at least one aperture;
  at least one OLED on the mounting surface, the at least one OLED configured to emanate light, comprising:
    an anode, a cathode, and at least one organic layer comprising a light-emitting layer between the anode and the cathode, wherein the light-emitting layer comprises
    a host material;
    a compound of Formula (I) or (II); wherein the compound of Formula (I) or (II) is a light-emitting material;
  a housing for the circuit board; and
  at least one connector arranged at an end of the housing, the housing and the connector defining a package adapted for installation in a light fixture.

In some embodiments, the light-emitting layer comprises a compound of Formula (I) or (II) as an assist dopant.

In some embodiments, the OLED light comprises a plurality of OLEDs mounted on a circuit board such that light emanates in a plurality of directions. In some embodiments, a portion of the light emanated in a first direction is deflected to emanate in a second direction. In some embodiments, a reflector is used to deflect the light emanated in a first direction.

Displays or Screens

In some embodiments, the compounds of Formula (I) or (II) can be used in a screen or a display. In some embodiments, the compounds of Formula (I) or (II) are deposited onto a substrate using a process including, but not limited to, vacuum evaporation, deposition, vapor deposition, or chemical vapor deposition (CVD). In some embodiments, the substrate is a photoplate structure useful in a two-sided etch provides a unique aspect ratio pixel. The screen (which may also be referred to as a mask) is used in a process in the manufacturing of OLED displays. The corresponding artwork pattern design facilitates a very steep and narrow tie-bar between the pixels in the vertical direction and a large, sweeping bevel opening in the horizontal direction. This allows the close patterning of pixels needed for high definition displays while optimizing the chemical deposition onto a TFT backplane.

The internal patterning of the pixel allows the construction of a 3-dimensional pixel opening with varying aspect ratios in the horizontal and vertical directions. Additionally, the use of imaged "stripes" or halftone circles within the pixel area inhibits etching in specific areas until these specific patterns are undercut and fall off the substrate. At that point the entire pixel area is subjected to a similar etch rate but the depths are varying depending on the halftone pattern. Varying the size and spacing of the halftone pattern allows etching to be inhibited at different rates within the pixel allowing for a localized deeper etch needed to create steep vertical bevels.

A preferred material for the deposition mask is invar. Invar is a metal alloy that is cold rolled into long thin sheet in a steel mill. Invar cannot be electrodeposited onto a rotating mandrel as the nickel mask. A preferred and more cost feasible method for forming the open areas in the mask used for deposition is through a wet chemical etching.

In some embodiments, a screen or display pattern is a pixel matrix on a substrate. In some embodiments, a screen or display pattern is fabricated using lithography (e.g., photolithography and e-beam lithography). In some embodiments, a screen or display pattern is fabricated using a wet chemical etch. In further embodiments, a screen or display pattern is fabricated using plasma etching.

Methods of Manufacturing Devices Using the Disclosed Compounds

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light-emitting layer, a counter electrode, and an encapsulation layer, and then is cut from the mother panel.

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light-emitting layer, a counter electrode, and an encapsulation layer, and then is cut from the mother panel.

In another aspect, provided herein is a method of manufacturing an organic light-emitting diode (OLED) display, the method comprising:
  forming a barrier layer on a base substrate of a mother panel;
  forming a plurality of display units in units of cell panels on the barrier layer;
  forming an encapsulation layer on each of the display units of the cell panels;
  applying an organic film to an interface portion between the cell panels.

In some embodiments, the barrier layer is an inorganic film formed of, for example, SiNx, and an edge portion of the barrier layer is covered with an organic film formed of polyimide or acryl. In some embodiments, the organic film helps the mother panel to be softly cut in units of the cell panel.

In some embodiments, the thin film transistor (TFT) layer includes a light-emitting layer, a gate electrode, and a source/drain electrode. Each of the plurality of display units may include a thin film transistor (TFT) layer, a planarization film formed on the TFT layer, and a light-emitting unit formed on the planarization film, wherein the organic film applied to the interface portion is formed of a same material as a material of the planarization film and is formed at a same time as the planarization film is formed. In some embodiments, a light-emitting unit is connected to the TFT layer with a passivation layer and a planarization film therebetween and an encapsulation layer that covers and protects the light-emitting unit. In some embodiments of the method of manufacturing, the organic film contacts neither the display units nor the encapsulation layer.

Each of the organic film and the planarization film may include any one of polyimide and acryl. In some embodiments, the barrier layer may be an inorganic film. In some embodiments, the base substrate may be formed of polyimide. The method may further include, before the forming of the barrier layer on one surface of the base substrate formed of polyimide, attaching a carrier substrate formed of a glass material to another surface of the base substrate, and before the cutting along the interface portion, separating the carrier substrate from the base substrate. In some embodiments, the OLED display is a flexible display.

In some embodiments, the passivation layer is an organic film disposed on the TFT layer to cover the TFT layer. In some embodiments, the planarization film is an organic film formed on the passivation layer. In some embodiments, the planarization film is formed of polyimide or acryl, like the organic film formed on the edge portion of the barrier layer. In some embodiments, the planarization film and the organic film are simultaneously formed when the OLED display is manufactured. In some embodiments, the organic film may be formed on the edge portion of the barrier layer such that a portion of the organic film directly contacts the base substrate and a remaining portion of the organic film contacts the barrier layer while surrounding the edge portion of the barrier layer.

In some embodiments, the light-emitting layer includes a pixel electrode, a counter electrode, and an organic light-emitting layer disposed between the pixel electrode and the counter electrode. In some embodiments, the pixel electrode is connected to the source/drain electrode of the TFT layer.

In some embodiments, when a voltage is applied to the pixel electrode through the TFT layer, an appropriate voltage is formed between the pixel electrode and the counter electrode, and thus the organic light-emitting layer emits light, thereby forming an image. Hereinafter, an image forming unit including the TFT layer and the light-emitting unit is referred to as a display unit.

In some embodiments, the encapsulation layer that covers the display unit and prevents penetration of external moisture may be formed to have a thin film encapsulation structure in which an organic film and an inorganic film are alternately stacked. In some embodiments, the encapsulation layer has a thin film encapsulation structure in which a plurality of thin films are stacked. In some embodiments, the organic film applied to the interface portion is spaced apart from each of the plurality of display units. In some embodiments, the organic film is formed such that a portion of the organic film directly contacts the base substrate and a remaining portion of the organic film contacts the barrier layer while surrounding an edge portion of the barrier layer.

In one embodiment, the OLED display is flexible and uses the soft base substrate formed of polyimide. In some embodiments, the base substrate is formed on a carrier substrate formed of a glass material, and then the carrier substrate is separated.

In some embodiments, the barrier layer is formed on a surface of the base substrate opposite to the carrier substrate. In one embodiment, the barrier layer is patterned according to a size of each of the cell panels. For example, while the base substrate is formed over the entire surface of a mother panel, the barrier layer is formed according to a size of each of the cell panels, and thus a groove is formed at an interface portion between the barrier layers of the cell panels. Each of the cell panels can be cut along the groove.

In some embodiments, the method of manufacture further comprises cutting along the interface portion, wherein a groove is formed in the barrier layer, wherein at least a portion of the organic film is formed in the groove, and wherein the groove does not penetrate into the base substrate. In some embodiments, the TFT layer of each of the cell panels is formed, and the passivation layer which is an inorganic film and the planarization film which is an organic film are disposed on the TFT layer to cover the TFT layer. At the same time as the planarization film formed of, for example, polyimide or acryl is formed, the groove at the interface portion is covered with the organic film formed of, for example, polyimide or acryl. This is to prevent cracks from occurring by allowing the organic film to absorb an impact generated when each of the cell panels is cut along the groove at the interface portion. That is, if the entire barrier layer is entirely exposed without the organic film, an impact generated when each of the cell panels is cut along the groove at the interface portion is transferred to the barrier layer, thereby increasing the risk of cracks. However, in one embodiment, since the groove at the interface portion between the barrier layers is covered with the organic film and the organic film absorbs an impact that would otherwise be transferred to the barrier layer, each of the cell panels may be softly cut and cracks may be prevented from occurring in the barrier layer. In one embodiment, the organic film covering the groove at the interface portion and the planarization film are spaced apart from each other. For example, if the organic film and the planarization film are connected to each other as one layer, since external moisture may penetrate into the display unit through the planarization film and a portion where the organic film remains, the organic film and the planarization film are spaced apart from each other such that the organic film is spaced apart from the display unit.

In some embodiments, the display unit is formed by forming the light-emitting unit, and the encapsulation layer is disposed on the display unit to cover the display unit. As such, once the mother panel is completely manufactured, the carrier substrate that supports the base substrate is separated from the base substrate. In some embodiments, when a laser beam is emitted toward the carrier substrate, the carrier substrate is separated from the base substrate due to a difference in a thermal expansion coefficient between the carrier substrate and the base substrate.

In some embodiments, the mother panel is cut in units of the cell panels. In some embodiments, the mother panel is cut along an interface portion between the cell panels by using a cutter. In some embodiments, since the groove at the interface portion along which the mother panel is cut is covered with the organic film, the organic film absorbs an impact during the cutting. In some embodiments, cracks may be prevented from occurring in the barrier layer during the cutting.

In some embodiments, the methods reduce a defect rate of a product and stabilize its quality.

Another aspect is an OLED display including: a barrier layer that is formed on a base substrate; a display unit that is formed on the barrier layer; an encapsulation layer that is formed on the display unit; and an organic film that is applied to an edge portion of the barrier layer.

EXAMPLES

An embodiment of the present disclosure provides the preparation of compounds of Formula (I) or (II) according to the procedures of the following example(s), using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present disclosure.

General Information on Analytical Methods

The features of the invention will be described more specifically with reference to examples below. The materials, processes, procedures and the like shown below may be appropriately modified unless they deviate from the substance of the invention. Accordingly, the scope of the invention is not construed as being limited to the specific examples shown below. The characteristics of samples were evaluated by using NMR (Nuclear Magnetic Resonance 500 MHz, produced by Bruker), LC/MS (Liquid Chromatography Mass Spectrometry, produced by Waters), AC3 (produced by RIKEN KEIKI), High-performance UV/Vis/NIR Spectrophotometer (Lambda 950, produced by PerkinElmer, Co., Ltd.), Fluorescence Spectrophotometer (FluoroMax-4, produced by Horiba, Ltd.), Photonic multichannel analyzer (PMA-12 C10027-01, produced by Hamamatsu Photonics K.K.), Absolute PL Quantum Yield Measurement System (C11347, produced by Hamamatsu Photonics K.K.), Automatic Current voltage brightness measurement system (ETS-170, produced by System engineers co ltd), Life Time Measurement System (EAS-26C, produced by System engineers co ltd), and Streak Camera (Model C4334, produced by Hamamatsu Photonics K.K.).

Example 1

The principle of the features may be described as follows for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

Example 2

The compounds of the invention can be synthesized by any method known to one of ordinary skills in the art. The compounds are synthesized from the commonly available starting material. The various moieties can be assembled via linear or branched synthetic routes.

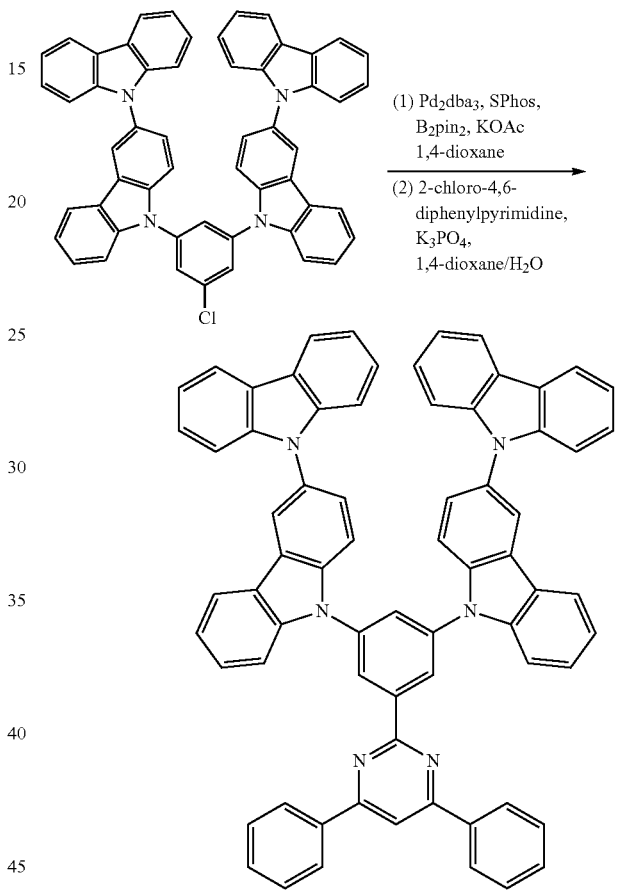

Synthesis of 9,9'''-(5-(4,6-diphenylpyrimidin-2-yl)-1,3-phenylene)bis(9H-3,9'-bicarbazole)) (Compound 1)

A mixture of 9,9'''-(5-chloro-1,3-phenylene)bis((9H-3,9'-bicarbazole)) (906 mg, 1.17 mmol), bis(pinacolato)diboron (297 mg, 1.17 mmol), tris(dibenzylideneacetone)dipalladium(0) (9.2 mg, 0.010 mmol), SPhos (16 mg, 0.040 mmol), potassium acetate (0.191 g, 1.95 mmol) in anhydrous 1,4-dioxane (5 mL) was stirred and heated at 110° C. under a nitrogen atmosphere for 2 h. Until the starting aryl halide had been completely consumed, 2-chloro-4,6-diphenylpyrimidine (261 mg, 0.98 mmol) in degassed 1,4-dioxane (3 mL) and potassium phosphate (1.04 g, 4.88 mmol) in degassed deionized water were added via syringe into the reaction solution and remained heated at 110° C. for another 18 h. After allowing to room temperature, the reaction mixture was filtered through a Celite pad rinsing with $CHCl_3$. The filtrate was evaporated in vacuo. The obtained residue was purified by column chromatography on silica gel using 3:1 (v/v) hexane/chloroform as eluent to afford compound 1 as a white solid (0.483 g, 50.8%). $^1$H NMR (500 MHz, CDCl$_3$, δ): 9.18 (s, 2H), 8.36 (s, 2H), 8.31-29 (m, 4H), 8.20-8.17 (m, 7H), 8.11 (t, J=2.0 Hz, 1H), 7.85 (d, J=8.5 Hz, 2H), 7.73 (d, J=8.0 Hz, 2H), 7.64 (dd, J=8.5, 2.0 Hz, 2H), 7.57-7.55 (m, 8H), 7.43-7.39 (m, 10H), 7.30 (t, J=8.0 Hz, 4H).

afford compound 2 as a white solid (0.550 g, 26.3%). $^1$H NMR (500 MHz, CDCl$_3$, δ): 9.24 (s, 2H), 8.79 (d, J=7.0 Hz, 4H), 8.37 (s, 2H), 8.22 (t, J=2.0 Hz, 1H), 8.21-8.19 (m, 6H), 7.84 (d, J=8.5 Hz, 2H), 7.73 (d, J=8.0 Hz, 2H), 7.67-7.62 (m, 4H), 7.60-7.58 (m, 6H), 7.47-7.40 (m, 10H), 7.32-7.30 (m, 4H).

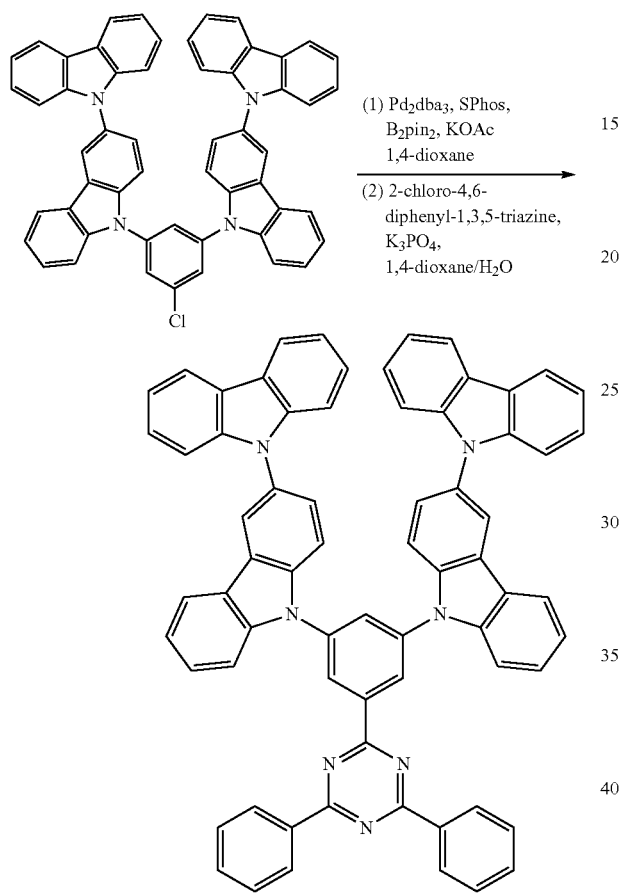

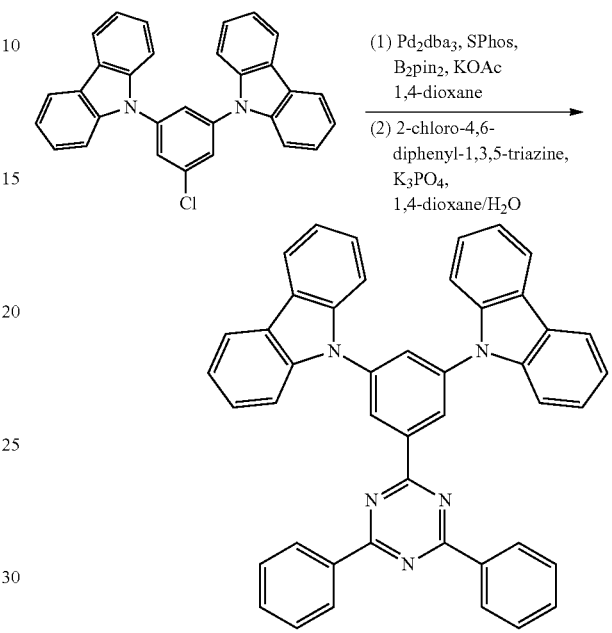

Synthesis of 9,9''-(5-(4,6-diphenyl-1,3,5-triazin-2-yl)-1,3-phenylene)bis(9H-3,9'-bicarbazole) (Compound 2)

A mixture of 9,9''-(5-chloro-1,3-phenylene)bis((9H-3,9'-bicarbazole)) (2.00 g, 2.59 mmol), bis(pinacolato)diboron (0.657 g, 2.59 mmol), tris(dibenzylideneacetone)dipalladium(0) (40 mg, 0.044 mmol), SPhos (35 mg, 0.086 mmol), potassium acetate (0.423 g, 4.31 mmol) in anhydrous 1,4-dioxane (10 mL) was stirred and heated at 110° C. under a nitrogen atmosphere for 3 h. Until the starting aryl halide had been completely consumed, 2-chloro-4,6-diphenyl-1,3,5-triazine (0.577 g, 2.16 mmol) in degassed 1,4-dioxane (5 mL) and potassium phosphate (2.29 g, 10.8 mmol) in degassed deionized water (5 mL) were added via syringe into the reaction solution and remained heated at 110° C. for another 18 h. After allowing to room temperature, the reaction mixture was filtered through a Celite pad rinsing with CHCl$_3$. The filtrate was evaporated in vacuo. The obtained residue was purified by column chromatography on silica gel using 2:1 (v/v) hexane/chloroform as eluent to Synthesis of 9,9'-(5-(4,6-diphenyl-1,3,5-triazin-2-yl)-1,3-phenylene)bis(9H-carbazole) (Compound 3)

A mixture of 9,9'-(5-chloro-1,3-phenylene)bis(9H-carbazole) (0.60 g, 1.35 mmol), bis(pinacolato)diboron (0.34 mg, 1.35 mmol), tris(dibenzylideneacetone)dipalladium(0) (10 mg, 0.011 mmol), SPhos (18 mg, 0.045 mmol), potassium acetate (0.22 g, 2.26 mmol) in anhydrous 1,4-dioxane (10 mL) was stirred and heated at 110° C. under a nitrogen atmosphere for 2 h. Until the starting aryl halide had been completely consumed, 2-chloro-4,6-diphenyl-1,3,5-triazine (303 mg, 1.13 mmol) in 1,4-dioxane (5 mL) and potassium phosphate (1.20 g, 5.64 mmol) in deionized water were added via syringe into the reaction solution, and remained heated at 110° C. for another 18 h. After allowed to room temperature, the reaction mixture was filtered through a Celite pad rinsing with toluene. The filtrate was evaporated in vacuo. The obtained residue was purified by column chromatography on silica gel using hexane/chloroform as eluent to afford compound 3 as a white solid (0.41 g, 55.6%).

Example 3

Preparation of Neat Films

In this example, the compound synthesised in Example 2 is vapor-deposited on a quartz substrate by a vacuum vapor deposition method under a condition of a vacuum degree of 10$^{-3}$ Pa or less, so as to form a thin film having a thickness of 70 nm.

Preparation of Doped Films

The compound and host are also vapor-deposited from a separate vapor deposition source on a quartz substrate by vacuum vapor deposition method under a condition of a vacuum degree of $10^{-3}$ Pa or less, so as to form a thin film having a thickness of 100 nm and a concentration of the compound of 20% by weight.

Evaluation of the Optical Properties

The samples were irradiated with light having a wavelength of 300 nm at 300 K, and thus the light emission spectrum was measured and designated as fluorescence. The spectrum at 77K was also measured and designated as phosphorescence. The lowest singlet energy (S1) and the lowest triplet energy (T1) was estimated from the onset of fluorescence and phsphorescence spectrum respectively. $\Delta E_{ST}$ was calculated from the energy gap between S1 and T1. PLQY was also measured by excitation light 300 nm. The time resolved spectrum was obtained by excitation light 337 nm with Streak Camera, and the component with a short light emission lifetime was designated as fluorescent light, whereas the component with a long light emission lifetime was designated as delayed fluorescent light. The lifetimes of the fluorescent light component (Tpron) and the delayed fluorescent light component (Tdcay) were calculated from the decay curves.

Preparation and Measurement of OLEDs

Thin films were laminated on a glass substrate having formed thereon an anode formed of indium tin oxide (ITO) having a thickness of 50 nm, by a vacuum vapor deposition method at a vacuum degree of $1.0 \times 10^{-4}$ Pa or less. Firstly, HAT-CN was formed to a thickness of 60 nm on ITO, and thereon TrisPCz was formed to a thickness of 30 nm. PYD2Cz was formed to a thickness of 5 nm, and thereon the compound and host were then vapor-co-deposited from separate vapor deposition sources to form a layer having a thickness of 30 nm, which was designated as a light-emitting layer. At this time, the concentration of the compound was 30% by weight. SF3-TRZ was formed to a thickness of 10 nm, and thereon SF3-TRZ and Liq were vapor-co-deposited to a thickness of 30 nm. Liq was then vacuum vapor-deposited to a thickness of 2 nm, and then aluminum (Al) was vapor-deposited to a thickness of 100 nm to form a cathode, thereby producing organic electroluminescent devices and measured its photoelectrical properties.

Film Evaluation

|  | λ(nm) | PLQY (%) ( Max) |
|---|---|---|
| compound 1 (20 wt % in PYD-2Cz) | 490 | 60.7 |
| compound 2 (20 wt % in PYD-2Cz) | 488 | 60.7 |
| compound 3 (neat film) | 455 | 11.7 |

Device Evaluation

|  | λ(nm) | EQE (%) ( Max) | EQE (%) ( @1000 cd) | LT 90 (h) (@ 750 cd) |
|---|---|---|---|---|
| compound 1 | 501 | 12.6 | 9.4 | 3.8 |
| compound 3 | 471 | 5.0 | 2.1 | 1 |

HAT-CN (60)/trisPCz (30)/PYD2Cz (5)/30 wt %-TADF: PYD2Cz (30)/SF3TRZ (10)/30 wt %-LiQ:SF3TRZ (30)/ LiQ (2)

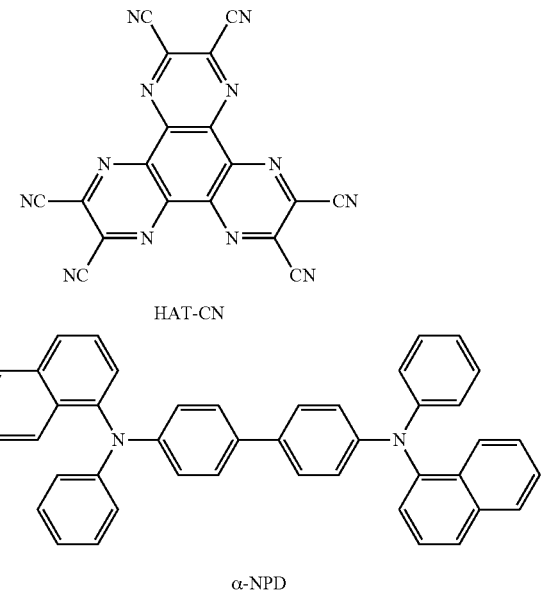

HAT-CN

α-NPD

Tris-PCz

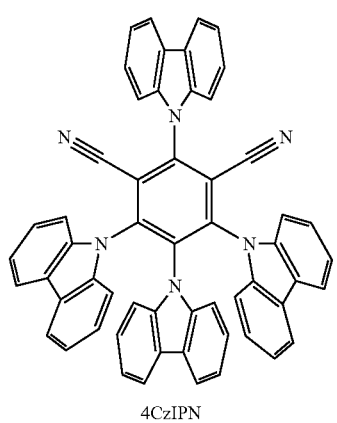

4CzIPN

-continued

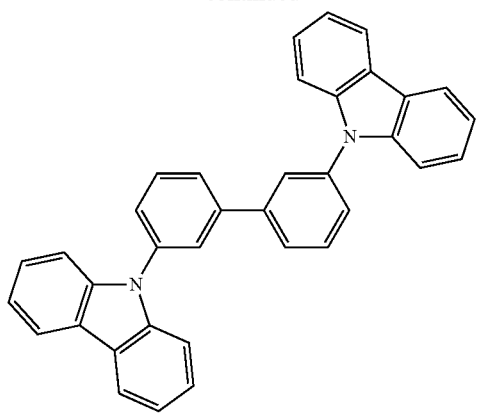

mCBP

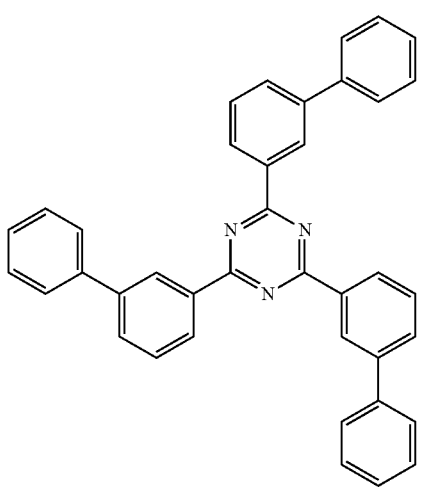

T2T

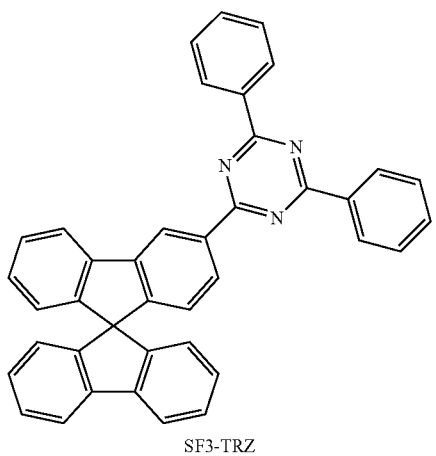

SF3-TRZ

-continued

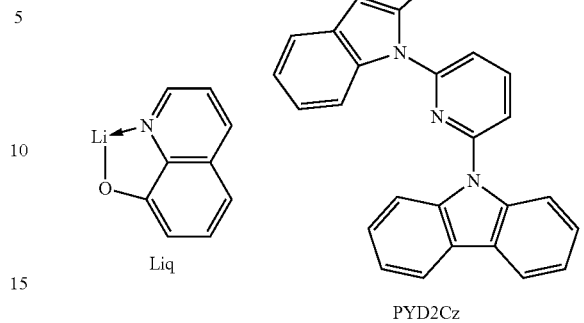

Liq

PYD2Cz

We claim:
1. An organic light-emitting diode (OLED), comprising an anode, a cathode, and at least one organic layer comprising a light-emitting layer between the anode and the cathode, wherein the light-emitting layer comprises:
   a host material; and
   a compound of Formula (II) in an amount of 50% by weight or less:

$$D \underset{D'}{\overset{A}{\diagup\!\!\!\diagdown}} \quad (II)$$

wherein
A is selected from

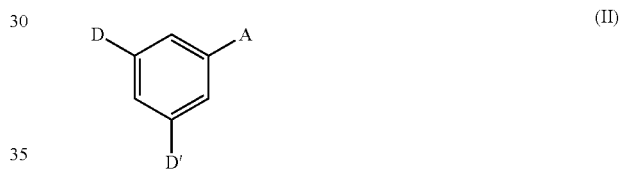   A1

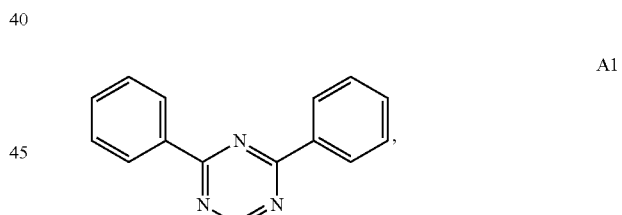   A2

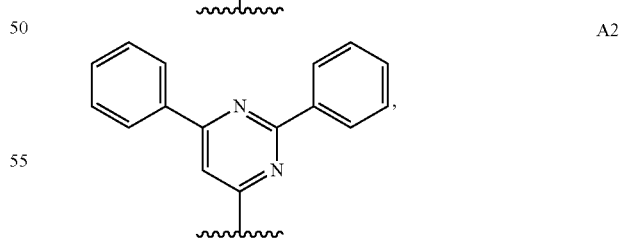   A3

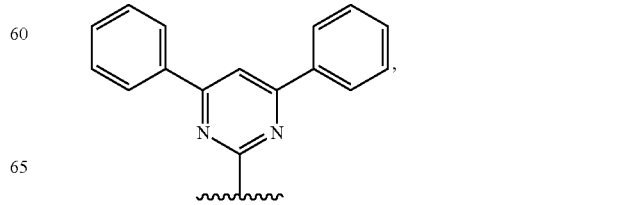

-continued
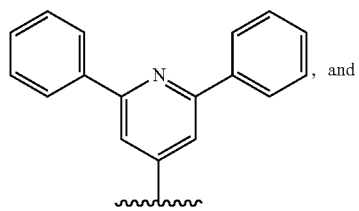, and
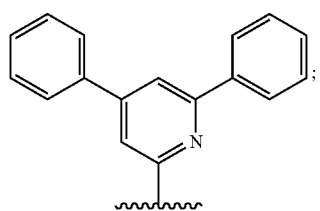;
D and D' are independently
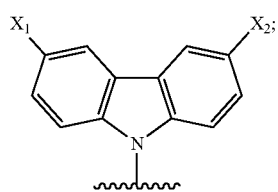
X₁ is Ar;
X₂ is selected from
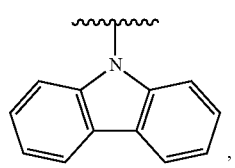 Ar20
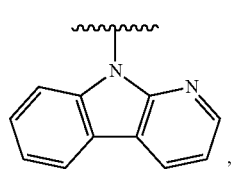 Ar21
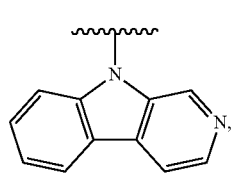 Ar22
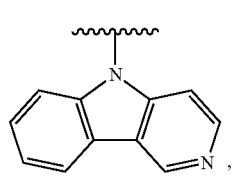 Ar23
-continued
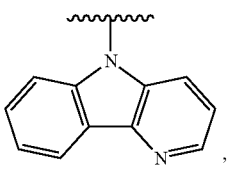 Ar24
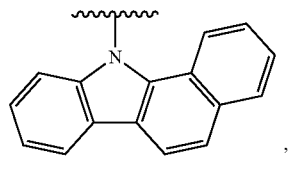 Ar25
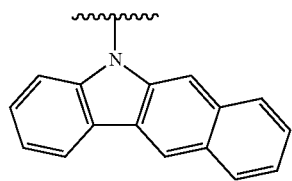 Ar26
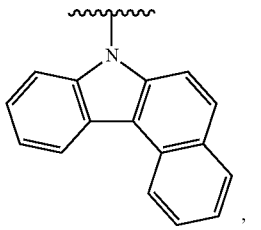 Ar27
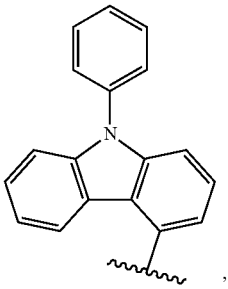 Ar36
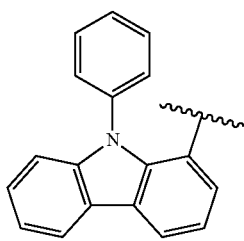 Ar37
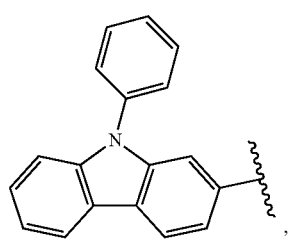 Ar38

-continued
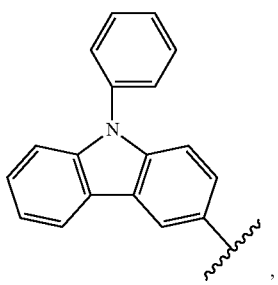       Ar39
Ar is independently selected from
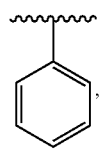       Ar1
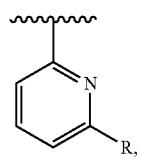       Ar2
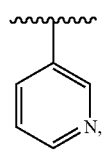       Ar3
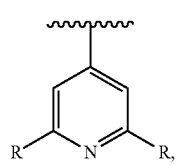       Ar4
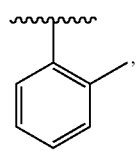       Ar5
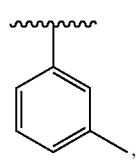       Ar6
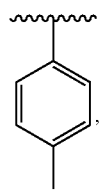       Ar7
-continued
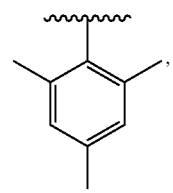       Ar8
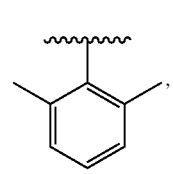       Ar9
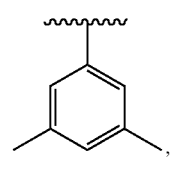       Ar10
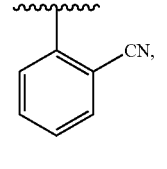       Ar11
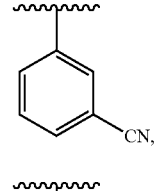       Ar12
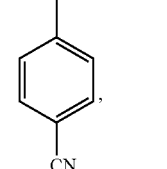       Ar13
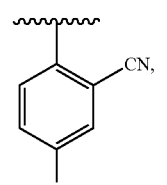       Ar14
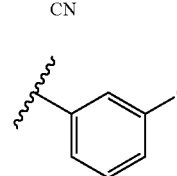       Ar15
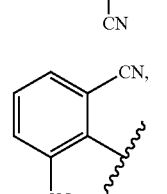       Ar16

| | |
|---|---|
| 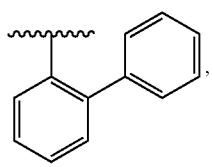 Ar17 | 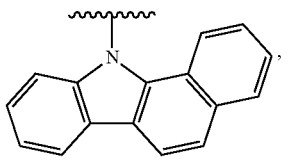 Ar25 |
| 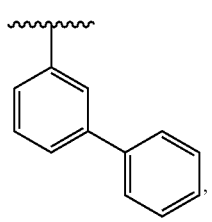 Ar18 | 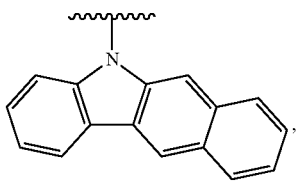 Ar26 |
| 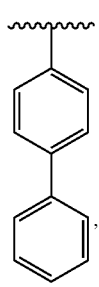 Ar19 | 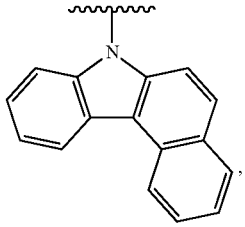 Ar27 |
| 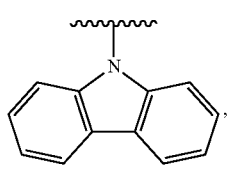 Ar20 | 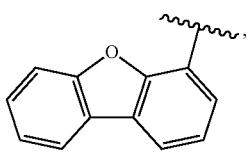 Ar28 |
| 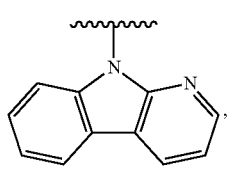 Ar21 | 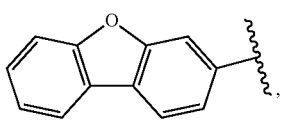 Ar29 |
| 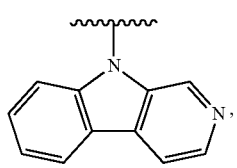 Ar22 | 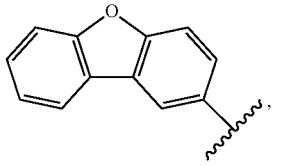 Ar30 |
| 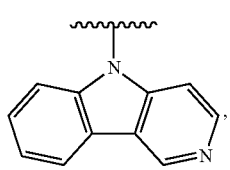 Ar23 | 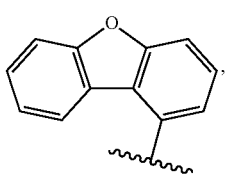 Ar31 |
| | 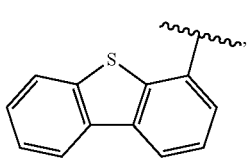 Ar32 |
| 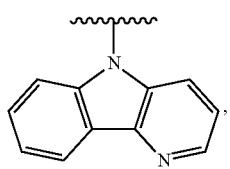 Ar24 | 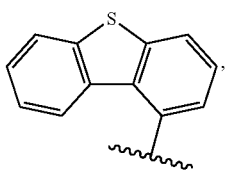 Ar33 |

Ar34 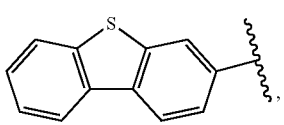

Ar35 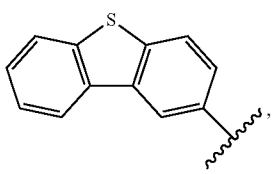

Ar36 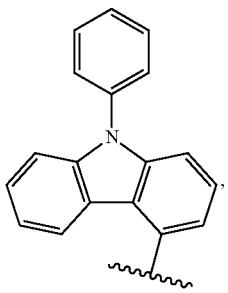

Ar37 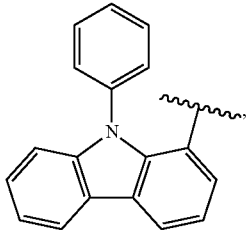

Ar38 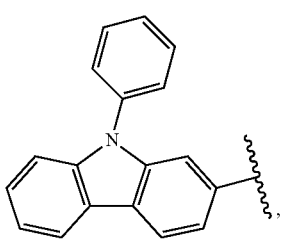

Ar39 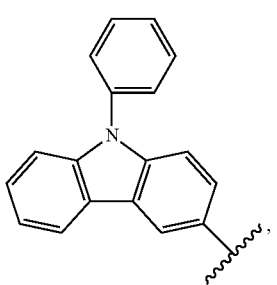

Ar40 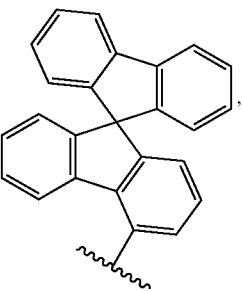

Ar41 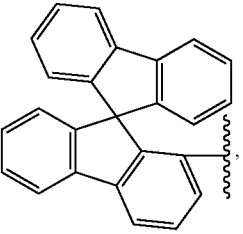

Ar42 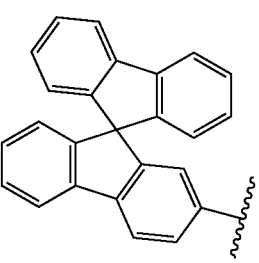 and

Ar43 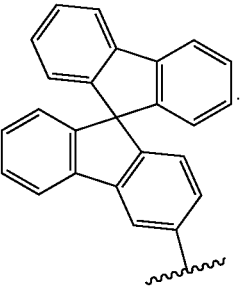

2. The organic light-emitting diode (OLED) of claim 1, wherein the light-emitting layer comprises the compound of Formula (II) in an amount of 20% by weight or less.

3. The organic light-emitting diode (OLED) of claim 1, wherein the light-emitting layer comprises the compound of Formula (II) in an amount of 10% by weight or less.

4. The organic light-emitting diode (OLED) of claim 1, wherein A is A1.

5. The organic light-emitting diode (OLED) of claim 1, wherein A is A2.

6. The organic light-emitting diode (OLED) of claim 1, wherein A is A3.

7. The organic light-emitting diode (OLED) of claim 1, wherein A is A4.

8. The organic light-emitting diode (OLED) of claim 1, wherein A is A5.

9. The organic light-emitting diode (OLED) of claim 1, wherein Ar is selected from Ar1, Ar2, Ar3, Ar4, Ar5, Ar6, Ar7, Ar8, Ar9, and Ar10.

10. The organic light-emitting diode (OLED) of claim 1, wherein Ar is selected from Ar11, Ar12, Ar13, Ar14, Ar15, Ar16, Ar17, Ar18, and Ar19.

11. The organic light-emitting diode (OLED) of claim 1, wherein Ar is selected from Ar20, Ar21, Ar22, Ar23, and Ar24.

12. The organic light-emitting diode (OLED) of claim 1, wherein Ar is selected from Ar25, Ar26, and Ar27.

13. The organic light-emitting diode (OLED) of claim 1, wherein Ar is selected from Ar28, Ar29, Ar30, Ar31, Ar32, Ar33, Ar34, and Ar35.

14. The organic light-emitting diode (OLED) of claim 1, wherein Ar is selected from Ar36, Ar37, Ar38, Ar39, Ar40, Ar41, Ar42, and Ar43.

15. The organic light-emitting diode (OLED) of claim 1, wherein D and D' are the same.

16. The organic light-emitting diode (OLED) of claim 1, wherein D and D' are different.

17. The organic light-emitting diode (OLED) of claim 1, wherein the
compound of Formula (II) is selected from

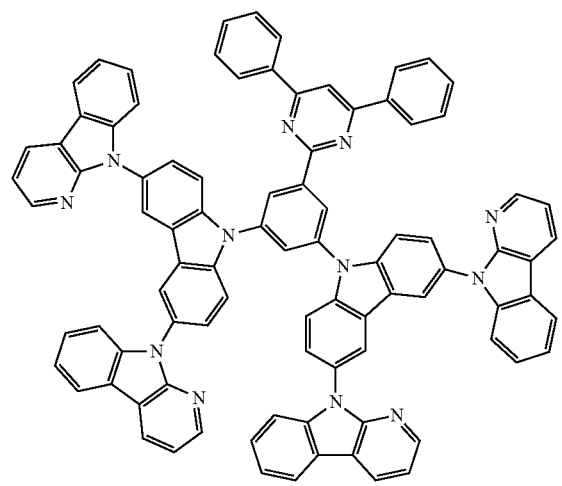

and

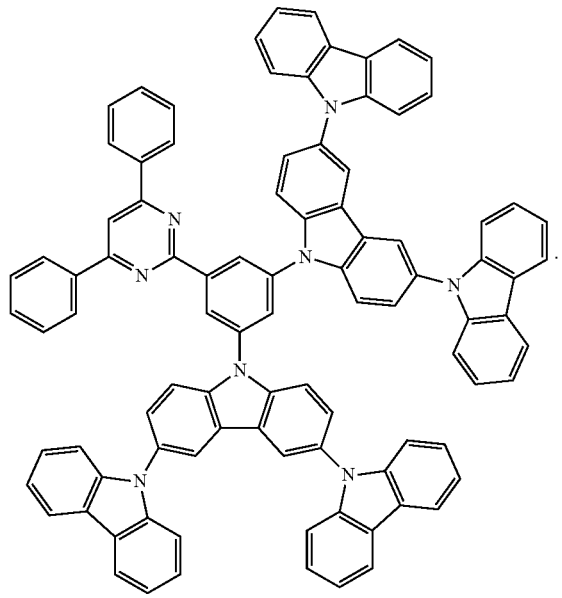

18. An organic light-emitting diode (OLED) of claim 1, comprising an anode, a cathode, and at least one organic layer comprising a light-emitting layer between the anode and the cathode, wherein the light-emitting layer comprises:

a host material; and a compound selected from

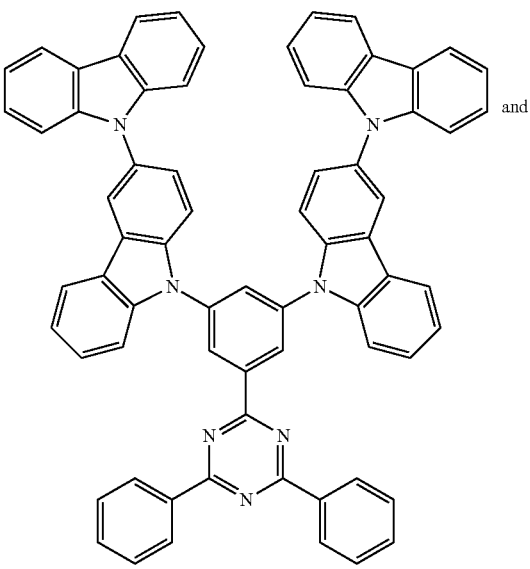

and

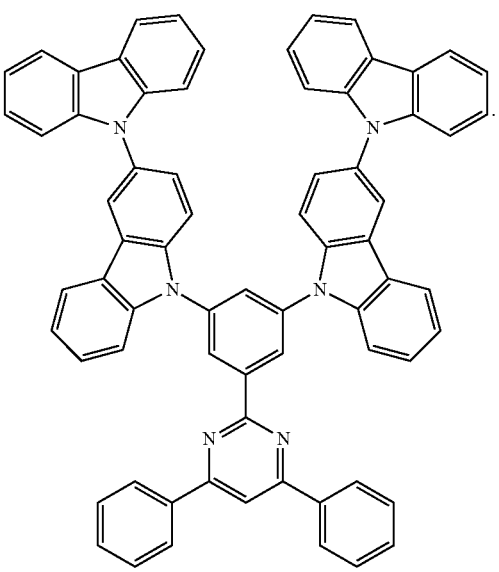

* * * * *